United States Patent [19]

Kathawala et al.

[11] Patent Number: 5,001,255

[45] Date of Patent: Mar. 19, 1991

[54] IDENE ANALOGS OF MEVALONOLACTONE AND DERIVATIVES THEREOF

[75] Inventors: Faizulla G. Kathawala, Mountain Lakes; Sompong Wattanasin, Hopatcong, both of N.J.

[73] Assignee: Sandoz Pharm. Corp., E. Hanover, N.J.

[21] Appl. No.: 214,560

[22] Filed: Jul. 1, 1988

Related U.S. Application Data

[63] Continuation-in-part of Ser. No. 837,479, Mar. 7, 1986, abandoned, which is a continuation-in-part of Ser. No. 677,917, Dec. 4, 1984, abandoned.

[51] Int. Cl.$^5$ ............................................. C07C 69/76
[52] U.S. Cl. ........................................ 560/56; 560/53; 556/441; 549/264; 549/291; 562/462; 562/466
[58] Field of Search .................. 560/56, 53; 549/264, 549/291; 562/462, 466; 514/530, 569

[56] References Cited

U.S. PATENT DOCUMENTS

| | | | |
|---|---|---|---|
| 3,207,779 | 9/1965 | Cutler | 560/56 |
| 3,532,752 | 10/1970 | Shen | 560/56 |
| 3,668,241 | 6/1972 | Cragoe et al. | 560/56 |
| 3,983,140 | 9/1976 | Endo et al. | 260/343.5 |
| 4,006,180 | 2/1977 | Cragoe et al. | 560/56 |
| 4,012,524 | 3/1977 | Cragoe et al. | 560/56 |
| 4,057,573 | 11/1977 | Haas et al. | 560/56 |
| 4,070,539 | 1/1978 | Cragoe et al. | 560/56 |
| 4,125,731 | 11/1978 | Sugie et al. | 560/56 |
| 4,137,322 | 1/1979 | Endo et al. | 424/273 |
| 4,198,425 | 4/1980 | Mitsui et al. | 424/279 |
| 4,248,889 | 2/1981 | Oka et al. | 424/308 |
| 4,255,444 | 3/1981 | Oka et al. | 424/279 |
| 4,308,378 | 12/1981 | Stokker | 542/441 |
| 4,361,515 | 11/1982 | Terahara et al. | 549/292 |
| 4,375,475 | 3/1983 | Willard et al. | 424/279 |
| 4,474,971 | 10/1984 | Wareing | 549/214 |
| 4,588,715 | 5/1986 | Damon | 514/63 |
| 4,613,610 | 9/1986 | Wareing | 514/406 |
| 4,647,576 | 3/1987 | Hoefle | 514/422 |
| 4,654,363 | 3/1987 | Prugh | 560/56 |

FOREIGN PATENT DOCUMENTS

| | | |
|---|---|---|
| 142146 | 5/1985 | European Pat. Off. |
| 84/02131 | 6/1984 | PCT Int'l Appl. |
| 84/02903 | 8/1984 | PCT Int'l Appl. |
| 86/03488 | 6/1986 | PCT Int'l Appl. |

OTHER PUBLICATIONS

Hulcher, Arch. Biochem. Biophys. 146, 422–427 (1971).
Sato et al., Chem. Pharm. Bull. 28, 1509–1525 (1980).
Singer et al., Proc. Soc. Exp. Biol. Med. 102, 370–373 (1959).

*Primary Examiner*—Paul J. Killos
*Attorney, Agent, or Firm*—Gerald D. Sharkin; Richard E. Vila; Melvyn M. Kassenoff

[57] ABSTRACT

Compounds of the formula

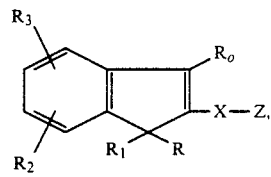

the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

27 Claims, No Drawings

IDENE ANALOGS OF MEVALONOLACTONE AND DERIVATIVES THEREOF

This is a continuation-in-part of Ser. No. 06/837,479, filed Mar. 7, 1986 and now abandoned, which is a continuation-in-part of application Ser. No. 06/677,917, filed Dec. 4, 1984 and now abandoned.

This invention relates to compounds of the formula

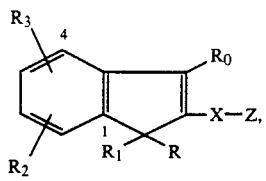

(I)

wherein $R_o$ is $C_{1-6}$alkyl not containing an asymmetric carbon atom, $C_{3-7}$cycloalkyl or

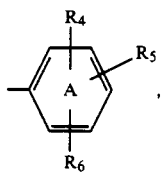

wherein $R_4$ is hydrogen, $C_{1-3}$alkyl, n-butyl, i-butyl, t-butyl, $C_1$-$C_3$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, and $R_6$ is hydrogen, $C_{1-2}$alkyl, $C_{1-2}$alkoxy, fluoro or chloro, with the provisos that not more than one of $R_4$ and $R_5$ is trifluoromethyl, not more than one of $R_4$ and $R_5$ is phenoxy, and not more than one of $R_4$ and $R_5$ is benzyloxy, R is hydrogen or primary or secondary $C_{1-6}$alkyl not containing an asymmetric carbon atom, and $R_1$ is primary or secondary $C_{1-6}$alkyl not containing an asymmetric carbon atom or (Z)—$CH_2$—CH=CH—$CH_2$—, wherein m is 2, 3, 4, 5 or 6, $R_2$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ benzyloxy, X is —$(CH_2)_n$—, —CH=CH—, —$CH_2$—CH=CH— or —CH=CH—$CH_2$—, wherein n is 1, 2 or 3, and

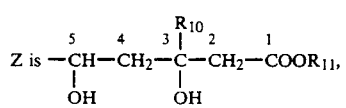

(a)

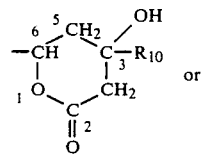

(b)

or

-continued

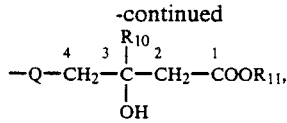

(c)

wherein Q is

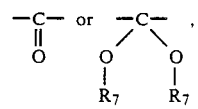

wherein each $R_7$ is primary or secondary $C_{1-6}$alkyl not containing an asymmetric carbon atom, the two $R_7$s, is being the same, or the two $R_7$s taken together are —$(CH_2)_q$—, wherein q is 2 or 3, $R_{10}$ is hydrogen or $C_{1-3}$alkyl, and $R_{11}$ is hydrogen, $R_{12}$ or M, wherein $R_{12}$ is a physiologically acceptable ester group, and M is a pharmaceutically acceptable cation, with the provisos that (1) Z may be a group of Formula c only when (i) X is —CH=CH— or —$CH_2$—CH=CH—, (ii) $R_{10}$ is $C_{1-3}$alkyl or (iii) both (i) and (ii) and (2) when Z is a group of Formula c wherein Q is

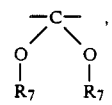

$R_{11}$ must be $R_{12}$ or M, processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable ester group" is meant a group which, together with the —COO— radical to which it is attached, forms an ester group which is physiologically acceptable The preferred such groups are physiologically acceptable and hydrolyzable ester groups. By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R_{11}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_{12}$.

For the avoidance of doubt, throughout this specification it is the right-hand side of the X radical that is attached to the Z group.

The compounds of Formula I may be divided into six groups, viz., the compounds of Formula I wherein R is hydrogen or primary or secondary $C_{1-6}$alkyl not containing an asymmetric carbon atom, $R_1$ is primary or secondary $C_{1-6}$alkyl not containing an asymmetric carbon atom, and Z is a group of Formula a (Group IAa), the corresponding compounds wherein Z is a group of Formula b (Group IAb), the corresponding compounds wherein Z is a group of Formula c (Group IAc), the compounds of Formula I wherein R and $R_1$ taken together are $-(CH_2)_m-$ or $(Z)-CH_2-CH=CH-CH_2-$, and Z is a group of Formula a (Group IBa), the corresponding compounds wherein Z is a group of Formula b (Group IBb) and the corresponding compounds wherein Z is a group of Formula c (Group IBc).

As is self-evident to those in the art, each compound of Groups IAa, IAb, IBa and IBb (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that R and $R_1$ are identical or taken together are $-(CH_2)_m-$ or $(Z)-CH_2-CH=CH-CH_2-$ and that $R_{11}$ does not contain any center of asymmetry. The four stereoisomers may be designated as the R,R, R,S, S,R and S,S enantiomers, all four stereoisomers being within the scope of this invention. When R and $R_1$ are different and/or $R_{11}$ contains one or more centers of asymmetry, there are eight or more stereoisomers. Since it is preferred that R and $R_1$ be identical or taken together $-(CH_2)_m-$ or $(Z)-CH_2-CH=CH-CH_2-$ and that $R_{11}$ not contain a center of asymmetry and for reasons of simplicity any additional stereoisomers resulting from the presence of a center of asymmetry in the 1-position of the indene ring and/or one or more centers of asymmetry in $R_{11}$ will usually be ignored, it being assumed that R and $R_1$ are identical or taken together are $-(CH_2)_m-$ or $(Z)-CH_2-CH=CH-CH_2-$ and that $R_{11}$ is free of centers of asymmetry. As is also self-evident, each compound of Groups IAc and IBc (and every subscope and species thereof) has one center of asymmetry (the carbon atom bearing the hydroxy group in the group of Formula c) and, therefore, there are two enantiomers of each compound, provided that R and $R_1$ are identical or taken together are $-(CH_2)_m-$ or $(Z)-CH_2-CH=CH-CH_2-$ and that $R_{11}$ does not contain any center of asymmetry. The two stereoisomers may be designated as the 3R and 3S isomers, both being within the scope of this invention. When R and $R_1$ are different and/or $R_{11}$ contains one or more centers of asymmetry, there are four or more stereoisomers. For the reasons set forth above, any additional stereoisomers resulting from the presence of a center of asymmetry in the 1-position of the indene ring and/or one or more centers of asymmetry in $R_{11}$ will usually be ignored.

Q is preferably $-CO-$.

$R_o$ is preferably $R_o'$, where $R_o'$ is $C_{1-4}$alkyl not containing an asymmetric carbon atom or Ring A, particularly Ring A, more preferably $R_o''$, where $R_o''$ is Ring A wherein $R_4$ is $R_4'$, $R_5$ is $R_5'$, and $R_6$ is $R_6'$, even more preferably $R_o'''$, where $R_o'''$ is Ring A wherein $R_4$ is $R_4''$, $R_5$ is $R_5''$, and $R_6$ is $R_6''$, and most preferably $R_o''''$, where $R_o''''$ is Ring A wherein $R_4$ is $R_4'''$, $R_5$ is $R_5'''$, and $R_6$ is $R_6'''$. In $R_o''''$, $R_4'''$ is preferably $R_4''''$.

When R is hydrogen or primary or secondary $C_{1-6}$alkyl not containing an asymmetric carbon atom:

R is preferably R', where R' is hydrogen or primary or secondary $C_{1-4}$alkyl not containing an asymmetric carbon atom, ore preferably R'', where R'' is hydrogen or $C_{1-2}$alkyl, and most preferably $C_{1-2}$alkyl, and $R_1$ is preferably $R_1'$, where $R_1'$ is primary or secondary $C_{1-4}$alkyl not containing an asymmetric carbon atom, more preferably $R_1''$, where $R_1''$ is $C_{1-3}$alkyl, and most preferably $C_{1-2}$alkyl.

Preferably, when R, R', etc. is other than hydrogen, R, R', etc., as the case may be, is identical to $R_1$, $R_1'$, etc., as the case may be.

When R and $R_1$ taken together are $-(CH_2)_m-$ or $(Z)-CH_2-CH=CH-CH_2-$, they are preferably $-(CH_2)_m-$, more preferably $-(CH_2)_{m'}-$, even more preferably $-(CH_2)_{m''}-$ and most preferably $-(CH_2)_{m'''}-$, especially $-(CH_2)_4-$, wherein m is as defined above, and m', m'' and m''' are as defined below $R_2$ is preferably $R_2'$, where $R_2'$ is hydrogen, $C_{1-3}$alkyl, methoxy, fluoro, chloro or benzyloxy, more preferably $R_2''$, where $R_2''$ is hydrogen or $C_{1-3}$alkyl, and most preferably hydrogen.

$R_3$ is preferably $R_3'$, where $R_3'$ is hydrogen or $C_{1-3}$alkyl, and more preferably hydrogen.

Preferably, not more than one of $R_2$ and $R_3$ is a member of the group consisting of t-butyl, trifluoromethyl, phenoxy and benzyloxy More preferably, $R_2$ and $R_3$ are not ortho to each other unless at least one of them is a member of the group consisting of hydrogen, $C_{1-2}$alkyl, $C_{1-2}$alkoxy, fluoro and chloro.

$R_4$ is preferably $R_4'$, where $R_4'$ is hydrogen, $C_{1-3}$alkyl, trifluoromethyl, fluoro or chloro, more preferably $R_4''$, where $R_4''$ is hydrogen or $C_{1-2}$alkyl, and most preferably $R_4'''$, where $R_4'''$ is hydrogen or methyl, especially $R_4''''$, where $R_4''''$ is hydrogen or 3-methyl.

$R_5$ is preferably $R_5'$, where $R_5'$ is hydrogen, $C_{1-2}$alkyl, fluoro or chloro, more preferably $R_5''$, where $R_5''$ is hydrogen or fluoro, and most preferably $R_5'''$, where $R_5'''$ is hydrogen or 4-fluoro.

$R_6$ is preferably $R_6'$, where $R_6'$ is hydrogen or $C_{1-2}$alkyl, more preferably $R_6''$, where $R_6''$ is hydrogen or methyl, and most preferably $R_6'''$, where $R_6'''$ is hydrogen or 5-methyl.

Preferably, not more than one of $R_4$ and $R_5$ is a member of the group consisting of t-butyl, trifluoromethyl, phenoxy and benzyloxy. More preferably, no two of $R_4$ ($R_4'$, $R_4''$, etc.), $R_5$ ($R_5'$, $R_5''$, etc.) and $R_6$ ($R_6'$, $R_6''$, etc.) are ortho to each other unless at least one member of each pair of substituents that are ortho to each other is a member of the group consisting of hydrogen, $C_{1-2}$alkyl, $C_{1-2}$alkoxy, fluoro and chloro.

The preferred $R_4$-bearing phenyl groups are phenyl, 4-fluorophenyl, 3,4- and 3,5-dimethylphenyl, 4-fluoro-3-methylphenyl and 3,5-dimethyl-4-fluorophenyl, with 4-fluorophenyl and 3,5-dimethylphenyl being more preferred.

Preferably, each $R_7$ is $C_{1-3}$alkyl or both $R_7$'s taken together are $-(CH_2)_q-$; more preferably, each $R_7$ is $C_{1-2}$alkyl or both $R_7$'s taken together are $-(CH_2)_q-$; and most preferably each $R_7$ is $C_{1-2}$alkyl.

$R_{10}$ is preferably $R_{10}'$, where $R_{10}'$ is hydrogen or methyl, and more preferably hydrogen.

$R_{11}$ is preferably $R_{11}'$, where $R_{11}'$ is hydrogen, $R_{12}'$ or M, more preferably $R_{11}''$, where $R_{11}''$ is hydrogen, $C_{1-3}$alkyl or M, even more preferably $R_{11}'''$, where $R_{11}'''$ is hydrogen, $C_{1-2}$alkyl or M, and most preferably M, especially sodium.

$R_{12}$ is preferably $R_{12}'$, where $R_{12}'$ is $C_{1-3}$alkyl, n-butyl, i-butyl, t-butyl or benzyl, more preferably $C_{1-3}$alkyl, and most preferably $C_{1-2}$alkyl, especially ethyl.

X is preferably X', where X' is $-CH_2CH_2-$ or $(E)-CH=CH-$, and more preferably $(E)-CH=CH-$.

Z is preferably a group of Formula a or c wherein $R_{11}$ is $R_{11}'$ or a group of Formula b, more preferably a group of Formula a or c wherein $R_{11}$ is $R_{11}''$ or a group of Formula b, even more preferably a group of Formula a wherein $R_{11}$ is $R_1'''$ or a group of Formula b, and most preferably a group of Formula a wherein $R_{11}$ is M, especially sodium.

m is preferably m', where m' is 2, 3, 4 or 5, more preferably m'', where m'' is 2, 3 or 4, and most preferably m''', where m''' is 2 or 4, especially 4.

n is preferably 2.

M is preferably free from centers of asymmetry and is more preferably M', where M' is sodium, potassium or ammonium, and most preferably sodium. For simplicity, each formula in which M appears has been written as if M were monovalent and, preferably, it is. However, it may also be divalent or trivalent and, when it is, it balances the charge of two or three carboxy groups, respectively. Thus, Formula I and every other formula containing an M embraces compounds wherein M is divalent or trivalent, i.e., which contains two or three carboxylate-containing anions per cation M.

As between otherwise identical compounds of Formula I, those wherein Z is a group of Formula a or b are generally preferred over those wherein Z is a group of Formula c, with those wherein Z is a group of Formula a being generally preferred over those wherein Z is a group of Formula b.

Insofar as the compounds of Groups IAa and IBa and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IAb and IBb and each of the subgroups thereof are concerned, the trans lactones are generally preferred over the cis lactones, cis and trans referring to the relative positions of $R_{10}$ and the hydrogen atom in the 6-position of the group of Formula b.

The preferred stereoisomers of the compounds of Formula I having only two centers of asymmetry wherein X is —CH=CH— or —CH$_2$—CH=CH—, and Z is a group of Formula a are the 3R,5S and 3R,5R isomers and the racemate of which each is a constituent, i.e., the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of Formula I having only two centers of asymmetry wherein X is —(CH$_2$)$_n$— or —CH=CH—CH$_2$—, and Z is a group of Formula a are the 3R,5R and 3R,5S isomers and the racemate of which each is a constituent, i.e., the 3R,5R-3S,5S (erythro) and 3R,5S-3S,5R (threo) racemates, with the 3R,5R isomer and the racemate of which it is a constituent being more preferred and the 3R,5R isomer being most preferred.

The preferred stereoisomers of the compounds of Formula I having only two centers of asymmetry wherein X is —CH=CH— or —CH$_2$—CH=CH—, and Z is a group of Formula b are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I having only two centers of asymmetry wherein X is —(CH$_2$)$_n$— or —CH=CH—CH$_2$—, and Z is a group of Formula b are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

The preferences set forth in the preceding four paragraphs also apply to the compounds of Groups IAa, IAb, IBa and IBb having more than two centers of asymmetry and represent the preferred configurations of the indicated positions.

The preferred stereoisomers of the compounds of Formula I having just one center of asymmetry wherein Z is a group of Formula c are the 3R isomer and the racemate of which it is a constituent, i.e., the 3R-3S racemate, with the 3R isomer being more preferred. These preferences also apply to the compounds of Groups IAc and IBc having more than one center of asymmetry and represent the preferred configuration of the indicated position.

Each of the preferences set forth above applies, not only to the compounds of Formula I, but also to the compounds of Groups IAa, IAb, IAc, IBa, IBb and IBc as well as to every subgroup thereof set forth in the specification, e.g., Groups (i) et seq., unless otherwise indicated. When any preference contains a variable, the preferred significances of that variable apply to the preference in question, unless otherwise indicated.

Preferred groups of compounds of Formula I include the compounds (i) of Group IAa wherein $R_o$ is $R_o'$, especially $R_o''$, R is R', $R_1$ is $R_1'$, $R_2$ is $R_2'$, $R_3$ is $R_3'$, $R_{10}$ is $R_{10}'$, $R_{11}$ is $R_{11}'$, and X is X', (ii) of (i) wherein $R_o$ is $R_o''$, $R_{10}$ is hydrogen, $R_{11}$ is $R_{11}''$, and X is (E)—CH=CH—, (iii) of (ii) wherein $R_o$ is $R_o'''$, R is R'', $R_1$ is $R_1''$, $R_2$ is $R_2''$, $R_3$ is hydrogen, and $R_{11}$ is $R_{11}'''$, particularly M, (iv) of (iii) wherein $R_o$ is $R_o''''$ wherein $R_4'''$ is $R_4''''$, R is $C_{1-2}$alkyl, $R_1$ is $C_{1-2}$alkyl, and $R_2$ is hydrogen, (v) of (iv) wherein $R_{11}$ is M, particularly M', and especially sodium, (vi) of Group IAb wherein $R_o$ is $R_o'$, especially $R_o''$, R is R', $R_1$ is $R_1'$, $R_2$ is $R_2'$, $R_3$ is $R_3'$, $R_{10}$ is $R_{10}'$, and X is X', (vii) of (vi) wherein $R_o$ is $R_o''$, $R_{10}$ is hydrogen, and X is (E)—CH=CH—, (viii) of (vii) wherein $R_o$ is $R_o'''$, R is R'', $R_1$ is $R_1''$, $R_2$ is $R_2''$, and $R_3$ is hydrogen, (ix) of (viii) wherein $R_o$ is $R_o''''$ wherein $R_4'''$ is $R_4''''$, R is $C_{1-2}$alkyl, $R_1$ is $C_{1-2}$alkyl and $R_2$ is hydrogen, (x) of Group IBa wherein $R_o$ is $R_o'$, especially $R_o''$, R and $R_1$ taken together are —(CH$_2$)$_m$—, $R_2$ is $R_2'$, $R_3$ is $R_3'$, $R_{10}$ is $R_{10}'$, $R_{11}$ is $R_{11}'$, and X is X', (xi) of (x) wherein $R_o$ is $R_o''$, $R_{10}$ is hydrogen, $R_{11}$ is $R_1''$, and X is (E)—CH=CH—, (xii) of (xi) wherein $R_o$ is $R_o'''$, $R_2$ is $R_2''$, $R_3$ is hydrogen, $R_{11}$ is $R_1'''$, particularly M, and m is m', (xiii) of (xii) wherein $R_o$ is $R_o''''$ wherein $R_4'''$ is $R_4''''$, $R_2$ is hydrogen, and m is m'', (xiv) of (xiii) wherein $R_{11}$ is M, particularly M', and especially sodium, (xv) of Group IBb wherein $R_o$ is $R_o'$, especially $R_o''$, R and $R_1$ taken together are —(CH$_2$)$_m$—, $R_2$ is $R_2'$, $R_3$ is $R_3'$, $R_{10}$ is $R_{10}'$, and X is X', (xvi) of (xv) wherein $R_o$ is $R_o''$, $R_{10}$ is hydrogen, and X is (E)—CH=CH—, (xvii) of (xvi) wherein $R_o$ is $R_o'''$, $R_2$ is $R_2'$, $R_3$ is hydrogen, and m is m', (xviii) of (xvii) wherein $R_o$ is $R_o''''$ wherein $R_4'''$ is $R_4''''$, $R_2$ is hydrogen, and m is m'', (xix)-(xxviii) of (i)-(v) and (x)-(xiv) wherein the hydroxy groups in the 3- and 5-positions of the group of Formula a have the erythro configuration, (xxix)-(xxxvi) of (vi)-(ix) and (xv)-(xviii) wherein $R_{10}$ and the hydrogen atom in the 6-position of the group of Formula b are trans to each other, i.e., the trans lactones, (xxxvii) of Group IAc wherein $R_o$ is $R_o'$, especially $R_o''$, R is R', $R_1$ is $R_1'$, $R_2$ is $R_2'$, $R_3$ is $R_3'$, each $R_7$ is $C_{1-3}$alkyl or the two $R_7$'s taken together are —$(CH_2)_q$—, $R_{10}$ is $R_{10}'$, $R_{11}$ is $R_{11}'$, and X is X', with the provisos that $R_{11}$ may be hydrogen only when Q is —CO—, and X may be —$CH_2CH_2$— only when $R_{10}$ is methyl, (xxxviii) of (xxxvii) wherein $R_o$ is $R_o''$, each $R_7$ is $C_{1-2}$alkyl or the two $R_7$'s taken together are —$(CH_2)_q$—, $R_{10}$ is hydrogen, $R_{11}$ is $R_{11}''$, and X is (E)—CH=CH—, (xxxix) of (xxxviii) wherein $R_o$ is $R_o'''$, R is R'', $R_1$ is $R_1''$, $R_2$ is $R_2''$, $R_3$ is hydrogen, each $R_7$ is $C_{1-2}$alkyl, and $R_{11}$ is $R_{11}'''$, particularly M, (xl) of (xxxix) wherein $R_o$ is $R_o''''$ wherein $R_4'''$ is $R_4''''$, R is $C_{1-2}$alkyl, $R_1$ is $C_{1-2}$alkyl, and $R_2$ is hydrogen, (xli) of (xl) wherein $R_{11}$ is M, particularly M', and especially sodium, (xlii) of Group IBc wherein $R_o$ is $R_o'$, especially $R_o''$, R and $R_1$ taken together are —$(CH_2)_m$—, $R_2$ is $R_2'$, $R_3$ is $R_3'$, each $R_7$ is $C_{1-3}$alkyl or the two $R_7$'s taken together are —$(CH_2)_q$—, $R_{10}$ is $R_{10}'$, $R_{11}$ is $R_{11}'$, and X is X', with the provisos that $R_{11}$ may be hydrogen only when Q is —CO—, and X may be —$CH_2CH_2$— only when $R_{10}$ is methyl, (xliii) of (xlii) wherein $R_o$ is $R_o''$, each $R_7$ is $C_{1-2}$alkyl or the two $R_7$'s taken together are —$(CH_2)_q$—, $R_{10}$ is hydrogen, $R_{11}$ is $R_{11}''$, and X is (E)—CH=CH—, (xliv) of (xliii) wherein $R_o$ is $R_o'''$, $R_2$ is $R_2''$, $R_3$ is hydrogen, each $R_7$ is $C_{1-2}$alkyl, $R_{11}$ is $R_{11}''$, particularly M, and m is m', (xlv) of (xliv) wherein $R_o$ is $R_o''''$0 wherein $R_4'''$ is $R_4''''$, $R_2$ is hydrogen, and m is m'', (xlvi) of (xlv) wherein $R_{11}$ is M, particularly M', and especially sodium, and (xlvii)-(lvi) of (xxxvii)-(xlvi) wherein Q is —CO—.

Groups (i)-(xviii) and (xxxvii)-(lvi) embrace each of the possible stereoisomers, racemates and mixtures of diastereoisomers. Groups (xix)-(xxviii) embrace the 3R,5S and 3S,5R isomers and the 3R,5S-3S,5R racemate of the compounds wherein X is (E)—CH=CH— having just two centers of asymmetry and the corresponding compounds having more than two centers of asymmetry, and Groups (xix) and (xxiv) also embrace the 3R,5R and 3S,5S isomers and the 3R,5R-3S,5S racemate of the compounds wherein X is —$CH_2CH_2$— having just two centers of asymmetry and the corresponding compounds having more than two centers of asymmetry. Groups (xxix)-(xxxvi) embrace the 4R,6S and 4S,6R isomers and the 4R,6S-4S,6R racemate of the compounds wherein X is (E)—CH=CH— having just two centers of asymmetry and the corresponding compounds having more than two centers of asymmetry, and Groups (xxix) and (xxxiii) also embrace the 4R,6R and 4S,6S isomers and the 4R,6R-4S,6S racemate of the compounds wherein X is —$CH_2CH_2$— having just two centers of asymmetry and the corresponding compounds having more than two centers of asymmetry.

The compounds of Formula I may be synthesized as follows:

REACTION SCHEME I

The compounds of Formula I wherein X is —$(CH_2)_n$— or (E)—CH=CH—, and Z is a group of Formula a wherein $R_{10}$ is hydrogen and $R_{11}$ is $R_{12}'$ may be synthesized by the following series of reactions:

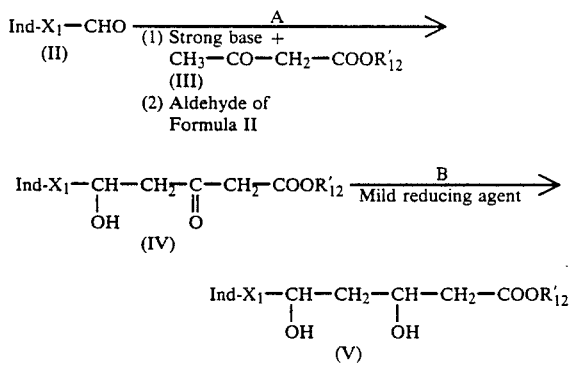

REACTION SCHEME II

The compounds of Formula I wherein X is —$(CH_2)_n$— or (E)—CH=CH—, and Z is a group of Formula a wherein $R_{10}$ is $C_{1-3}$alkyl and $R_{11}$ is $M_2^\oplus$ may be synthesized by the following series of reactions:

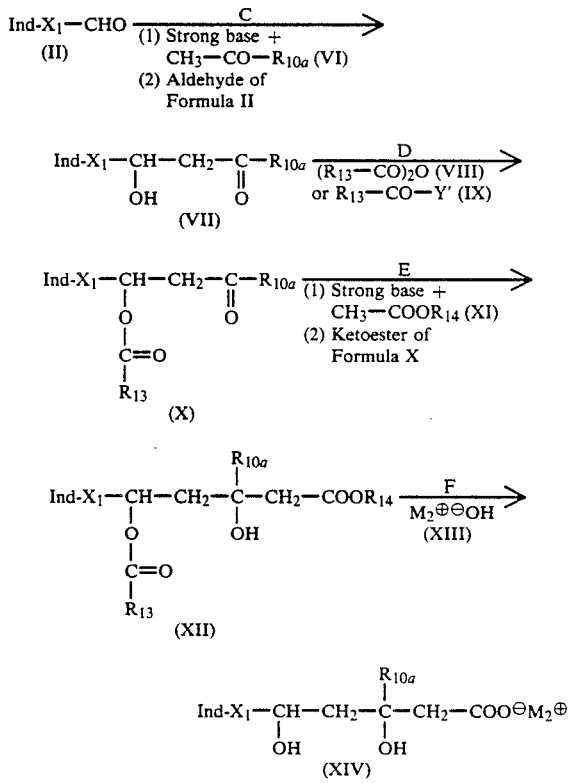

REACTION SCHEME III

The compounds of Formula I wherein X is —$CH_2CH_2$—, —$CH_2CH_2CH_2$—, —CH=CH—, —CH=CH—$CH_2$— or, —$CH_2$—CH=CH—, and Z is a group of Formula a wherein $R_{11}$ is $R_{12}'$ may be synthesized by the following series of reactions:
Formula b having the 4R,6S configuration or X is —$CH_2CH_2$— or —$CH_2CH_2CH_2$—, and Z is a group of
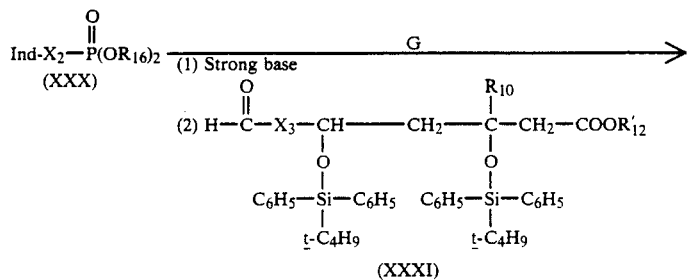
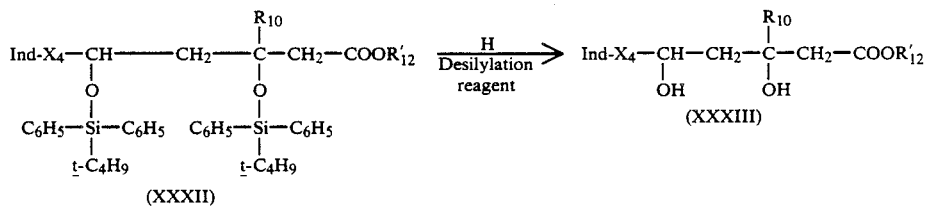
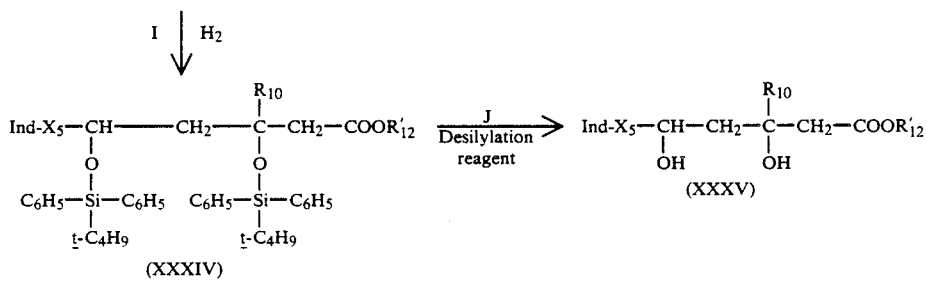
REACTION SCHEME IV
The compounds of Formula I wherein X is —CH=CH— or —$CH_2$—CH=CH—, and Z is a group of
Formula b having the 4R,6R configuration may be synthesized by the following series of reactions:
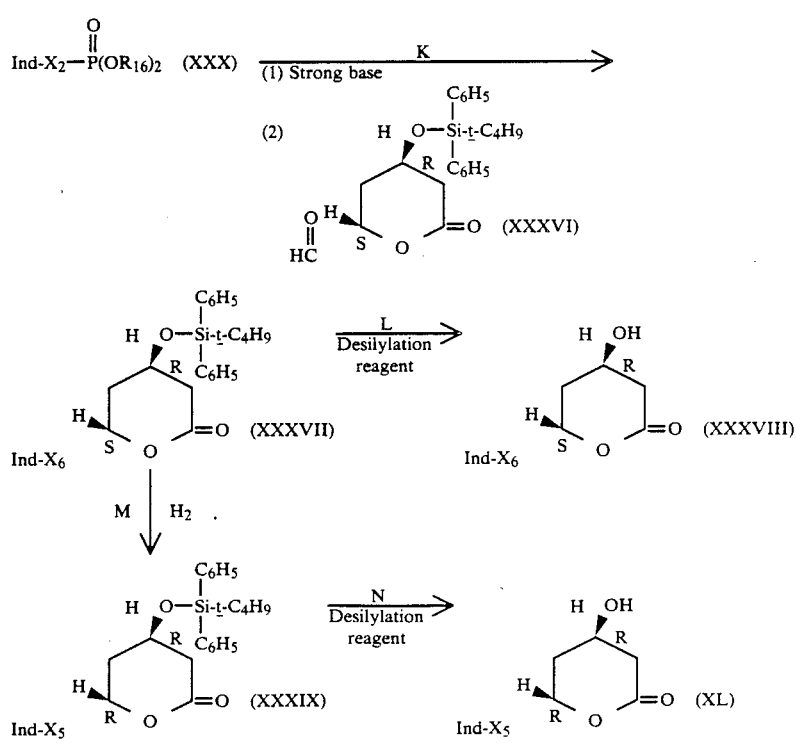

REACTION SCHEME V
The compounds of Formulae V, XIV, etc. may be converted into the corresponding compounds of Formula I wherein Z has a different significance of Formula a or b by the following series of reactions:
REACTION SCHEME VI
The compounds of Formula I wherein Z is a group of Formula c may be synthesized by the following series of reactions:
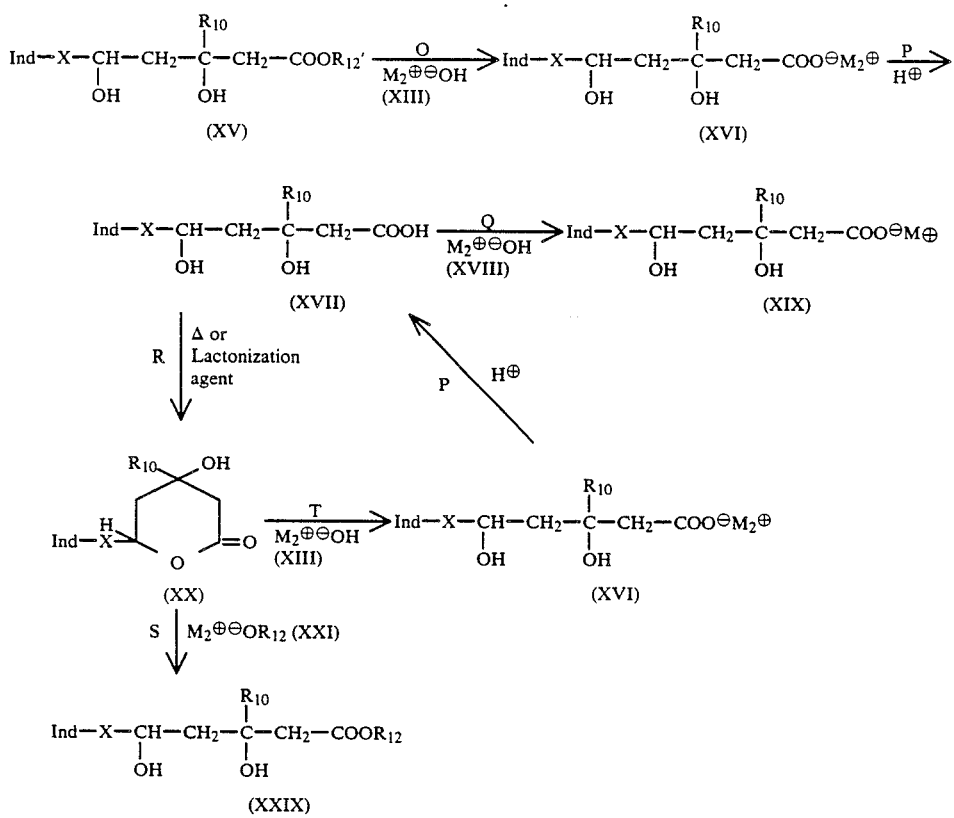
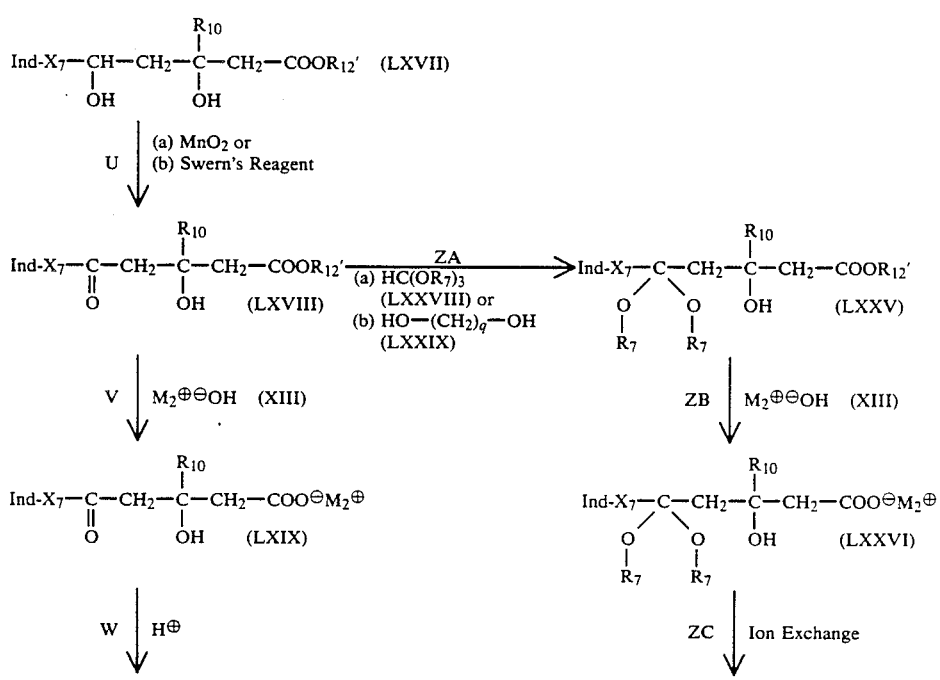

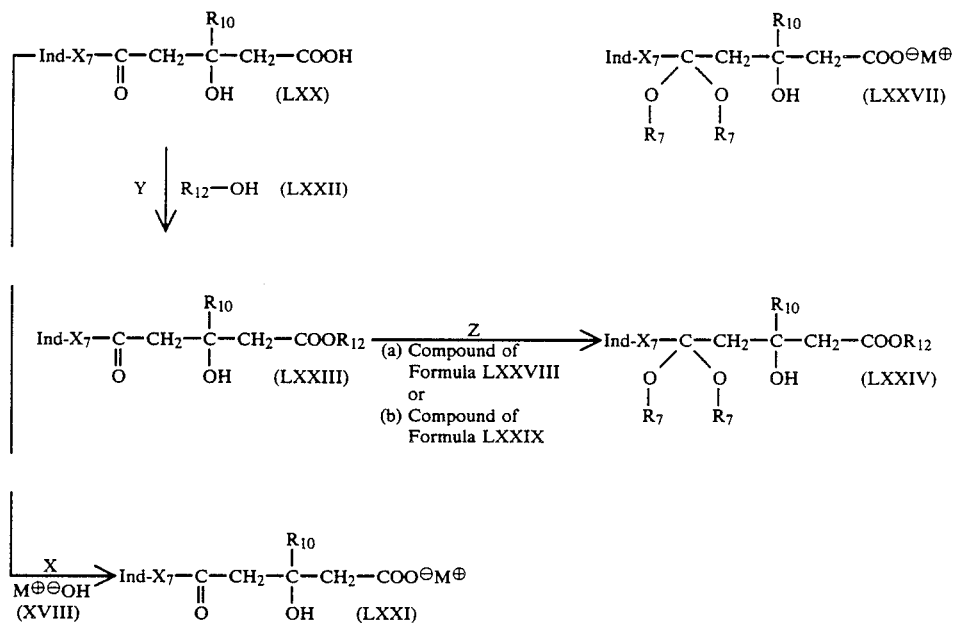
REACTION SCHEME VII
The compounds of Formula II may be synthesized by the following series of reactions:
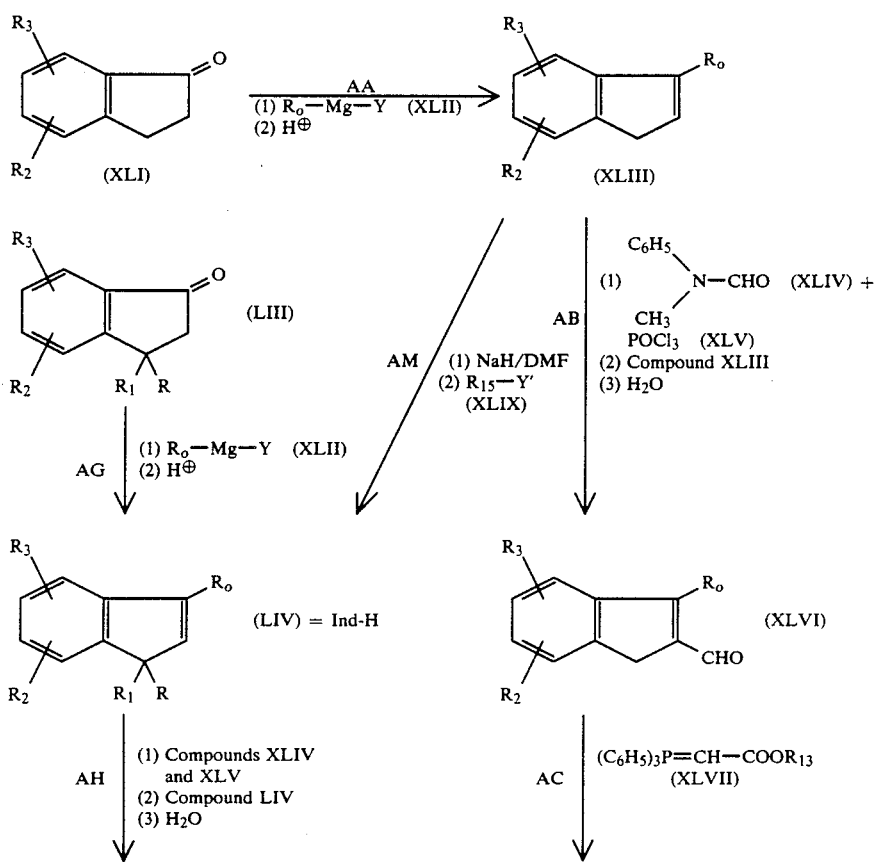

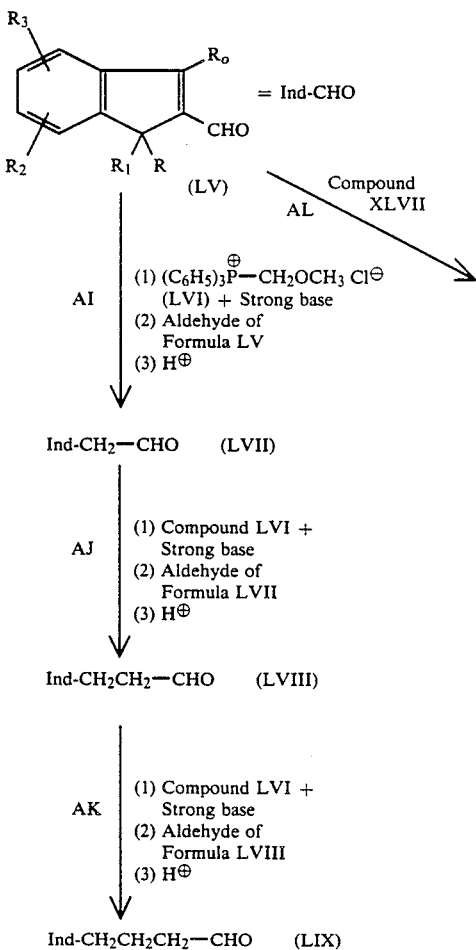
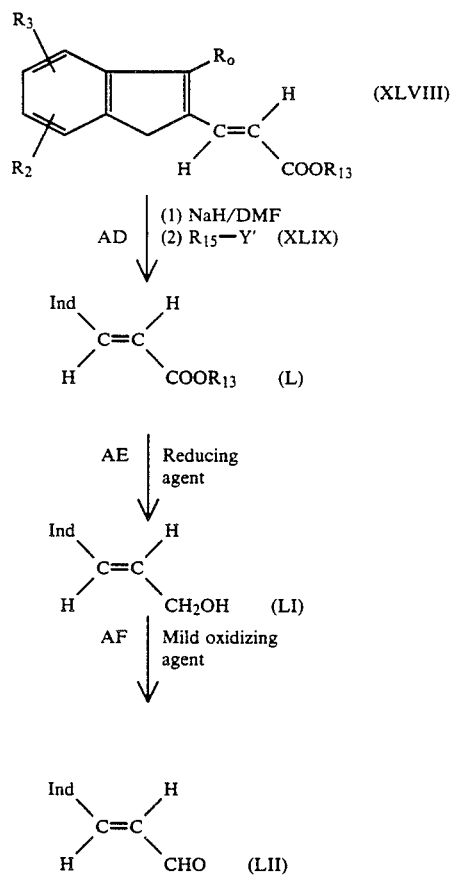
REACTION SCHEME VIII
The compounds of Formula XXX may be synthesized by the following series of reactions:
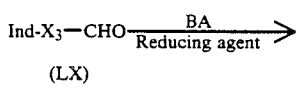
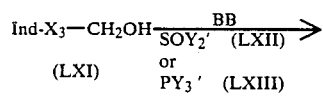
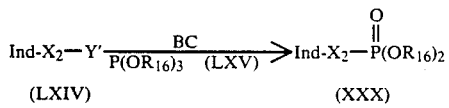
REACTION SCHEME IX
The compounds of Formula XXXI may be synthesized by the following series of reactions:
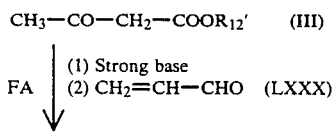
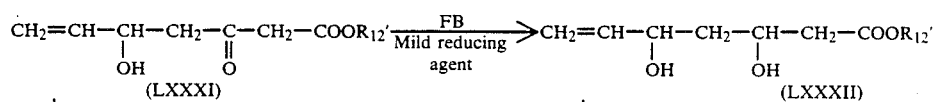
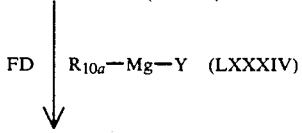
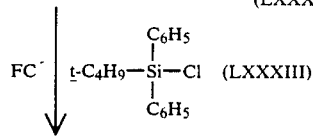

-continued

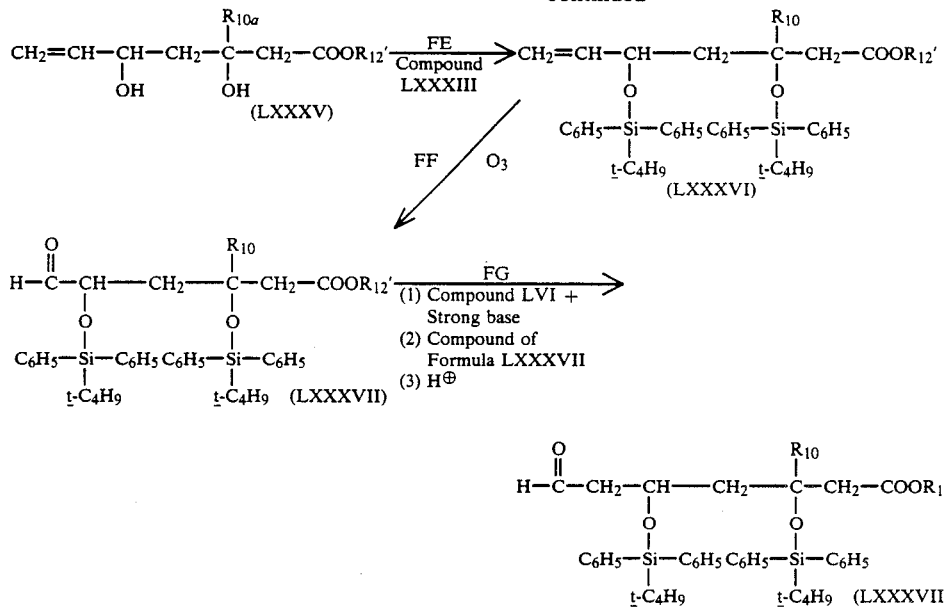

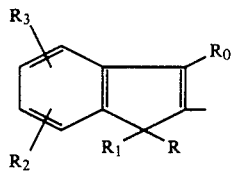

In the foregoing reaction schemes, Ind is

[structure of indene with R0, R1, R2, R3, R]

wherein $R_o$-$R_3$ are as defined above, $R_{10a}$ is $C_{1-3}$alkyl, $R_{13}$ is $C_{1-2}$ alkyl, preferably methyl, $R_{14}$ is $C_{1-3}$ alkyl, n-butyl or t-butyl, preferably ethyl or t-butyl, $R_{15}$ is $R_1'$, —$(CH_2)_m$-Y' or (Z)—$CH_2$—CH=CH—$CH_2$—Y', wherein $R_1$ and m are as defined above, and Y' is as defined below, each $R_{16}$ is independently $C_{1-2}$alkyl, the two $C_{1-2}$alkyl groups preferably being the same, $X_1$ is —$(CH_2)_n$— or (E)—CH=CH—, especially (E)—CH=CH—, wherein n is 1, 2 or 3, $X_2$ is —$CH_2$— or —$CH_2CH_2$—, $X_3$ is a direct bond or —$CH_2$—, $X_4$ is —CH=CH—, —CH=CH—$CH_2$— or —$CH_2$—CH=CH—, preferably (E)—CH=CH—, (E)—CH=CH—$CH_2$— or (E)—$CH_2$—CH=CH— and especially (E)—CH=CH—, $X_5$ is —$CH_2CH_2$— or —$CH_2CH_2CH_2$—, especially —$CH_2CH_2$—, $X_6$ is —CH=CH— or —$CH_2$—CH=CH—, preferably —CH=CH— and especially (E)—CH=CH—, $X_7$ is —$(CH_2)_n$—, —CH=CH—, —$CH_2$—CH=CH— or —CH=CH—$CH_2$ when $R_{10}$ is $C_{1-3}$alkyl and is —CH=CH— or —$CH_2$—CH=CH— when $R_{10}$ is hydrogen, wherein n is 1, 2 or 3, Y is chloro, bromo or iodo, Y' is chloro or bromo, $M_2^{\oplus}$ is sodium or potassium, and each of the other variables is as defined above.

| Reaction/Type | Reagents, Molar Ratios and Comments | Temperature | Time | Solvent | Inert Atmosphere |
|---|---|---|---|---|---|
| A | (1) Generation of dianion of III: 1 mole III and 2-2.2 equivalents strong base, pref. 1-1.1 moles sodium hydride then 1-1.1 moles n-butyllithium or 2-2.2 moles lithium diisopropylamide. | −50°-10° C., pref. −30°-5° C. | 0.3-1.5 hrs. | AIO, e.g., ES, pref. THF | Yes |
| | (2) 1-2.5 moles, pref. 1.2-2.2 moles, more pref. 1.3-2.0 moles, of dianion of III (assuming 100% conversion of III to its dianion) per mole II. Product (IV) is racemic. | −80°-0° C., pref. −60°-0° C., more pref. −30°-−10° C. | 0.3-4 hrs., pref. 0.3-2 hrs. | Same as Step 1 | Yes |
| | (3) Quench with, for example, ammonium chloride solution or 1 N. hydrochloric acid. | −80°-25° C. | 1-5 min. | Same as Step 1 | |
| B (Reduction) | (a) Non-stereoselective: 1-4, pref. 2-4, equivalents of transferable hydride per mole IV, pref. sodium borohydride or complex of t-butylamine and borane. When a racemic IV is utilized, product (V) is a mixture of all four possible stereoisomers (the erythro and threo racemates) wherein the ratio of the erythro stereoisomers to the threo stereoisomers ranges from 3:2 to 2:3. | −10°-30° C. | 1-8 hrs. | IO, e.g., lower alkanol, esp. ethanol | Yes |

-continued

| Reaction/Type | Reagents, Molar Ratios and Comments | Temperature | Time | Solvent | Inert Atmosphere |
|---|---|---|---|---|---|
| | (b) Stereoselective: | | | | |
| | (1) 1-1.3 moles, pref. 1.02-1.3 moles, tri-(primary or secondary $C_{2-4}$alkyl)borane, pref. triethylborane, and, pref., 0.3-8 liters, e.g., 0.75-6.5 liters, air (at 25° C. and 760 mm. Hg.) per mole IV. | 0°-50° C., pref. 0°-25° C. | 0.5-6 hrs., pref. 1-3.5 hrs. | AIO, pref. ES, esp. THF, or pref., mixture of THF and methanol, more pref. a 3-4:1 mixture | Yes |
| | (2) 0.4-3.5 moles, pref. 1.5-2.5 moles, sodium borohydride per mole IV. After the reaction, quench the reaction mixture with, for example, 1 N. hydrochloric acid at −78°-−20° C. and isolate the crude product by extracting with a suitable inert organic solvent (e.g., diethyl ether) and evaporating the solvent at reduced pressure. It is pref. to crystallize the cyclic boron ester, if possible. If the reaction mixture is quenched with water instead of acid, product of this step may be a mixture containing the boron ester and a compound of Formula XVI. | −100°-−40° C., pref. −100°-−70° C. | 2-48 hrs., pref. 16-48 hrs. | Same as Step 1 | Yes |
| | (3) large excess of anhydrous methanol, e.g., 50-500 moles per mole IV, or a mixture of methanol (e.g., 10-20 l. per mole IV), hydrogen peroxide (e.g., 4-8 l. of 30% aqueous hydrogen peroxide per mole IV), and a pH 7-7.2 aqueous phosphate buffer (pref. 6-10 l. of a pH 7 aqueous phosphate buffer (e.g., 0.054 M. sodium, 0.024 M. potassium and 0.047 M. phosphate) per mole IV). The amount of buffer must be sufficient to maintain a pH of 7-7.2. Dissolve product of Step 2 in methanol and add buffer and aqueous hydrogen peroxide. See Narasaka et al., Tetrahedron 40, 2233-2238 (1984). | 20°-40° C., pref. 20°-25° C., with methanol alone and −30°-25° C., pref. −10°-10° C., with a mixture of methanol, hydrogen peroxide and buffer | 0.7-60 hrs., pref. 4-60 hrs., with methanol alone and 0.5-2 hrs. with a mixture of methanol, hydrogen peroxide and buffer | Neat | — |
| | (c) Alternative Stereoselective: | | | | |
| | (1) 1-5 moles zinc borohydride (pref. as 0.1-0.2 M. solution in anhydrous diethyl ether produced as described in Gensler et al., J. Am. Chem. Soc. 82, 6074-6081 (1960) per mole IV. | −80°-−50° C., pref. −80°-−70° C. | 0.5-5 hrs., pref. 1-4 hrs. | AIO, pref. ES, esp. diethyl ether or mixture of diethyl ether with another ES | Yes |
| | (2) Add excess methanol (e.g., 10-100 moles per mole IV) and allow to slowly warm to 20°-25° C. | −80°-−50° C., pref. −80°-−70° C.,→20°-25° C. | 1-2 hrs. | Same as Step 1 | |
| | (3) Add excess dilute aqueous acetic acid to quench the reaction mixture. Can also add the dilute acetic acid at −80°-−50° C. and then allow to warm to 20°-25° C. When a racemic IV is utilized in Alternative b or c, product (V) is a mixture of the four possible stereoisomers wherein the ratio of the erythro isomers (racemate) to the threo isomers (racemate) is about 4-20:1, usually 5-15:1, except as noted below. Repeated recrystallization of the cycloc boron ester produced in Step 2 of Alternative b, if a solid, may raise the ratio or even yield pure erythro racemate and mother liquors enriched with threo racemate. When, however, the solvent in Step 1 of Alternative b is a mixture of THF and methanol, said ratio may be as high as 50-100:1. | 20°-25° C. | — | Same as Step 1 | — |
| C | (1) Generation of monoanion of VI: 1-1.1 equivalents strong base, pref. lithium diisopropylamide, per mole VI. | −80°-−40° C., pref. −80°- | 0.25-1.5 hrs. | AIO, e.g., ES, pref. THF | Yes |
| | (2) 1-4 moles, pref. 3 moles, of monoanion of VI (assuming 100% conversion of VI to its monoanion) per mole II. | −80°-−40° C., pref. −80°-−75° C. | 0.25-1.5 hrs. | Same as Step 1 | Yes |
| | (3) Quench with, for example, ammonium | −80°-25° C. | 1-5 min. | Same as Step 1 | — |

-continued

| Reaction/Type | Reagents, Molar Ratios and Comments | Temperature | Time | Solvent | Inert Atmosphere |
|---|---|---|---|---|---|
| | chloride solution. | | | | |
| D (Acylation) | 1-3 moles, pref. 2 moles, VIII or IX per mole VII. When an ES is used as the solvent, also use 1-4 moles, pref. 2.5-3 moles, of a tertiary amine, e.g., pyridine or, pref., 4-dimethylaminopyridine, per mole VII. | −10°-50° C., pref. 20°-30° C. | 2-18 hrs., pref. 4-12 hrs. | Pyridine or anhydrous ES, pref. THF | Yes |
| E | (1) Generation of monoanion of XI: 1-1.1 equivalents strong base, pref. lithium diisopropylamide, per mole XI. | −80°-0° C. | 0.25-1 hr. | AIO, e.g., ES, pref. THF | Yes |
| | (2) 1-4 moles, pref. 3 moles, or monoanion of XI (assuming 100% conversion of XI to its monoanion) per mole X. | −80°--40° C., pref. −80°-−70° C. | 0.25-1.5 hrs. | Same as Step 1 | Yes |
| | (3) Quench with, for example, ammonium chloride solution. | −80°-25° C. | 1-5 min. | Same as Step 1 | — |
| F (Hydrolysis) | 2-2.3 moles, pref. 2-2.2 moles, XIII per mole XII. | 0° C.-reflux, pref. 0°-75° C., esp. 20°-50° C. | 1-4 hrs. | Inert aqueous organic, e.g., mixture of water and lower alkanol, pre. mixture of water and methanol or, esp., ethanol | — |
| G (Wittig) | (1) 1-1.2 moles strong base, pref. n-butyl-lithium or lithium diisopropylamide (or complex thereof, e.g., lithium diisopropylamide · monotetrahydrofuran) and, optionally, 1.75-2 moles lithium chloride per mole XXX. Add strong base to other reactant(s). | −20°-0° C. | 0.5-1.5 hrs. | AIO, pref. ES, esp. THF | Yes |
| | (2) 1-1.2 moles XXXI per mole XXX used in Step 1. | −20°-0° C. | 0.3-12 hrs. | Same as Step 1 | Yes |
| | (3) Quench with, e.g., saturated ammonium chloride solution. Product (XXXII) is a mixture of the (Z) and (E) (cis and trans, respectively) isomers which may be separated by chromatography. Only a very small amount of the (Z) isomer is produced as a general rule. | −20°-25° C. | 1-5 min. | — | — |
| H (Deprotection) | 2-12 moles, pref. 4-8 moles, fluoride reagent, esp. tetra-n-butylammonium fluoride, per mole XXXII and 0.5-2 moles, pref. 1.2-1.5 moles, glacial acetic acid per mole fluoride reagent. Pref., first add glacial acetic acid to solution of XXXII, then add fluoride reagent. | 20°-60° C. | 2-120 hrs. | AIO, e.g., ES, pref. THF, or mixture of ES, pref. THF, and acetonitrile | — |
| I (Hydrogenation) | Excess hydrogen (more than 1 mole per mole XXXII) and catalytic amount of platinum dioxide (e.g., 1-5 g. per mole XXXII). Initial hydrogen pressure is conveniently 30-60 p.s.i. | 20°-25° C. | Until 1 mole hydrogen per mole XXXII is taken up | Lower alkanol, e.g., ethanol | — |
| J (Deprotection) | Same as Reaction H (Molar quantities are per mole XXXIV). | Same as H | Same as H | Same as H | — |
| K (Wittig) | Same as Reaction G. (Reactant in Step 2 is XXXVI). Product (XXXVII) is a mixture of the (Z) and (E) (cis and trans, respectively) isomers which may be separated by chromatography. Only a very small amount of the (Z) isomer is produced as a general rule. | Same as G | Same as G | Same as G | Yes |
| L (Deprotection) | Same as Reaction H except utilize 1-4 moles, pref. 2-4 moles, fluoride reagent per mole XXXVII. | Same as H | Same as H | Same as H | — |
| M (Hydrogenation) | Same as Reaction I (Molar quantities are per mole XXXVII). | Same as I | Same as I | Same as I | — |
| N (Deprotection) | Same as Reaction H except utilize 1-4 moles, pref. 2-4 moles, fluoride reagent per mole XXXIX. | Same as H | Same as H | Same as H | — |
| O (Hydrolysis) | 1-1.3 equivalents XIII per mole XV or, if it is desired to isolate XVI, pref. 0.95-0.995 equivalent XIII per mole XV. | 0° C.-reflux, pref. 0°-75° C., esp. 0°-25° C. | 0.5-4 hrs. | Inert equeous organic, e.g., mixture of water and lower alkanol, pref. mixture of water and methanol or, | — |

-continued

| Reaction/Type | Reagents, Molar Ratios and Comments | Temperature | Time | Solvent | Inert Atmosphere |
|---|---|---|---|---|---|
| P (Acidification) | At least 1 equivalent, e.g., 1–1.25 equivalents, acid, e.g., 2 N. hydrochloric acid, per mole XVI. | 0°–25° C. | 1–5 min. | esp., ethanol Water or mixture of water and water-miscible inert organic solvent e.g., methanol, ethanol, diethyl ether or THF | — |
| Q (Neutralization) | 0.95–0.99 equivalent, pref. 0.96–0.98 equivalent, XVIII per mole XVII. | 0°–25° C., pref. 20°–25° C. | 2–10 min. | Same as O | — |
| R (Lactonization) | (a) Use of catalytic amount of a strong acid such as p-toluenesulfonic acid monohydrate is optional but usually omit. Use of Dean-Stark trap is pref. if solvent forms azeotrope with water. | 75° C.-reflux, pref. 75°–150° C., esp. 80°–120° C. | 3–18 hrs., pref. 4–7 hrs. | AIO, pref. HC, e.g., benzene, toluene or xylene or mixture thereof | — |
| | (b) 1–1.5 moles of a lactonization agent, e.g., a carbodiimide, pref. a water-soluble carbodiimide such as N-cyclohexyl-N'-[2'-(N''-methylmorpholinium)ethyl]-carbodiimide p-toluenesulfonate, per mole XVII. Alternative b often results in higher yields of XX than Alternative a. Racemic erythro XVII yields racemic trans (lactone) XX, racemic threo XVII yields racemic cis (lactone) XX, mixture of racemic erythro and threo XVII yields mixture of racemic trans and cis (lactones) XX, and single enantiomer of XVII yields single enantiomer of XX, e.g., 3R, 5S erythro XVII yields 4R, 6S trans XX. | 10°–35° C., pref. 20°–25° C. | 2–8 hrs., pref. 3–4 hrs. | AIO, pref. HLA, esp. methylene chloride | — |
| S (Esterification) | At least 2 moles, e.g., 2–10 moles, pref. 2.05–2.5 moles, XXI per mole XX. Racemic trans (lactone) XX yields racemic erythro XXII, racemic cis (lactone) XX yields racemic threo XXII, mixture of racemic trans and cis (lactones) XX yields mixture of racemic erythro and threo XXII, and single enantiomer of XX yields single enantiomer of XXII, e.g., 4R, 6S trans XX yields 3R, 5S erythro XXII. | 0°–70° C., pref. 0°–25° C. when $R_{12}$ is primary alkyl | 1–12 hrs., pref. 1–3 hrs. when $R_{12}$ is primary alkyl | AIO, e.g., ES such as THF or alcohol of the formula $R_{12}$—OH ($R_{12}$ must be same as in XXI), if a liquid | — |
| T (Hydrolysis) | 1–1.3 equivalents XIII per mole XX or, if it is desired to isolate XVI, 0.94–1 equivalent, preferably 0.97–0.99 equivalent, XIII per mole XX. Racemic trans (lactone) XX yields racemic erythro XVI, racemic cis (lactone) XX yields racemic threo XVI, mixture of racemic trans and cis (lactones) XX yields mixture of racemic erythro and threo XVI, and single enantiomer of XX yields single enantiomer of XVI, e.g., 4R, 6S trans XX yields 3R, 5S erythro XVI. | 0° C.-reflux, pref. 0°–75° C., more pref. 20°–75° C. | 0.5–6 hrs., pref. 1–4 hrs. | Same as O | — |
| U (Oxidation) | (a) When X is —CH═CH— or —CH₂—CH═CH—: 5–50 moles manganese dioxide (pref. activated) per mole LXVII. | 20°–80° C., pref. 40°–80° C. | 1–4 days | AIO, pref. ES or HC, esp. toluene | Yes |
| | (b) When X is —(CH$_2$)$_n$— or —CH═CH—CH$_2$—: | | | | |
| | (1) Preparation of Swern's Reagent: 0.9596 l. oxalyl chloride and 1.561 l. dimethyl sulfoxide per mole LXVII to be used in Step 2. | −20°–0° C. | 5–15 min. | Neat | Yes |
| | (2) Swern's Reagent from Step 1 and 6.969 l. triethylamine per mole LXVII. | −60°– −40° C., pref. −50° C. | 1–6 hrs. | Methylene chloride | Yes |
| V (Hydrolysis) | Same as Reaction O (Molar quantities are per mole LXVIII). | Same as O | Same as O | Same as O | — |
| W (Acidification) | Same as Reaction P (Molar quantities are per mole LXIX). | Same as P | Same as P | Same as P | — |
| X (Neutralization) | Same as Reaction Q (Molar quantities are per mole LXX). | Same as Q | Same as Q | Same as Q | — |
| Y (Esterification) | 1–5 moles LXXII and catalytic amount of acid, e.g., p-toluenesulfonic acid · monohydrate, per mole LXX. When reaction is run neat, use large excess of LXXII, e.g., 50–100 | 20°–40° C. | 1–6 hrs. | AIO, e.g., ES such as THF or neat (if LXII is a liquid) | — |

| Reaction/ Type | Reagents, Molar Ratios and Comments | Temperature | Time | Solvent | Inert Atmosphere |
|---|---|---|---|---|---|
| Z (Ketalization) | moles, per mole LXX. (a) When each $R_7$ is $C_{1-6}$alkyl not containing an asymmetric carbon atom: 3-5 moles LXXVIII and catalytic amount of pyridinium p-toluenesulfonate per mole LXXIII. | 20°-25° C. | 24-72 hrs. | AIO, e.g., HLA or HC, esp. methylene chloride or benzene | Yes |
| | (b) When the two $R_7$'s taken together are $-(CH_2)_q-$: 2-3 moles LXXIX and catalytic amount (e.g., 1-3 g.) of pyridinium p-toluenesulfonate per mole LXXIII. | 20°-25° C. | 24-72 hrs. | Same as Alternative a | Yes |
| ZA (Ketalization) | Same as Reaction Z (Molar quantities are per mole (LXVIII). | Same as Z | Same as Z | Same as Z | Yes |
| ZB (Hydrolysis) | Same as Reaction O (Molar quantities are per mole LXXV). | Same as O | Same as O | Same as O | — |
| ZC (Ion Exchange) | Utilize an ion exchange resin such as Amberlite IR-P64 having the desires $M^{\oplus}$ ions by the conventional procedure, e.g., dissolve LXXVI in water, load onto ion exchange resin column and elute with appropriate buffer. | 20°-25° C. | — | — | — |
| AA (Grignard + Dehydration) | (1) Formation of Grignard Reagent: 0.95-1.2 moles magnesium turnings, trace of iodine and, optionally, small amount of 1,2-dibromoethane or methyl iodide per mole $R_o$-Y (XLIIA). Add magnesium turnings to solution of other reactants or, pref., solution of XLIIA to other reactants, in either case at a rate such that the reaction mixture refluxes gently. | 10° C.-reflux, pref. 30°-38° C. in diethyl ether and 35°-65° C. in THF | Until magnesium completely or nearly completely dissolves, e.g., 0.5- 4 hrs. | Anhydrous inert ES, esp. THF or diethyl ether | Yes |
| | (2) Reaction of Grignard Reagent: 1-1.7 moles, pref. 1-1.25 moles, XLII per mole XLI. | 20°-25° C. | 1-18 hrs., usually 1-3 hrs. | Same as Step 1 | Yes |
| | (3) Dehydration: Dissolve hydroxy group-containing product of Step 2 in glacial acetic acid, e.g., 0.3-1.5 l. per mole XLI, and heat. Alternatively, can add a cooled mixture of saturated ammonium chloride solution and concentrated hydrochloric acid, e.g., 0.5-1 l. of the former and 0.1-0.25 l. of the latter per mole LXI, to the product of Step 2 and stir the resulting two phase mixture. | 90° C.-reflux, pref. 100° C.-reflux, esp. 110° C.-reflux, with glacial acetic acid and 0°-25° C. with aqueous acid | 0.25-2 hrs., pref. 0.5- 1.5 hrs. | Neat | — |
| AB (Vilsmeier-Haack) | (1) Formation of iminium salt: 1 mole XLIV per mole XLV. Reaction can be run neat or can use excess XLIV or acetonitrile as solvent. | 0°-35° C., pref. 20°-25° C. | 5-45 min., pref. 20-40 min. | Acetonitrile or neat | Yes |
| | (2) Reaction of iminium salt with XLIII: 1-1.25 moles iminium salt per mole XLIII. Usually add solution of XLIII in acetonitrile to product (iminium salt) of Step 1. Pref., mix reactants at 10° C. and then allow to warm to 20°-25° C. | 10°-30° C., pref. 10° C.→20°-25° C. | 3-24 hrs., usually 6-16 hrs. | Acetonitrile or neat | Yes |
| | (3) Hydrolysis: Excess water of dilute sodium hydroxide solution. Generally, Steps 1 and, especially, 2 are faster when run neat, and the more dilute the reaction mixture, the longer the reaction time. However, when the reaction is run neat, the reaction mixture tends to solidify when stirred. Therefore, the reaction mixture should not be stirred if the reaction is run neat, and it is often necessary or desirable to utilize a solvent, particularly in Step 2. | 0°-25° C. | 1-10 min. | Water | — |
| AC (Wittig) | 1-1.3 moles XLVII per mole XLVI. | 50°C.-reflux, pref. 60°-115° C., esp. 90°-115° C. | 3-8 hrs., pref. 4-8 hrs. | AIO, pref. ES, e.g., THF, or HC, e.g., toluene, esp. toluene | Yes |
| AD (Alkylation) | (1) Generation of mono- or di-carbanion: For L wherein R is hydrogen and $R_1$ is aklyl: 0.99-1.02 moles sodium hydride (e.g., as 50%-80% dispersion in mineral oil) per mole XLVIII. For L wherein R and $R_1$ are identical and are alkyl or where R and $R_1$ taken together are | −5°-5° C., pref. 0° C. | 8-45 min. | AIO, pref. dimethylformamide or THF optionally containing a small amount of oil (from the so- | Yes |

-continued

| Reaction/Type | Reagents, Molar Ratios and Comments | Temperature | Time | Solvent | Inert Atmosphere |
|---|---|---|---|---|---|
| | $-(CH_2)_m-$ or (Z)-$CH_2-CH=CH-CH_2-$: 2-3 moles sodium hydride (e.g., as 50%-80% dispersion in mineral oil) per mole XLVIII. | | | dium hydride) | |
| | (2) Reaction of mono- or di-carbanion: For L wherein R is hydrogen and $R_1$ is aklyl or R and $R_1$ taken together are $-(CH_2)_m-$ or (Z)-$CH_2-CH=CH-CH_2-$: 1-1.05 moles XLIX per mole XLVIII used in Step 1. For L wherein R and $R_1$ are identical and are alkyl: 2-2.1 moles XLIX per mole XLVIII used in Step 1. Generally, add XLIX neat or dissolved in the solvent to the product of Step 1 stirred at $-5°-5°$ C. and then allow the reaction mixture to gradually warm to 20°-25° C. To synthesize L wherein R and $R_1$ are different alkyl groups, utilize this reaction to synthesize L wherein R is hydrogen and $R_1$ is alkyl and then repeat this reaction utilizing said compound in lieu of XLVIII and an XLIX having a different $R_{15}$. | $-5° \rightarrow 25°$ C. | 4-18 hrs., pref. 5-12 hrs. | Same as Step 1 | Yes |
| AE (Reduction) | Strong metal hydride reducing agent, e.g., lithium aluminum hydride or diisobutylaluminum hydride. At least 2 equivalents, pref. 2.5-5 equivalents, of transferable hydride per mole L, e.g., at least 0.5 mole, pref. 1-1.25 moles, lithium aluminum hydride or at least 2 moles, preferably 2.5-5 moles, diisobutylaluminum hydride per mole L. | $-80°-25°$ C., pref. $-80°-0°$ C., esp. $-80°-$ $-50°$ C. | 0.3-4 hrs. | AIO, pref. ES, e.g., THF, HLA, esp. methylene chloride, or mixture of HLA and toluene | Yes |
| AF (Oxidation) | 5-50 moles, pref. 7-25 moles, manganese dioxide (pref. activated) per mole LI. | 20°-80° C., pref. 20°-25° C. | 2-72 hrs., pref. 12-48 hrs. | IO, pref. HLA, esp. methylene chloride, or HC, esp. toluene | — |
| AG (Grignard) | Same as Reaction AA (Molar quantities in Step 2 are per mole LIII). | Same as AA | Same as AA | Same as AA | Yes |
| AH (Vilsmeier-Haack) | Same as Reaction AB except use in Step 2 1-5 moles iminimum salt per mole LIV. | Same as AB except 25°-82° C., pref. 75°-82° C., in Step 2 | Same as AB except 32-96 hrs. in Step 2 | Same as AB | Yes |
| AI (Wittig) | (1) Synthesis of ylide: 1-1.05 moles strong base, e.g., sodium hydride, phenyllithium or, pref., n-butyllithium per mole LVI. Pref., slowly add solution of strong base to solution of LVI. | $-40°-0°$ C., pref. $-35°-$ $-20°$ C. | 1-4 hrs. | AIO, pref. ES, e.g., THF | Yes |
| | (2) Synthesis of enol ether: Ylide from 1-1.05 moles LVI per mole LV. | $-30°-0°$ C., pref. $-20°-0°$ C. | 1-4 hrs. | Same as Step 1 | Yes |
| | (3) Hydrolysis of enol ether: Large molar excess, e.g., 2-20 moles, strong acid, e.g., 70% perchloric acid, per mole LV used in Step 2. | 0°-30° C. | 8-24 hrs. | Mixture of aqueous acid and ES, e.g., mixture of 70% perchloric acid and THF | — |
| AJ (Wittig) | Same as Reaction AI (Molar quantities in Steps 2 and 3 are per mole LVII). | Same as AI | Same as AI | Same as AI | Same as AI |
| AK (Wittig) | Same as Reaction AI (Molar quantities in Steps 2 and 3 are per mole LVIII). | Same as AI | Same as AI | Same as AI | Same as AI |
| AL (Wittig) | Same as Reaction AC (Molar quantities are per mole LV). | Same as AC | 8-24 hrs., pref. 12-24 hrs. | Same as AC | Yes |
| AM (Alkylation) | Same as Reaction AD (Molar quantities are per mole XLIII). | Same as AD | Same as AD | Same as AD | Yes |
| BA (Reduction) | 1-5 equivalents, pref. 2-4.5 equivalents, of transferable hydride per mole LX, pref. sodium borohydride or complex of t-butylamine and borane. | $-10°-30°$ C. | 1-24 hrs. | IO, e.g., lower alkanol, esp. ethanol, or mixture of ES and lower alkanol | |
| BB (Halogenation) | 1-2 moles, pref. 1.3-1.8 moles, LXII or LXIII per mole LXI. | $-10°-80°$ C. | 2-18 hrs. | AIO, pref. ES, e.g., diethyl ether or THF, HLA, e.g., methylene chloride, or HC, e.g., | — |

-continued

| Reaction/Type | Reagents, Molar Ratios and Comments | Temperature | Time | Solvent | Inert Atmosphere |
|---|---|---|---|---|---|
| BC | 1–1.1 moles LXV per mole LXIV. Can use excess LXV as the solvent. | 20°–140° C., usually 100°–140° C. | 6–24 hrs., usually 10–16 hrs. | benzene HC, e.g., benzene or xylene or neat (excess LXV is solvent) | Yes |
| FA | (1) Generation of dianion of III: 1 mole III and 2–2.2 equivalents strong base, e.g., 2–2.2 moles lithium diisopropylamide or, pref., 1–1.1 moles sodium hydride followed by 1–1.1 moles n-butyllithium. | −50°–10° C., pref. −10°–10° C. | 0.3–1.5 hrs., pref. 0.5–1 hr. | AIO, e.g., ES, pref. THF | Yes |
|  | (2) 1–1.2 moles dianion of III (assuming 100% conversion of III to its dianion) per mole LXXX. Slowly add solution of LXXX in, pref., dry THF to solution of dianion stirred at −80°–0° C., pref. −40°–−20° C., esp. −35°–−30° C., stir at same temperature for 30 min. and allow to warm to 20°–25° C. over a 2 hr. period. | −30°–0° C., pref. −40°–−20° C., esp. −35°–−30° C., →20°–25° C. | 2.4 hrs. | Same as Step 1 | Yes |
|  | (3) Quench with, for example, saturated ammonium chloride solution. Product (LXXXI) is a racemate. | −80°–25° C. | 1–5 min. | — | — |
| FB (Reduction) | (a) Non-stereoselective: Same as Reaction B, Alternative a (Molar quantities are per mole LXXXI). Product (LXXXII) is a mixture of all four possible stereoisomers (the erythro and threo racemates), the erythro to threo ratio being approximately 3:2 to 2:3. | Same as B, a | Same as B, a | Same as B, a | Yes |
|  | (b) Stereoselective: |  |  |  |  |
|  | (1) 1–1.25 moles, pref. 1.05–1.25 moles, esp. 1.2–1.25 moles, tri-(primary or secondary C$_2$–$_4$alkyl)borane, pref. triethylborane or tri-n-butylborane, esp. the latter, per mole LXXXI. Use of air as in Step 1 of Alternative b of Reaction B is optional. | 0°–50° C., pref. 20°–25° C. | 1–6 hrs., pref. 1.5–3 hrs. | AIO, pref. ES, esp. THF, or mixture of THF and methanol, pref. a 3–4:1 mixture | — |
|  | (2) 0.4–1.5 moles, pref. 1–1.25 moles, sodium borohydride per mole LXXXI. After the reaction, reaction mixture is quenched with, for example, 10% hydrochloric acid and crude product is isolated by extraction with, for example, diethyl ether and evaporation of the solvent. | −100°–−40° C., pref. −90°–−70° C., esp. −90°–−78° C. | 2–60 hrs., pref. 24–48 hrs. | Same as Step 1 | — |
|  | (3) Large excess of methanol (e.g., 50–100 moles per mole LXXXI) or mixture of methanol (e.g., 10–20 l. per mole LXXXI), hydrogen peroxide (e.g., 4–8 l. 30% aqueous hydrogen peroxide per mole LXXXI) and a pH 7–7.2 aqueous phosphate buffer (pref. 6–10 l. of a pH 7 aqueous phosphate buffer (e.g., 0.054 M. sodium, 0.024 M. potassium and 0.047 M. phosphate) per mole LXXXI). The amount of buffer must be sufficient to maintain a pH of 7–7.2. Dissolve product of Step 2 in methanol and add buffer and aqueous hydrogen peroxide. Use of methanol alone is preferred. | 0°–25° C., pref. 0°–10° C., when using a mixture of methanol, hydrogen peroxide and buffer and 20°–60° C. when using methanol alone | 0.7–5 hrs., pref. 2–4 hrs. | As indicated | — |
| FC (Silylation) | 2–8 moles, pref. 4 moles, LXXXIII per mole LXXXII and 2 moles imidazole per mole LXXXIII. Slowly add LXXXIII to solution of LXXXII and imidazole (at rate such that temperature does not exceed 30° C.) and stir at, pref., 20°–25° C. for balance of reaction time. | 20°–30° C., pref. 20°–25° C. | 16–19 hrs. | Dry dimethylformamide | Yes |
| FD (Grignard) | (1) 1.8–2.1 moles, pref. 2 moles, LXXXIV per mole LXXXI. | −70°–25° C., pref. −50°–0° C. | 1–15 hrs., pref. 2–8 hrs. | AIO, pref. ES, esp. THF | Yes |
|  | (2) Quench with, for example, saturated ammonium chloride solution. | −20°–25° C. | 5–15 min. | — | — |
| FE (Silylation) | Same as Reaction FC (Molar quantities of LXXXIII are per mole LXXXV). | Same as FC | Same as FC | Same as FC | Yes |
| FF (Ozon- | Excess ozone. Bubble ozone through solution of LXXXVI until a bluish coloration persists | −80°–−70° C., pref. −78° C. | 2–30 min. | C$_1$–$_3$alkanol, esp. methanol, |  |

| Reaction/Type | Reagents, Molar Ratios and Comments | Temperature | Time | Solvent | Inert Atmosphere |
|---|---|---|---|---|---|
| olysis) | and then quench reaction mixture with dimethyl sulfide or triphenylphosphine. | | | or HLA, esp. methylene chloride, or ethyl acetate | |
| FG (Wittig) | Same as Reaction AI (Molar quantities are per mole LXXXVII). | Same as AI | Same as AI | Same as AI | Yes |

In the preceding table,

AIO=anhydrous inert organic solvent

ES=ether solvent, for example, diethyl ether, 1,2-diethoxyethane, 1,2-dimethoxyethane, tetrahydrofuran and mixtures thereof esp.=especially HC=hydrocarbon solvent, for example, benzene, toluene, xylene and mixtures thereof HLA=halogenated lower alkane solvent, for example, carbon tetrachloride, chloroform, 1,1-di-chloroethane, 1,2-dichloroethane, methylene chloride and 1,1,2-trichloroethane, usually preferably methylene chloride hr. (hrs.)=hour(s)

IO=inert organic solvent min.=minutes pref.=preferably, preferred

THF=tetrahydrofuran

Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually dry nitrogen, helium, neon, argon or krypton, or a mixture thereof, and most often dry nitrogen, to maintain anhydrous conditions. Most reactions, including those where the use of an inert atmosphere is not specified, are carried out under an inert atmosphere, usually dry nitrogen, for convenience.

In the preceding table, n-butyllithium is preferably employed as a 1.3–1.7M. solution in hexane, and lithium diisopropylamide is preferably prepared in situ from n-butyllithium and diisopropylamine.

Reactions analogous to Reactions A-F, H, J, L, N-T, V-Y, ZB, AE, AF, AI-AK, BA and BB are described in detail in copending application Ser. No. 06/722,288, filed by Faizulla G. Kathawala on April 11, 1985 and titled Indole Analogs of Mevalonolactone and Derivatives Thereof. These reactions may be carried out analogously to, for example, Reactions A-N, R-T, Z and BB-HH of said application. Said application, particularly pages 14–21, 28–30, 33–42, 44–47, 65–76, 82–100, 106, 107 and 116–122 thereof, is hereby incorporated by reference. Generally, where the reaction conditions set forth in said application differ from those set forth in this specification, the reaction conditions set forth in said application may also be utilized for the compounds of this specification. See also U.S. Pat. No. 4,739,073.

Reactions FA-FC and FF are described in further detail in U.S. Pat. No. 4,650,890. Columns 9-11 of said patent are hereby incorporated by reference.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

As is evident to those in the art, each of the compounds of Formulae I wherein Z is a group of Formula c (including those of Formulae LXVIII-LXXI, LXXIII-LXXVII, etc.), IV, VII, X and LXXXI has a single center of asymmetry provided that R and $R_1$, if present, are identical or taken together are $—(CH_2)_m—$ or $(Z)—CH_2—CH=CH—CH_2—$ and, therefore. may be resolved into two optically active isomers. When a compound of Formula IV, X or LXXXI is converted into a compound of Formula V, XII or LXXXII or LXXXV, respectively, an additional center of asymmetry is generated. Consequently, when a racemic compound Of Formula IV, X or LXXXI is utilized, four stereoisomers (two pairs of diastereoisomers) of the resulting compound of Formula V, XII or LXXXII or LXXXV are formed, whereas when an optically pure compound of Formula IV, X or LXXXI is utilized, two diastereoisomers of the compound of Formula V, XII or LXXXII or LXXXV are formed, provided, of course, that R and $R_1$, if present, are identical or taken together are $-(CH_2)_m-$ or $(Z)-CH_2-CH=CH-CH_2-$ and that the synthesis is not stereospecific.

The compounds of Formulae I wherein Z is a group of Formula a or b (including those of Formulae V, XIV-XVII, XIX, XX, XXII, LXVII, etc.), XII, XXXI, XXXII, XXXIV, LXXXII, LXXXV-LXXXVIII, etc. have at least two centers of asymmetry and, therefore, may exist in four or more stereoisomeric forms. Except where the compound is formed from an optically pure precursor already having each chiral carbon atom or where the reaction involves the use of a stereospecific reagent that gives an optically pure product, the compound is obtained as a mixture of two (if formed from an optically pure compound having one center of asymmetry), four (if formed from a racemic compound having one center of asymmetry), etc. stereoisomers.

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XX wherein R and $R_1$ are identical or taken together are $-(CH_2)_m-$ or $(Z)-CH_2-CH=CH-CH_2-$ may, for example, be separated by HPLC into its cis and trans (lactone) components, each of which is a racemate that may be resolved into two optically active enantiomers Techniques for resolving a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and-/or HPLC. For example, a racemic lactone of Formula XX may be reacted with an excess of R-(+)-α-methylbenzylamine (or the corresponding S-(−) compound) to form a mixture of two diastereoisomeric $_\alpha$-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°-25° C. for 16-24 hours. The reaction is run neat, with the excess amine serving as the solvent After the reaction, the excess amine is removed by vacuum distillation at 25°-35° C. After separation, each chiral amide may be hydrolyzed to the corresponding, for example, sodium, salt by, for example, refluxing with 1.5-3, preferably 2-2.2, equivalents of a base such as sodium hydroxide for 5-25 hours in a mixture of water and ethanol. The resulting salts may be converted to the corresponding free acids, esters, lactones and other salts by conventional means such as the reactions set forth in Reaction Schemes V and VI. On the other hand, a racemic compound having at least one hydroxy group may be esterified with an optically pure carboxylic acid having at least one center of asymmetry to form a mixture of diastereoisomeric esters or it may be reacted with an equimolar amount of an optically pure trisubstituted silyl halide having an asymmetric silicon atom, e.g., (−)-α-naphthylphenylmethylchlorosilane (Sommer et al., J. Am. Chem. Soc. 80, 3271 (1958).), in, for example, the presence of 2 moles of imidazole per mole of the silyl halide in dry dimethylformamide at 20°-32° C. for 12-24 hours to form a mixture of two diastereoisomeric silyloxy compounds, which mixture may be separated by conventional techniques. For example, diastereoisomeric (−)-α-naphthylphenylmethylsilyl derivatives of a lactone of Formula XX may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, (−)-α-naphthylphenylmethylsilyl and other silyl groups may be cleaved by treatment with, for example, 1-4 moles of tetra-n-butylammonium fluoride per mole of the silyloxy compound and 1-2 moles, preferably 1.2-1.5 moles, of glacial acetic acid per mole of tetra-n-butylammonium fluoride at 20°-60° C., preferably 20°-25° C., for 2-30 hours, preferably 3-8 hours, in an anhydrous ether solvent, preferably tetrahydrofuran, the silyloxy compound being added to a solution of the other reactants.

The compounds of Formulae III, VI, VIII, IX, XI, XIII, XVIII, XXI, XLI-XLV, XLVII, XLIX, LIII, LIV, LVI, LXII, LXIII, LXV, LXXII, LXXVIII, LXXIX, LXXX, LXXXIII and LXXXIV and the reagents not designated by a Roman numeral are known or, if unknown, may be synthesized by processes analogous to those described in the literature for similar known compounds.

A preferred process for the synthesis of the erythro racemate of the compound of Formula LXXXVII wherein $R_{10}$ is hydrogen, and $R'_{12}$ is methyl is disclosed in Kapa, Tetrahedron Letters 25, 2435-2438 (1984). The other compounds of Formula LXXXVII wherein $R_{10}$ is hydrogen in racemic erythro form may be synthesized similarly See also U.S. Pat. No. 4,571,428. Said patent, particularly columns 3-10 thereof, is hereby incorporated by reference.

The preferred process for the synthesis of the 3R,5S enantiomer of the compound of Formula LXXXVII wherein $R_{10}$ is hydrogen and $R'_{12}$ is t-butyl is disclosed in U.S. Pat. No. 4,808,607, columns 63-69 of which are hereby incorporated by reference, U.S. Pat. No. 4,822,799, columns 31-38 of which are hereby incorporated by reference, and U.S. Pat. No. 4,870,199, column 1, lines 13-55, column 7, lines 10-66, column 9, line 1—column 19, line 16 and column 26, line 36—column 33, line 52 of which are hereby incorporated by reference. U.S. Pat. No. 4,870,199 also discloses the synthesis of other compounds of Formula LXXXVII wherein $R_{10}$ is hydrogen in 3R,5S enantiomeric form.

The compound of Formula XXXVI and its synthesis is disclosed in U.S. Pat. No. 4,613,610. Columns 19, 20 and 38-42 of said patent are hereby incorporated by reference.

Since any compound of Formula I wherein Z is a group of Formula a or c wherein $R_{11}$ is a cation other than M may be converted into the corresponding compound wherein $R_{11}$ is hydrogen, M or $R_{12}$ by the processes of Reaction Schemes V and VI, the compounds of Formula I wherein Z is a group of Formula a or c and $R_{11}$ is a pharmaceutically unacceptable cation are also within the scope of this invention since they are useful as intermediates. However, such compounds are not compounds of Formula I as utilized in this specification, except where indicated to the contrary.

Also within the scope of this invention are the intermediates of Formulae II, IV, VII, X, XII, XXXII, XXXIV, XXXVII, XXXIX, XLVIII, L-LII, LV, LVII-LXI and LXIV. The preferences for each variable are the same as those set forth for the compounds of Formula I, with the preferred groups of such compounds including those that correspond to Groups (i)-(xxxvi) to the extent consistent therewith.

The entire specification of grandparent application Ser. No. 06/677,917, particularly pages 1-8, 34-40 and 60-67, is hereby incorporated by reference, as if set forth herein in its entirety.

Besides having the utility set forth below, every compound of Formula I is useful as an intermediate in the synthesis of one or more other compounds of Formula I utilizing the reactions set forth in Reaction Schemes V and VI.

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following two tests:

Test A. In Vitro Microsomal Assay of HMG-CoA Reductase Inhibition:

200 μl. aliquots (1.08-1.50 mg./ml.) of rat liver microsomal suspensions, freshly prepared from male Sprague-Dawley rats (150-225 g. body weight), in Buffer A with 10 mmol. dithiothreitol are incubated with 10 μl. of a solution of the test substance in dimethylacetamide and assayed for HMG-CoA reductase activity as described in Ackerman et al., J. Lipid Res. 18, 408-413 (1977), the concentration of the test substance in the assay system being 0.0001-2,000 μmolar. In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reduction of the substrate, [$^{14}$C]HMG-CoA. [$^{3}$H]mevalonolactone is added as an internal reference. Inhibition of HMG-CoA reductase is calculated from the decrease in specific activity ([$^{14}$C/$^{3}$H]mevalonate) of test groups compared to controls.

Test B. In Vivo Cholesterol Biosynthesis Inhibition Test:

In vivo studies utilize male Wistar Royal Hart rats weighing 150±20 g. which have been kept for 7-10 days on an altered light cycle (6:30 A.M.-6:30 P.M. dark) housed two per cage and fed powdered Purina Rat Chow and water ad libitum. Three hours before the diurnal maximum of cholesterol synthesis at mid-dark, the rats are orally administered the test substance (e.g., 0.01-200 mg./kg. body weight) dissolved or as a suspension in 0.5% carboxymethylcellulose in a volume of 1 ml./100 g. body weight. Controls receive vehicle alone. One hour after receiving the test substance (or the vehicle alone), the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia, and the serum is separated by centrifugation.

Serum samples are saponified and neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculated in nCi (nanocuries) of 3β-hydroxysterol formed per 100 ml. of serum. Inhibition of 3β-hydroxysterol synthesis is calculated from the reduction in the nCi of 3β-hydroxysterols formed from test qroups compared to controls.

The following results were obtained:

| Test A: | |
|---|---|
| Example 2 | $IC_{50}$ = 0.005 μmolar |
| Example 2A | $IC_{50}$ = 0.003 μmolar |
| Example 7 | $IC_{50}$ = 0.15 μmolar |
| Example 8 | $IC_{50}$ = 0.007 μmolar |
| Example 17 | $IC_{50}$ = 4.7 μmolar |
| Example 20 | $IC_{50}$ = 0.53 μmolar |
| Example 24 | $IC_{50}$ = 0.019 μmolar |
| Compactin | $IC_{50}$ = 1.01 μmolar |
| Mevinolin | $IC_{50}$ = 0.14 μmolar |

$IC_{50}$ is the concentration of the test substance in the assay system calculated or observed to produce a 50% inhibition of HMG-CoA reductase activity.

| Test B: | |
|---|---|
| Example 2 | $ED_{50}$ = 0.07 mg./kg. |
| Example 2A | $ED_{50}$ = 0.02 mg./kg. |
| Example 8 | $ED_{50}$ = 0.31 mg./kg. |
| Example 24 | $ED_{50}$ = 0.71 mg./kg. |
| Compactin | $ED_{50}$ = 3.5 mg./kg. |
| Mevinolin | $ED_{50}$ = 0.38 mg./kg. |

$ED_{50}$ is the dose of the test substance calculated or observed to produce a 50% inhibition of 3β-hydroxysterol synthesis.

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and antiatherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means. The preferred pharmaceutical compositions from the stand-point of ease of preparation and administration are solid compositions, particularly tablets and capsules.

The precise dosage of the compound of Formula I to be employed for inhibiting cholesterol biosynthesis depends upon several factors including the host, the nature and the severity of the condition being treated, the mode of administration and the particular compound employed However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 0.01–100 mg./kg. body weight, e.g., 0.01–10 mg./kg. body weight for the more active compounds and 0.01–2.5 mg./kg. for the compounds of Examples 2, 2A and 8. For most larger primates, a suitable oral daily dosage is indicated to be 1–2,000 mg., preferably 1–150 mg., e.g., 1–30 mg., for the more active compounds. For the compounds of Examples 2, 2A and 8 it is indicated to be 1–30 mg., e.g., 1–10 mg. (1–4 mg. for the compound of Example 2A).

The daily dosage is usually divided into two to four equal portions or administered in sustained release form. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 0.25–500 mg. of a compound of Formula I. Preferred dosage units contain 0.25–5 mg. of a compound of Formula I such as the compounds of Examples 2, 2A and 8.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

Representative formulations suitable for encapsulation in a hard gelatin capsule by conventional techniques are:

| | |
|---|---|
| Compound of Formula I, e.g., the compound of Example 2 or 2A | 1 mg. |
| Corn starch | 248 mg. |
| Magnesium stearate | 1 mg. |

A representative formulation suitable for preparing tablets by conventional means is:

| | |
|---|---|
| Compound of Formula I, e.g., the compound of Example 8 | 2.5 mg. |
| Polyvinylpyrrolidone USP | 5 mg. |
| Powdered lactose | 181.5 mg. |
| Corn starch | 10 mg. |
| Magnesium stearate | 1 mg. |

The following examples show representative compounds encompassed by this invention and their synthesis. However, it should be understood that they are for purposes of illustration only.

EXAMPLE 1

Ethyl erythro-(E)-3,5-dihydroxy-7-[3'-(4''-fluorophenyl)-spiro[cyclopentane-1,1'(1H)-inden]-2'-yl]hept-6-enoate

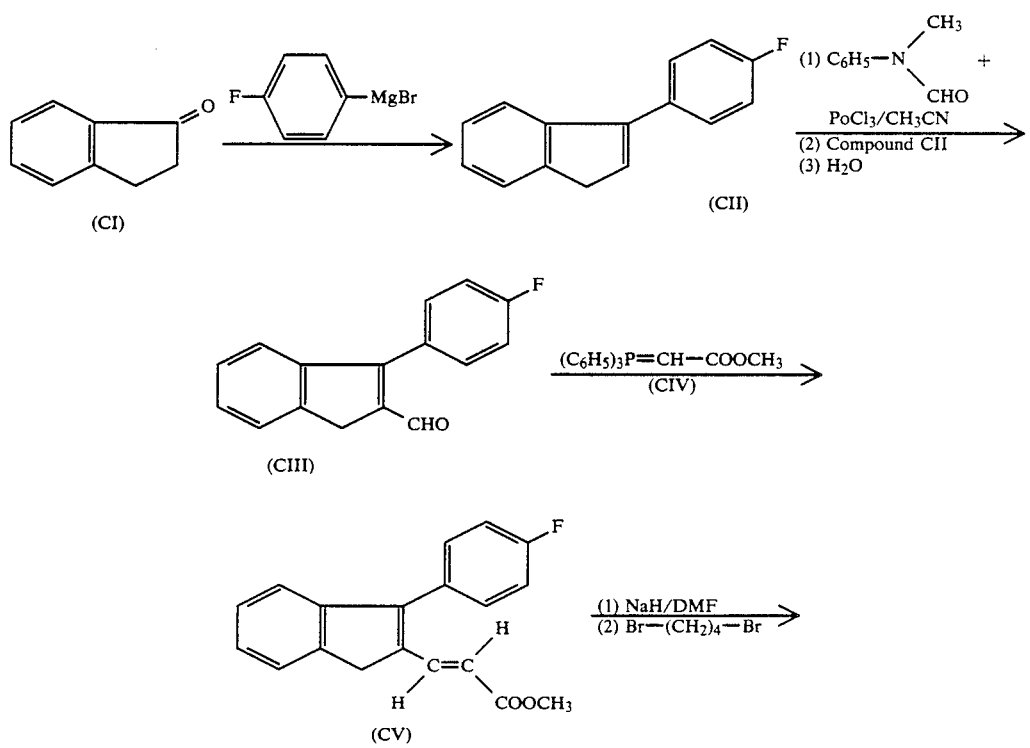

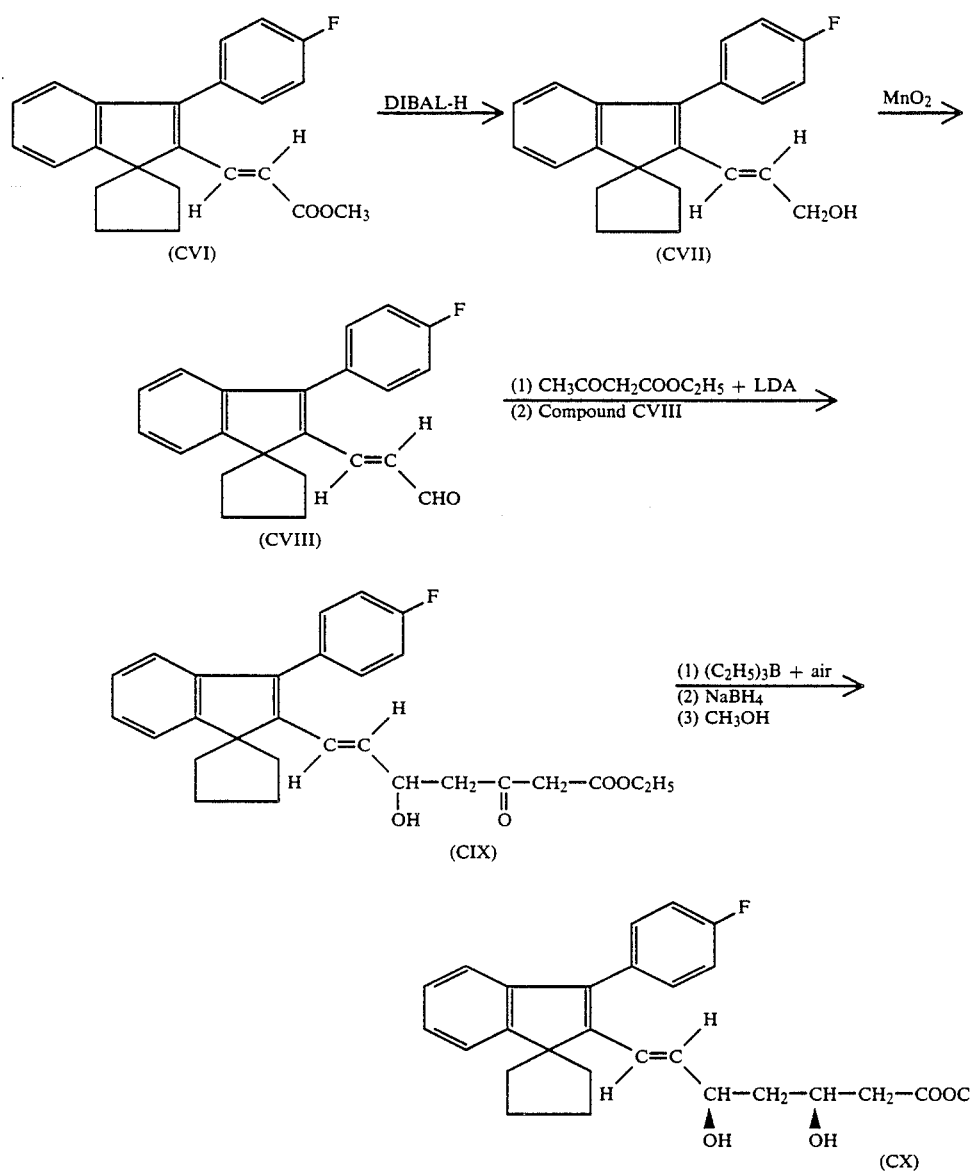

Step 1 (Reaction AA)

3-(4'-Fluororophenyl)-1H-indene (Compound CII)

A solution of 5.1 g. (39 mmoles) of 1-indanone in 15 ml. of anhydrous diethyl ether is added over a 30 minute period to a solution of 4-fluorophenylmagnesium bromide (prepared from 7.97 g. (45.5 mmoles) of 1-bromo-4-fluorobenzene, 1.33 g. (54.7 mmoles) of magnesium turnings and a trace of iodine in 25 ml. of anhydrous diethyl ether) stirred at 20°-25° C. under nitrogen. The reaction mixture is stirred at 20°-25° C. under nitrogen for 16 hours and quenched with saturated ammonium chloride solution. The organic phase is separated, dried over anhydrous sodium sulfate and evaporated at reduced pressure, and the residual oil (8.4 g.) is dissolved in 16 ml. of glacial acetic acid. The obtained solution is refluxed for 15 minutes, and the acetic acid is evaporated at reduced pressure. The residue is flash chromatographed on a silica gel column utilizing 10% ethyl acetate/petroleum ether as the eluant, and the eluant is evaporated at reduced pressure to obtain a solid (6.4 g.) which is recrystallized from 95% ethanol to obtain the product (3.6 g.), m.p. 35°-36° C.

First revised procedure

About 10 ml. (~15.9 g.; 0.091 mole) of 1-bromo-4-fluorobenzene is added to a mixture of 60 g. (2.47 moles) of magnesium turnings, about 50 mg. of iodine and 250 ml. of dry tetrahydrofuran stirred at 20°-25° C. under nitrogen during the course of which the temperature rises to about 40° C. A solution of 243 ml. (387.1 g., 2.21 moles) of 1-bromo-4-fluorobenzene in 750 ml. of dry tetrahydrofuran is added dropwise over a 2 hour period at a rate such that the reaction mixture refluxes gently, the reaction mixture is refluxed for 1 hour, cooled to 15° C. and added dropwise to a solution of 250 g. (1.89 moles) of 1-indanone in 500 ml. of dry tetrahydrofuran over a period of 1 hour, the temperature of the reaction mixture being 15°-30° C. during the addition, and the reaction mixture is stirred at 20°-25° C. for 16 hours, the reaction mixture being stirred under nitrogen throughout. The reaction mixture is poured into a cooled mixture of 1 l. of saturated ammonium chloride solution and 250 ml. of concentrated hydrochloric acid, the two phase mixture is stirred for 30 minutes, and the lower (aqueous) phase is separated and discarded. The organic phase is washed twice with 1 l. portions of saturated sodium chloride solution (until the washing is neutral) and concentrated at 45°-50° C. and reduced pressure to a volume of about 250 ml., 200 ml. of n-heptane is added, and the mixture is evaporated at 50° C. and reduced pressure to an oil. 800 ml. of methanol is added, the mixture is stored at 0° C. for 16 hours, and the resulting tan precipitate is collected by filtration, washed twice with 200 ml. portions of cold methanol and vacuum dried at 20°-25° C. to constant weight to obtain the product (255.5 g.), m.p. 38°-40° C. The mother liquor is concentrated to a volume of about 250 ml. and cooled, and the resulting precipitate is collected, washed twice with 50 ml. portions of cold methanol and vacuum dried to constant weight (72 g.), m.p. 35°-37° C. Total yield: 327.5 g. (82.4%).

Second revised procedure 10 ml. (15.93 g., 0.091 mole) of 1-bromo-4-fluorobenzene is added to a mixture of 60 g. (2.47 moles) of magnesium turnings, ~50 mg. of iodine and 250 ml. of tetrahydrofuran (dried over molecular sieves) stirred at 20°-25° C. under nitrogen and, when the reaction commences (the internal temperature rising to about 40° C. ), a solution of 243 ml. (387.1 g., 2.21 moles) of 1-bromo-4-fluorobenzene in 750 ml. of tetrahydrofuran (dried over molecular sieves) is added dropwise over a period of 2 hours while maintaining a gentle reflux (~70° C. internal temperature), the reaction mixture is refluxed for 1 hour and cooled to 15° C., a solution of 250 g. (1.89 moles) of 1-indanone in 500 ml. of tetrahydrofuran (dried over molecular sieves) is added dropwise over a period of 1 hour (the internal temperature being 15°-30° C. ), and the reaction mixture is stirred at 20°-25° C. for 16 hours, the reaction mixture being stirred under nitrogen throughout. The reaction mixture is cautiously poured into a cold mixture of 1 l. of saturated ammonium chloride solution and 250 ml. of concentrated hydrochloric acid (the addition being exothermic), the mixture is stirred for 30 minutes, the aqueous (lower) phase is discarded, and the organic phase is washed three times with 1 l. portions of saturated sodium chloride solution (until the washing is neutral) and concentrated at 45°-50° C. (external temperature) and reduced pressure to a volume of about 250 ml. 800 ml. of methanol is added, the resulting mixture is maintained at 0°-10° C. for 16 hours, stirred at −10°-0° C. and seeded, and the resulting solid is collected by filtration, washed with 200 ml. of cold methanol and vacuum dried at 20°-25° C. to obtain the product (275 g.), m.p. 39°-41° C. The mother liquor is concentrated, 200 ml. of methanol is added, the mixture is maintained at 0°-10° C. , and the resulting solid is collected by filtration and vacuum dried at 20°-25° C. to obtain a less pure second crop (57.5 g.), m.p. 33°-39° C.

Step 2 (Reaction AB)

3-(4'-Fluorophenyl)-1H-indene-2-carboxaldehyde (Compound CIII)

5 ml. of acetonitrile is added to a mixture of 0.973 ml. (10 mmoles) of phosphorus oxychloride and 1.3 ml. (10 mmoles) of N-methylformanilide stirred at 20°-25° C., the reaction mixture is stirred at 20°-25° C. for 30 minutes and cooled to 5° C., a solution of 2 g. (9.5 mmoles) of Compound CII in 5 ml. of acetonitrile is added dropwise with stirring, and the reaction mixture is stirred at 20°-25° C. for 6.5 hours, the reaction mixture being maintained under nitrogen throughout. The reaction mixture is poured onto ice and extracted several times with 4:1 diethyl ether/petroleum ether. The extracts are combined, washed with water, washed with saturated sodium chloride solution, dried over anhydrous sodium sulfate, passed through a short silica gel column and evaporated at reduced pressure to obtain the crude product as an oil (2.04 g.). The oil is dissolved in chloroform and flash chromatographed on a silica gel column, the eluant is evaporated at reduced pressure, and the residue is crystallized from petroleum ether to obtain the product (2.9 g.), m.p. 70°-71° C.

Revised procedure

A mixture of 26.6 ml. (43.8 g.; 285.4 mmoles) of phosphorus oxychloride and 35.2 ml. (38.5 g.; 285.1 mmoles) of N-methylformanilide is allowed to stand at 20°-25° C. for 30 minutes under nitrogen. The resulting yellow solution is cooled to 10° C., a solution of 50 g. (238 mmoles) of Compound CII in 120 ml. of acetonitrile is added dropwise, and the reaction mixture is stirred at 20°-25° C. for 16 hours, the reaction mixture being stirred under nitrogen throughout. The reaction mixture is poured into cold water, and the mixture is extracted twice with diethyl ether. The diethyl ether extracts are combined, washed with water, washed with saturated sodium chloride solution, dried over anhydrous sodium sulfate and evaporated at reduced pressure to obtain the crude product as a brown oil (57.5 g.).

Step 3 (Reaction AC)

Methyl (E)-3-[3'-(4''-fluorophenyl)-1H-inden-2'-yl]propenoate (Compound CV)

A solution of 573 mg. (2.42 mmoles) of Compound CIII and 1.01 g. (2.91 mmoles) of (carbomethoxymethylene)triphenylphosphorane (Compound CIV) in 6 ml. of dry toluene is refluxed under nitrogen for 7 hours. The reaction mixture is cooled to 20°-25° C., diethyl ether is added, and the mixture is filtered through a short silica gel column. The eluate is evaporated at reduced pressure to obtain a yellow oil which is crystallized from 95% ethanol to obtain the product (302 mg.), m.p. 121°-122° C.

Revised procedure 80.9 g. (241.9 mmoles) of Compound CIV is added to a solution of 48 g. (≦201 mmoles) of crude Compound CIII (from Step 2, revised procedure) in 300 ml. of toluene, the reaction mixture is refluxed for 6 hours and cooled to 20°-25° C., the reaction mixture being stirred under nitrogen throughout. 1 l. of diethyl ether is added, and the mixture is filtered through a short pad (150 g.) of 230-400 mesh A.S.T.M. silica gel and evaporated at reduced pressure. The obtained solid is recrystallized from methanol to obtain the product as a yellow solid (39 g.). The mother liquor is concentrated at reduced pressure and flash chromatographed through a silica gel column utilizing 1:1 diethyl ether/petroleum ether as the eluant The filtrate is evaporated at reduced pressure to obtain additional product (9.89 g.). Total yield: 48.89 g. (82%). M.p. 121°-122° C.

Step 4 (Reaction AD)

Methyl (E)-3-[3'-(4''-fluorophenyl)spiro[cyclopentane-1,1'(1H)-inden]-2'-yl]propenoate (Compound CVI)

112 mg. (2.3 mmoles) of sodium hydride (as a 50% by weight dispersion in mineral oil) is added to a solution of 340 mg. (1.16 mmoles) of Compound CV in 5 ml. of dry dimethylformamide stirred at 0° C. , the reaction mixture is stirred at 0° C. for 10 minutes, 0.143 ml. (1.16 mmoles) of 1,4-dibromobutane is added dropwise with stirring over a 5 minute period, and the reaction mixture is allowed to gradually warm to 20°-25° C. with stirring and stirred at 20°-25° C. for 16 hours, the reaction mixture being maintained under nitrogen throughout. The reaction mixture is diluted with diethyl ether, dilute hydrochloric acid is added, and the mixture is extracted three times with diethyl ether. The diethyl ether extracts are combined, washed with water, washed with saturated sodium chloride solution, dried over anhydrous sodium sulfate, filtered and evaporated to dryness at reduced pressure. The residue is chromatographed on a silica gel column utilizing 4:1 petroleum ether/acetone as the eluant to obtain the product (250.4 mg.), m.p. 143°-145° C.

Revised procedure 12 g. of 50% sodium hydride/mineral oil (246 mmoles) is added portionwise to a solution of 36 g. (123 mmoles) of Compound CV in 320 ml. of dry dimethylformamide stirred at 0° C., the reaction mixture is stirred at 0° C. for 10 minutes, 14.7 ml. (123 mmoles) of 1,4-dibromobutane is added dropwise with stirring at 0° C., and the reaction mixture is allowed to warm to 20°-25° C. and stirred at 20°-25° C. for 16 hours, the reaction mixture being stirred under nitrogen throughout. The reaction mixture is poured into cold dilute hydrochloric acid, and the mixture is extracted three times with diethyl ether. The diethyl ether extracts are combined, washed with water, washed with saturated sodium chloride solution, dried over anhydrous sodium sulfate, filtered and evaporated at reduced pressure. In order to esterify any small amount of free acid that may be present, 150 ml. of methanol and 0.5 ml. of acetyl chloride are added to the residual solid, and the mixture is refluxed for 5 hours, cooled and evaporated at reduced pressure. The residue is recrystallized from methanol to obtain the product as a yellow solid (30 g. (71%)), m.p. 143°-145° C.

Step 5 (Reaction AE)

(E)-3-[3'-(4''-fluorophenyl)spiro[cyclopentane-1,1'(1H)-inden]-2'-yl]prop-2-en-1-ol (Compound CVII)

2 ml. of 1.5M. diisobutylaluminum hydride/toluene (3 mmoles) is added dropwise to a solution of 220 mg. (0.632 mmole) of Compound CVI in 4 ml. of dry methylene chloride stirred at −78° C. under nitrogen, and the reaction mixture is stirred under the same conditions for 20 minutes, quenched with dilute hydrochloric acid and extracted several times with methylene chloride. The methylene chloride extracts are combined, washed with water, washed with saturated sodium chloride solution, dried over anhydrous sodium sulfate, filtered and evaporated at reduced pressure to obtain the product which solidifies upon standing (184 mg.), m.p. 102°-104° C.

Revised procedure 110 ml. of 1.5M. diisobutylaluminum hydride/toluene (165 mmoles) is added dropwise to a solution of 29 g. (83 mmoles) of Compound CVI in 250 ml. of methylene chloride stirred at −50° C., and the reaction mixture is stirred at −50° C. for 15 minutes, the reaction mixture being stirred under nitrogen throughout. The reaction mixture is poured into cold 1N. hydrochloric acid and extracted three times with methylene chloride. The methylene chloride extracts are combined, washed with water, washed with saturated sodium chloride solution, dried over anhydrous sodium sulfate, filtered and evaporated at reduced pressure to obtain the crude product as a pale yellow solid (26.5 g.).

Step 6 (Reaction AF)

(E)-3-[3'-(4''-fluorophenyl)spiro[cyclopentane-1,1'(1H)-inden]-2'-yl]prop-2-enal (Compound CVIII)

300 mg. (3.45 mmoles) of activated manganese dioxide is added to a solution of 170 mg. (0.531 mmole) of Compound CVII in 4 ml. of dry toluene stirred at 20°-25° C., and the reaction mixture is stirred at 20°-25° C. under nitrogen for 24 hours, filtered to remove the manganese dioxide and evaporated at reduced pressure to obtain the yellow product which solidifies upon standing (150 mg.), m.p. 123°-125° C.

Revised procedure

A mixture of 26 g. ($\leq$81 mmoles) of crude Compound CVII (from Step 5, revised procedure), 60 g. (690 mmoles) of activated manganese dioxide and 300 ml. of toluene is stirred at 20°-25° C. for 48 hours under nitrogen, 300-600 ml. of diethyl ether is added to dilute the reaction mixture, and the mixture is filtered through a short pad (50 g.) of 230-400 mesh A.S.T.M. silica gel. The filtrate is evaporated at reduced pressure, and the residue is recrystallized from diethyl ether/petroleum ether to obtain the product as a yellow solid (15.5 g. (60% (Steps 5 and 6 combined))), m.p. 129°-130° C.

Step 7 (Reaction A)

Ethyl (E)-7-[3'-(4''-fluorophenyl)spiro[cyclopentane-1,1'(1H)-inden]-2'-yl]-5-hydroxy-3-oxohept-6-enoate (Compound CIX)

(a) A stock solution of the dianion of ethyl acetoacetate is prepared as follows: 7.5 ml. of 1.6M. n-butyllithium/hexane (12.0 mmoles) is added over a period of 5 minutes to a solution of 1.23 g. (12.2 mmoles) of diisopropylamine in 25 ml. of dry tetrahydrofuran stirred at −5°-0° C. under nitrogen, the rate of addition being such that the temperature does not exceed 5° C. The reaction mixture is stirred at −30° C. for 15 minutes under nitrogen, 780.8 mg. (6 mmoles) of ethyl acetoacetate (dried over molecular sieves) is slowly added, and the reaction mixture is stirred at −30°-−20° C. under nitrogen for 45 minutes.

(b) 3.3 ml. of the stock solution of the dianion of ethyl acetoacetate of Part (a) (0.6 mmole) is added to a solution of 126 mg. (0.396 mmole) of Compound CVIII in 3 ml. of dry tetrahydrofuran stirred at −60° C. under nitrogen, and the reaction mixture is stirred under the same conditions for 1 hour, quenched with water, acidified with dilute hydrochloric acid and extracted three times with ethyl acetate. The ethyl acetate extracts are combined, washed with water, washed with saturated sodium chloride solution, dried over anhydrous sodium sulfate, filtered and evaporated to dryness at reduced pressure. The residue is purified by preparative thin layer chromatography on silica gel plates utilizing 4:1 petroleum ether/acetone as the solvent to obtain the product as a pale yellow oil (140 mg.).

Revised procedure 12 ml. (94 mmoles) of ethyl acetoacetate is added to a solution of lithium diisopropylamide in dry tetrahydrofuran (prepared from 26.4 ml. (188.3 mmoles) of diisopropylamine, 118 ml. of 1.6M. n-butyllithium/hexane (188.8 mmoles) and 150 ml. of dry tetrahydrofuran at 0° C. for 5 minutes under nitrogen) stirred at −30° C., the reaction mixture is stirred at −30°-−20° C. for 30 minutes, a solution of 15 g. (47 mmoles) of Compound CVIII in 50 ml. of dry tetrahydrofuran is added dropwise with stirring at -30° C., and the reaction mixture is stirred at −30°-20° C. for 30 minutes, the reaction mixture being stirred under nitrogen throughout. The reaction mixture is poured into an about 1:5 mixture of cold 1N. hydrochloric acid and ethyl acetate, the organic phase is separated, the aqueous phase is extracted with ethyl acetate, and the ethyl acetate extract and the organic phase are combined, washed with water, washed with saturated sodium chloride solution, dried over anhydrous sodium sulfate, filtered and evaporated at reduced pressure to obtain the crude product as an oil (16 g.).

The product is a racemate that may be resolved by conventional means to obtain the 5R and 5S enantiomers.

Step 8 (Reaction B)

Ethyl erythro-(E)-3,5-dihydroxy-7-[3'-(4''-fluorophenyl)spiro[cyclopentane-1,1'(1H)-inden]-2'-yl]hept-6-enoate (Compound CX)

(a) 0.8 ml. of 1M. triethylborane/tetrahydrofuran (0.8 mmole) is added to a solution of 300 mg. (0.67 mmole) of Compound CIX in 10 ml. of dry tetrahydrofuran stirred at 20°-25° C. , 0.2 ml. of air is added via syringe, the reaction mixture is stirred at 20°-25° C. for 2 hours and cooled to −78° C., 0.06 g. (1.59 mmoles) of sodium borohydride is added in one portion, and the reaction mixture is stirred at −78° C. for 48 hours, the reaction mixture being maintained under nitrogen throughout. The cooling bath is removed, and 1N. hydrochloric acid is slowly added dropwise until the evolution of hydrogen ceases and the mixture is acidic (pH ~5), the internal temperature of the mixture being maintained below −20° C. throughout. 10 ml. of water is added, the mixture is extracted three times with diethyl ether, and the diethyl ether extracts are combined, washed twice with water, washed with saturated sodium chloride solution, dried over anhydrous sodium sulfate, filtered and evaporated at reduced pressure to obtain a crude oil.

(b) A solution of the product of Part (a) in 5 ml. of methanol is stirred at 20°-25° C. for 66 hours under nitrogen and evaporated to dryness at reduced pressure. The residue is chromatographed on a silica gel column utilizing 1:1 diethyl ether/petroleum ether as the eluant to obtain the crude product which solidifies on standing (182 mg.). Repeated recrystallization from diethyl ether/hexane gave the product as a white solid, m.p. 90°-92° C.

Revised procedure (a) 40 ml. of 1M. triethylborane/tetrahydrofuran (40 mmoles) is added to a solution of 16 g. (≦33 mmoles) of crude Compound CIX (from Step 7, revised procedure) in 200 ml. of tetrahydrofuran, 10 ml. of air (at 25° C. and 760 mm. Hg) is bubbled in via syringe, the reaction mixture is stirred at 20°-25° C. for 2 hours and cooled to −78° C., 2 g. (53 mmoles) of solid sodium borohydride is added, and the reaction mixture is stirred at −78° C. for 48 hours, the reaction mixture being stirred under nitrogen throughout. The cooling bath is removed, the reaction mixture is slowly quenched at −78°-60° C. with 110 ml. of 1N. hydrochloric acid, 500 ml. of water is added, and the mixture is extracted three times with diethyl ether. The diethyl ether extracts are combined, washed with water, washed with saturated sodium chloride solution, dried over anhydrous sodium sulfate, filtered and evaporated at reduced pressure to obtain a pale yellow oil (17.2 g.).

(b) A solution of the pale yellow oil of Part (a) in 100 ml. of methanol is stirred at 20°-25° C. for 48 hours and evaporated at reduced pressure, and the residual oil is flash chromatographed through a silica gel column utilizing 1:1 diethyl ether/petroleum ether as the eluant. The eluant is evaporated at reduced pressure to obtain a white solid (9 g.) which is recrystallized two or three times from diethyl 1 ether/petroleum ether to obtain the pure product (~4-5 g.), m.p. 90°-93° C.

N.M.R. (CDCl$_3$): 1.3 (t, 3H), 1.6-1.9 (m, 4H), 2.2 (m, 6H), 2.5 (m, 2H), 3.2 (bs, 1H), 3.7 (bs, 1H), 4.15 (q, 2H), 4.25 (m, 1H), 4.45 (m, 1H), 5.8 (dd (J$_1$=8 Hz., J$_2$=20 Hz.), 1H), 6.5 (d (J=20 Hz.), 1H), 7.0-7.5 (m, 8H)

The product is an about 19:1 (revised procedure) or 24:1 (initial procedure) mixture of the erythro and threo racemates which may be separated by conventional means. The principal product, the erythro racemate, may be resolved into two optically pure enantiomers, the 3R,5S and 3S,5R isomers, of which the former is preferred. The minor product, the threo racemate, may be resolved into the 3R,5R and 3S,5S isomers, of which the former is preferred. The use of a nonstereoselective reduction would afford a mixture of all four stereoisomers wherein the ratio of the erythro stereoisomers to the threo stereoisomers ranges from 3:2 to 2:3.

EXAMPLE 1A 1,1-Dimethylethyl (3R,5S)-(E)-3,5-dihydroxy-7-[3'-(4''-fluorophenyl)-spiro[cyclopentane-1,1'-(1H)-inden]2'-yl]hept-6-enoate

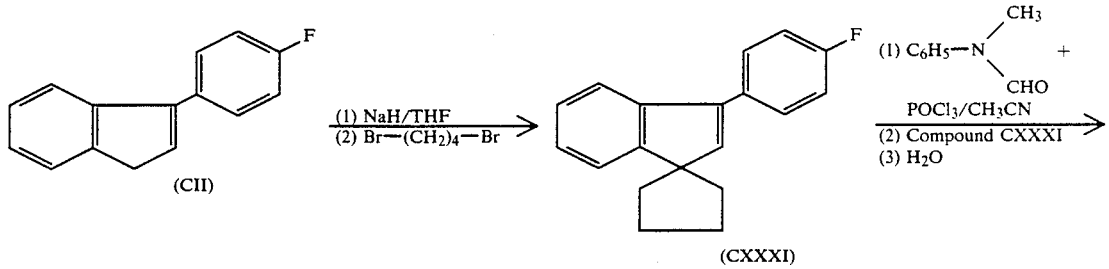

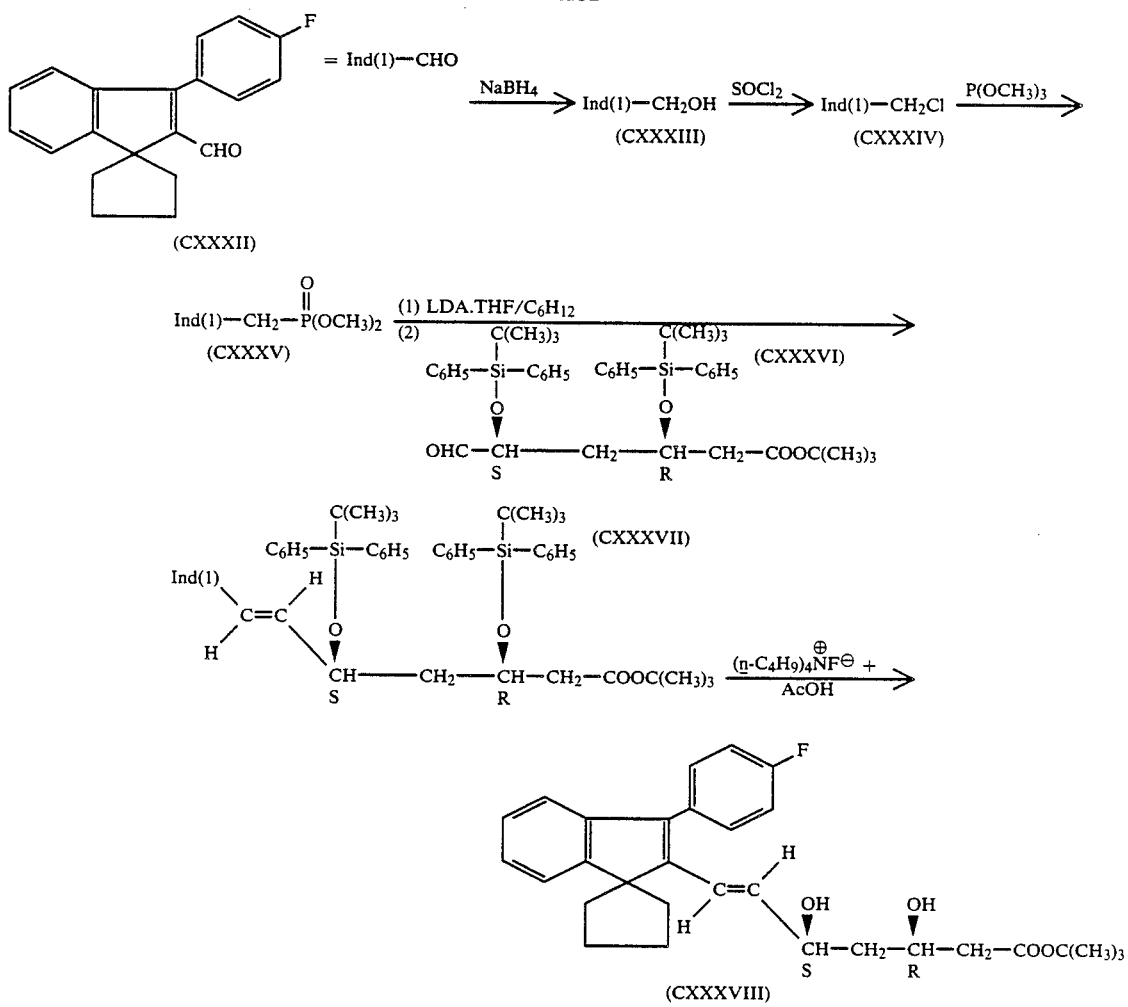

Step 1 (Reaction AM)
3-(4'-Fluorophenyl)spiro[cyclopentane-1,1'(1H)-indene](Compound CXXXI)

135 g. of 60% sodium hydride/mineral oil (3.375 moles) is added portionwise over a period of 40 minutes to a solution of 275 g. (1.31 moles) of Compound CII in 2.7 l. of HPLC grade tetrahydrofuran stirred at 0°–5° C., the mixture is stirred at 0° C. for 30 minutes, 156 ml. (282 g., 1.31 moles) of 1,4-dibromobutane is added over a period of 15 minutes with stirring at 0°–5° C. , and the reaction mixture is allowed to slowly warm to 20°–25° C. and is stirred at 20°–25° C. for 16 hours, the reaction mixture being stirred under nitrogen throughout. The reaction mixture is poured into 3 l. of cold 2N. hydrochloric acid, and the mixture is extracted twice with 1 l portions of ethyl acetate. The ethyl acetate extracts are combined, washed with 1.5 l of water, washed with 1.5 l of saturated sodium chloride solution, dried over anhydrous sodium sulfate, filtered and evaporated at 50° C. and reduced pressure to obtain a red oil (474 g.). The red oil is divided in half, and each 237 g sample is dissolved in the minimum amount of 10% acetone/hexane and chromatographed on a mixture of 500 g. of 70–230 mesh A.S.T.M. silica gel and 500 g. of 230–400 mesh A.S.T.M. silica gel utilizing 6 l of hexane as the eluant The fractions containing the product as indicated by thin layer chromatography (TLC) are combined and evaporated at reduced pressure to obtain the product as a yellow oil (242 g.).

Step 2 (Reaction AH)
3-(4'-Fluorophenyl)spiro[cyclopentane-1,1'(1H)-inden]-2-carboxaldehyde (Compound CXXXII)

778 g. (5.07 moles) of phosphorus oxychloride is added to 685 g. (5.07 moles) of N-methylformanilide stirred at 20°–25° C. (the temperature rising to 35° C.), the reaction mixture is cooled to 20°–25° C. and stirred at this temperature for 25 minutes, a solution of 269 g. (1.02 moles) of Compound CXXXI in 650 ml. of acetonitrile is added with stirring at 25°–38° C. over a period of 20 minutes, and the reaction mixture is heated to reflux (it exotherms at ~75°–85° C. ), refluxed for 32 hours and stirred at 20°–25° C. for 3 days, the reaction mixture being stirred under nitrogen throughout. The reaction mixture is poured portionwise into a mixture of 6 l of 10% sodium hydroxide solution and 4 kg. of ice, and the mixture is extracted three times with 2 l portions of ethyl acetate. The ethyl acetate extracts are combined, washed twice with 6 l portions of water and once with 4 l of saturated sodium chloride solution, dried over anhydrous sodium sulfate, filtered and evaporated at 50°–55° C. and reduced pressure to obtain a brown oil (600 g.). The brown oil is divided in half, and each 300 g. sample is dissolved in the minimum amount of methylene chloride and chromatographed on a pad consisting of a mixture of 500 g. of 70–230 mesh A.S.T.M. silica gel and 500 g of 230–400 mesh A.S.T.M. silica gel utilizing 5 l of 20% ethyl acetate/hexane as the eluant. The fractions of each chromatography containing the product (as indicated by TLC) are combined and evaporated at 50°–55° C. and reduced to stand at 20°–25° C. for 11 days, and the resulting yellow solid is collected, recrystallized from isopropanol/heptane (and vacuum dried at 20°–25° C. to obtain the pure product as a yellow solid (46 g.), m.p. 118°–120° C. The mother liquors from the initial crystallization and the recrystallization are combined and evaporated at 50°–55° C. and reduced pressure, and the resulting oil is chromatographed on a mixture of 2 kg. of 70–230 mesh A.S.T.M. silica gel and 2 kg. of 230–400 mesh A.S.T.M. silica gel utilizing 5% ethyl acetate/hexane and then 10% ethyl acetate/hexane as the eluants. The fractions containing relatively pure product (as indicated by TLC) are combined and evaporated at reduced pressure to obtain the crude product as a yellow solid (55 g.). The crude product is recrystallized from isopropanol/hexane and vacuum dried to obtain additional pure product as a yellow solid (27 g.), m.p. 117°–119° C. The fractions from the second chromatography containing some product (as indicated by TLC) are combined and evaporated at reduced pressure to obtain a yellow oil (120 g.) which is crystallized from isopropanol/hexane to obtain additional pure product (12 g.). The mother liquors from the two previous crystallizations are combined and evaporated at reduced pressure to obtain a yellow oil (132 g.) which is chromatographed on a mixture of 400 g. of 70–230 mesh A.S.T.M. silica gel and 400 g. of 230–400 mesh A.S.T.M. silica gel utilizing hexane and then 5% ethyl acetate/hexane as the eluants. Unreacted starting material is recovered from the fractions containing it, the fractions containing relatively pure product are combined and evaporated at reduced pressure, and the obtained yellow oil is crystallized from isopropanol with cooling at 0° C. The yellow solid is collected by filtration, washed with cold hexane and vacuum dried at 20°–25° C. to obtain additional pure product as a yellow solid (10 g.). Total yield: 96 g., m.p. 115°–118° C.

Step 3 (Reaction BA)

3-(4'-Fluorophenyl)spiro[cyclopentane-1,1'(1H)-inden]-2methanol (Compound CXXXIII)

A solution of 96 g. (328.4 mmoles) of Compound CXXXII in 445 ml. of HPLC grade tetrahydrofuran is added to a mixture of 14.2 g. (375 mmoles) of sodium borohydride, 445 ml. of HPLC grade tetrahydrofuran and 177 ml. of HPLC grade isopropanol (stirred at 15°–20° C. (the addition being exothermic), and the reaction mixture is stirred at 20°–25° C. for 24 hours, the reaction mixture being stirred under nitrogen throughout. The reaction mixture is cautiously poured into 800 ml. of saturated ammonium chloride solution stirred at 20°–25° C. (the addition being exothermic), and the organic phase is separated. The aqueous phase is extracted with 500 ml. of ethyl acetate, and the ethyl acetate extract is combined with the previous organic phase. The combined solution is dried over anhydrous magnesium sulfate and filtered, and the filter cake is washed with 200 ml. of ethyl acetate. The washing is combined with the filtrate, and the combined solution is concentrated at 50° C. (external temperature) and reduced pressure to a volume of about 150 ml. 500 ml. of heptane is added, and the mixture is concentrated at 50° C. (external temperature) and reduced pressure until it becomes opaque and cooled to 0° C. After 1 hour, the solids are collected by filtration, washed with 100 ml. of cold heptane and vacuum dried for 4 hours at 45° C. to constant weight to obtain the product (68.6 g.), m.p. 84°–86° C. A less pure second crop is obtained from the mother liquor (11.9 g.). The two crops are combined and dissolved in 1 l. of methanol, the methanol is evaporated at 50° C. and reduced pressure, 1 l. of methanol is added, the methanol is evaporated at 50° C. and reduced pressure to obtain a yellow oil containing some methanol, and 400 ml. of heptane is added. The mixture is slowly cooled to 10° C. and maintained at 0° C. for 30 minutes. The resulting solid is collected by filtration, washed with heptane and vacuum dried at 40° C. for 16 hours to obtain the product as a beige solid (70 g.), m.p. 90°–92° C. The mother liquor is evaporated at reduced pressure, and the residue is crystallized from 50 ml. of heptane, collected by filtration, washed with heptane and vacuum dried at 20°–25° C. for 16 hours to obtain a second crop (6.5 g.).

Step 4 (Reaction BB)

2-Chloromethyl-3-(4'-fluorophenyl)spiro[cyclopentane-1,1'(1H)-indene](Compound CXXXIV)

27 ml. (41 g., 350 mmoles) of thionyl chloride is added over a period of 15 minutes to a solution of 76.5 g. (260 mmoles) of Compound CXXXIII in 1.4 l of methylene chloride stirred at 19°–23° C. (the addition being slightly exothermic), and the reaction mixture is stirred at 20°–25° C. for 16 hours, the reaction mixture being stirred under nitrogen throughout. The methylene chloride is evaporated at reduced pressure. 300 ml. toluene is added, the toluene is evaporated at reduced pressure, and this is repeated twice more to obtain the crude product as a greenish oil (90 g.).

Step 5 (Reaction BC)

Dimethyl 3-(4'-fluorophenyl)spirocyclopentane-1,1'(1H)-inden]-2'-yl]methylphosohonate (Compound CXXXV)

A mixture of 90 g. ($\leq 0.26$ mole) of crude Compound CXXXIV and 220 ml. (231 g., 1.86 moles) of trimethyl phosphite is stirred at 100°–105° C. under nitrogen for 16 hours and evaporated at 65° C. and reduced pressure. 300 ml. of toluene is added, the toluene is evaporated at reduced pressure, and this is repeated twice. 400 ml. of heptane is added, and the heptane is evaporated at reduced pressure. 300 ml. of heptane and 50 ml. of diethyl ether are added, and the resulting solid is collected by filtration, washed with heptane and vacuum dried to obtain a pale green solid. The pale green solid is dissolved in 100 ml. of methylene chloride with heating, 500 ml of heptane is added, ~200 ml of heptane is evaporated at reduced pressure, and the mixture is cooled. The resulting solid is collected by filtration, washed with heptane and vacuum dried at 45° C. for 16 hours to obtain the product as an off-white solid (78 g.), m.p. 91°–92.5° C. A less pure second crop is obtained from the mother liquor (13 g.).

Step 6 (Reaction G)

1,1-Dimethylethyl (3R,5S)-(E)-3,5-di-(1',1'-dimethylethyl-diphenylsilyloxy)-7-[3'-(4''-fluorophenyl)-spiro[cyclopentane1,1'(1H)-inden]-2'-yl]hept-6-enoate (Compound CXXXVII)

20.75 ml of 1.5M. lithium diisopropylamide monotetrahydrofuran/cyclohexane (31.1 mmoles) is added to a solution of 10.0 g. (25.9 mmoles) of Compound CXXXV in 90 ml. of dry tetrahydrofuran stirred at −20°–0° C., the reaction mixture is stirred at −20°–15° C. for 30 minutes, a solution of 21.6 g. (31.1 mmoles) of Compound CXXXVI (disclosed in U.S. Pat. Nos. 4,808,607, 4,822,799 and 4,870,199 in 50 ml. of dry tetrahydrofuran is added dropwise with stirring at −20° C., and the reaction mixture is stirred at −20°–10° C. for 20 minutes, the reaction mixture being stirred under nitrogen throughout. 150 ml. of saturated ammonium chloride solution is added, and the mixture is extracted three times with ethyl acetate. The ethyl acetate extracts are combined, washed with water, washed with saturated sodium chloride solution, dried over anhydrous magnesium sulfate, filtered and evaporated at reduced pressure to obtain the crude product as a yellow solid (28.9 g.). The crude product is chromatographed on a Waters Prep-500 HPLC apparatus having a silica gel column and using 30% methylene chloride/hexane as the eluant to obtain the product as a white solid foam (19.28 g.), $[\alpha]_D^{25}$32 −127.7° (c=1.360 g./dl., CH$_3$OH).

Step 7 (Reaction H)

1,1-Dimethylethyl (3R,5S)-(E)-3,5-dihydroxy-7-[3′-(4″-fluorophenyl)spiro[cyclopentane-1,1′(1H)-inden]-2′-yl]hept-6-enoate (Compound CXXXVIII)

111.0 ml of 1M. tetra-n-butylammonium fluoride/tetrahydrofuran (111.0 mmoles) is added to a solution of 8.88 g. (9.30 mmoles) of Compound CXXXVII in 250 ml. of tetrahydrofuran, 3.05 ml. (3.20 g., 53.3 mmoles) of glacial acetic acid is added, 25.5 ml. of acetonitrile is added, and the reaction mixture is stirred at 60° C. for 29.5 hours and at 20°–25° C. for 88 hours, the reaction mixture being stirred under nitrogen throughout. 150 ml. of saturated sodium bicarbonate solution is added, and the mixture is extracted twice with 750 ml. portions of ethyl acetate. The ethyl acetate extracts are combined, washed with water, washed with saturated sodium chloride solution, dried over anhydrous magnesium sulfate and filtered. The filter cake is washed with ethyl acetate, the washing is combined with the filtrate, and the combined solution is evaporated at reduced pressure to obtain the crude product as a brown oil (12.69 g.). The crude product is chromatographed on a Waters Prep-500 HPLC apparatus having a silica gel column using 10% ethyl acetate/hexane as the eluant to obtain the 98.85% pure product (3.32 9.), m.p. 110°–112° C.

EXAMPLE 2

Sodium erythro-(E)-3,5-dihydroxy-7-[3′-(4″-fluorophenyl)-spiro[cyclopentane-1,1′(1H)-inden]-2′-yl]hept-6-enoate (Compound CXI)

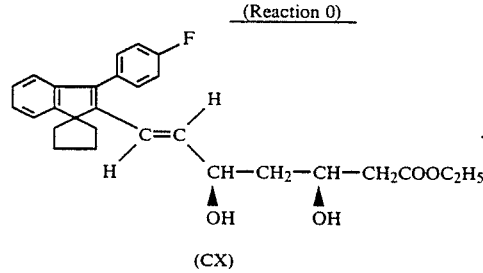

(CX)

-continued
(Reaction 0)

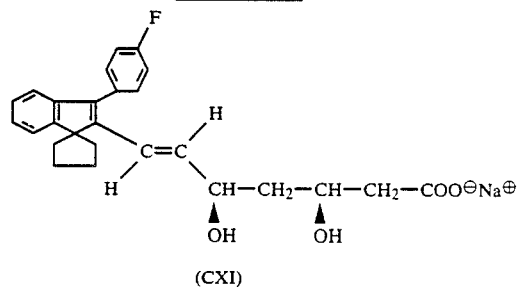

(CXI)

0.11 ml. of 1N. sodium hydroxide solution (0.11 mmole) is added to a solution of 50 mg. (0.111 mmole) of Compound CX in 3 ml. of absolute ethanol stirred at 0° C., and the reaction mixture is stirred at 0° C. under nitrogen for 1.5 hours and evaporated to dryness at reduced pressure. The residue is washed three times with diethyl ether to obtain the product (42 mg.), m.p. >170° C. (dec.).

Revised procedure 10 ml. of 1N. sodium hydroxide solution (10 mmoles) is added dropwise to a solution of 4.77 g. (10.6 mmoles) of Compound CX in 100 ml. of absolute ethanol stirred at 0° C. The reaction mixture is stirred at 0° C. for 30 minutes under nitrogen, diethyl ether is added, and the precipitate is collected by filtration, washed with diethyl ether and vacuum dried to obtain the product as a pale yellow solid (4.0 g.).

N.M.R. (CDCl$_3$+CD$_3$OD): 1.5–2.5 (m, 12H), 4.1 (m, 1H), 4.3 (m, 1H), 5.8 (dd (J$_1$=8 Hz., J$_2$=20 Hz.), 1H), 6.4 (d (J=20 Hz.), 1H), 7.0–7.5 (m, 8H)

The product is an about 19:1 (revised procedure) or 24:1 (initial procedure) mixture of the erythro and threo racemates which may be separated by conventional means. The principal product, the erythro racemate, may be resolved into two optically pure enantiomers, the 3R,5S and 3S,5R isomers, of which the former is preferred. The minor product, the threo racemate, may be resolved into the 3R,5R and 3S,5S isomers, of which the former is preferred. The use of a starting material synthesized by utilizing a non-stereoselective reduction in Step 8 of Example 1 would afford a mixture of all four stereoisomers wherein the ratio of the erythro isomers to the threo isomers ranges from 3:2 to 2:3.

EXAMPLE 2A

Sodium (3R,5S)-(E)-3,5-dihydroxy-7-[3′-(4″-fluorophenyl)-spiro[cyclopentane-1,1′(1H)-inden]-2′-yl]hept-6-enoate (Compound CXXXIX)

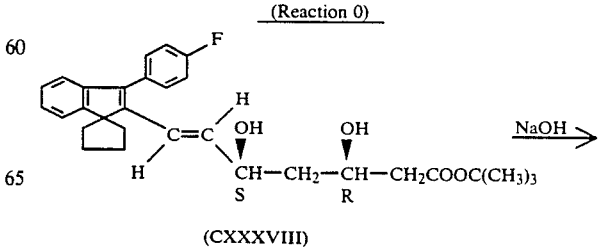

(CXXXVIII)

-continued
(Reaction 0)

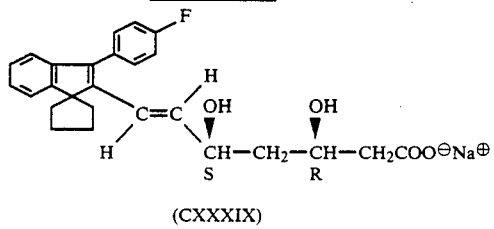

(CXXXIX)

7.07 ml. of 1N. sodium hydroxide solution (7.07 mmoles) is added dropwise to a solution of 3.45 g. (7.22 mmoles) of Compound CXXXVIII in 50 ml. of absolute ethanol stirred at 0° C., the reaction mixture is stirred at 0° C. for 2 hours, an additional 0.5 ml. of 1N. sodium hydroxide solution (0.5 mmole) is added, and the reaction mixture is stirred at 0° C. for 1.25 hours, the reaction mixture being stirred under nitrogen throughout. Diethyl ether is added, and the precipitate is collected by filtration, washed with diethyl ether and vacuum dried to constant weight to obtain the product as a pinkish-white solid (3.08 g.), $[\alpha]_D^{25} = +32.09°$ (c = 1.427 g./dl., $CH_3OH$).

EXAMPLES 3–5

(E)-3,5-dihydroxy-7-[3'-(3",5"-dimethylphenyl)spiro[cyclopentane-1,1'(1H)-inden]-2'-yl]hept-6-enoic acid, its sodium salt and its ethyl ester

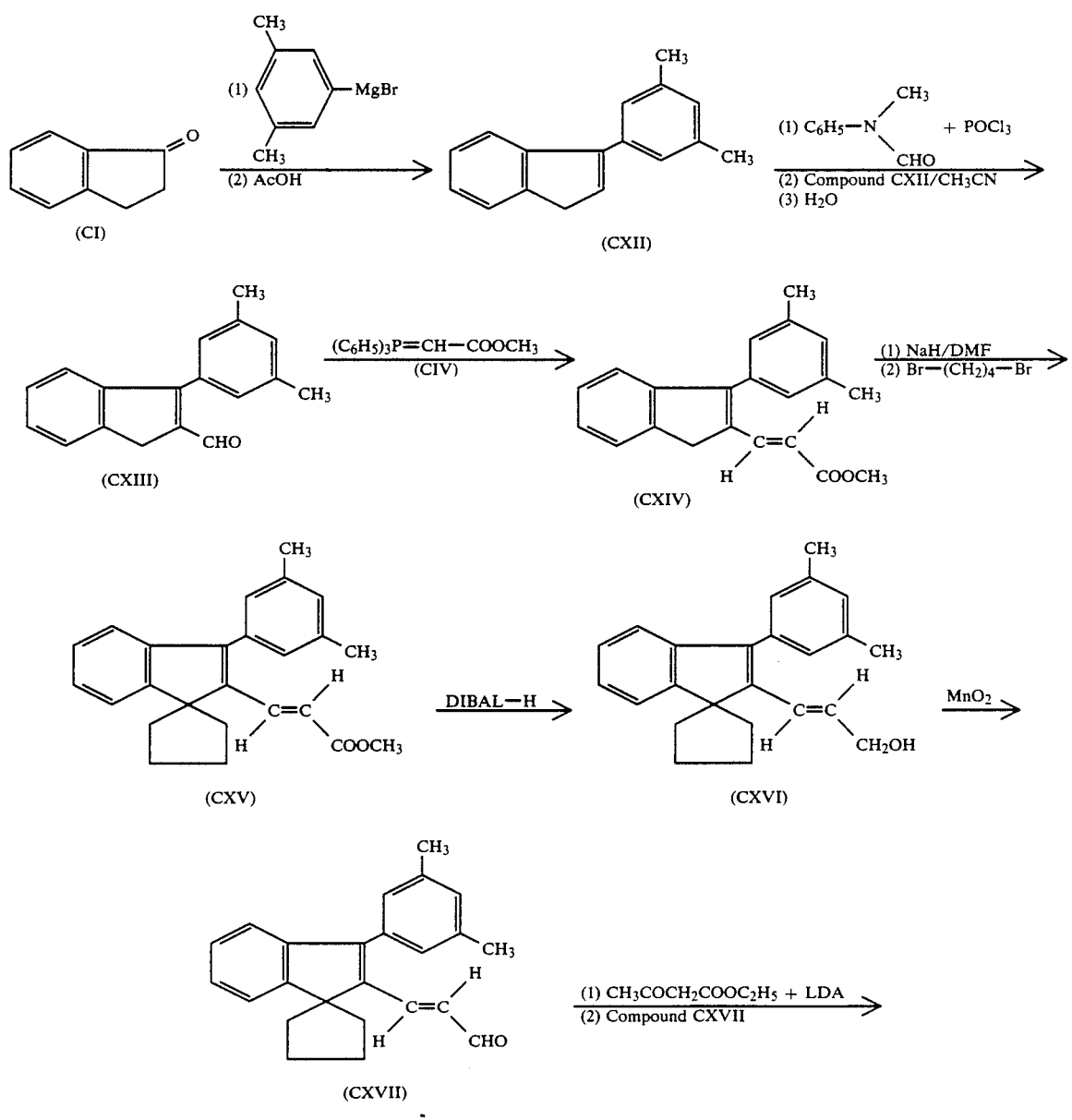

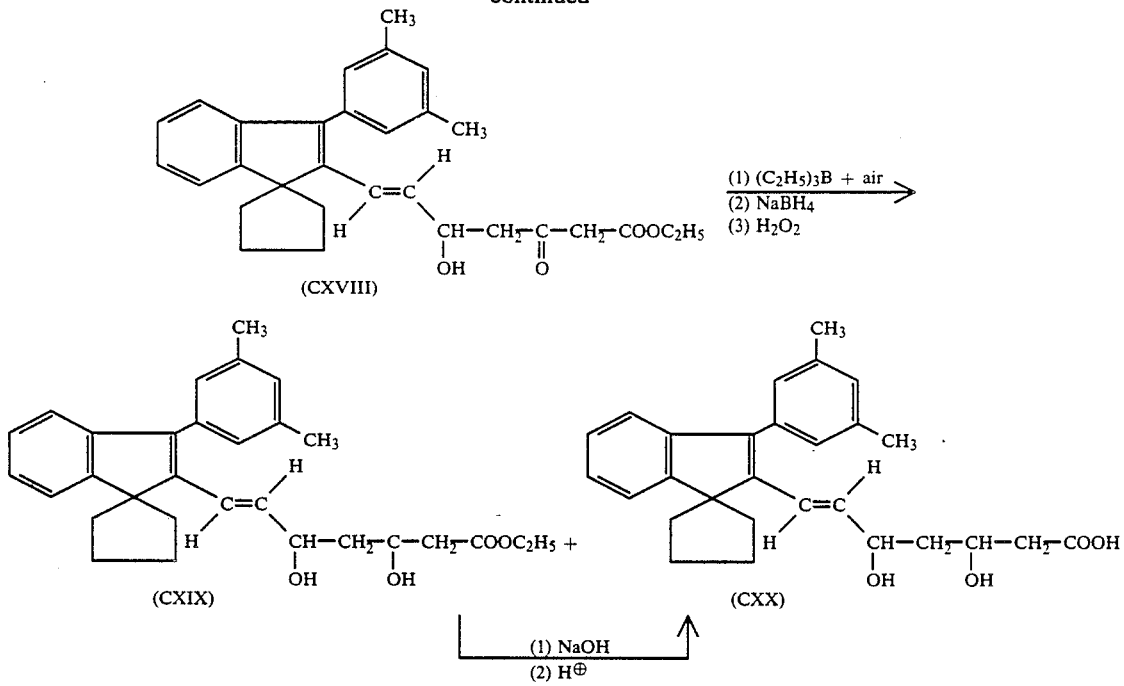

Step 1 (Reaction AA)

3-(3',5'-Dimethylphenyl)-1H-indene (Compound CXII)

20 mg. of iodine and 0.2-0.3 ml. of 1,2-dibromoethane are added to a suspension of 5 g. (0.21 mole) of magnesium in 15 ml. of dry tetrahydrofuran stirred at 20°-25° C. under nitrogen. When the reaction commences and the color of iodine disappears, a solution of 38 g. (0.205 mole) of 1-bromo-3,5-dimethylbenzene in 150 ml. of dry tetrahydrofuran is added dropwise over a period of about 1 hour at a rate such that the reaction mixture gently refluxes, the reaction mixture is refluxed for 1 hour and cooled to 20°-25° C., a solution of 26 g. (0.197 mole) of 1-indanone in 150 ml. of dry tetrahydrofuran is added dropwise over a period of 30 minutes, and the reaction mixture is maintained at 20°-25° C. for 30 minutes, the reaction mixture being stirred under nitrogen throughout. The reaction mixture is poured into cold (0°-5° C.) saturated ammonium chloride solution, and the mixture is extracted three times with ethyl acetate. The ethyl acetate extracts are combined, washed with water, washed with saturated sodium chloride solution, dried over anhydrous sodium sulfate, filtered and evaporated at reduced pressure to obtain a yellow oil (54 g.). The obtained oil is dissolved in 70 ml. of glacial acetic acid, and the reaction mixture is refluxed for 30 minutes and evaporated at reduced pressure to obtain a brown oil. The oil is subjected to a Kugelrohr distillation to obtain the product as a yellow oil (34 g. (79%)) (collected at a bath temperature of 115°-125° C. at 1 mm. Hg.).

Step 2 (Reaction AB)

3-(3',5'-Dimethylphenyl)-1H-indene-2-carboxaldehyde (Compound CXIII)

A mixture of 4.8 ml. (51.8 mmoles) of phosphorus oxychloride and 6.4 ml. (51.8 mmoles) of N-methylformanilide is allowed to stand at 20° C. under nitrogen for 30 minutes. The resulting yellow solution is cooled to 10° C., a solution of 9.5 g. (43.18 mmoles) of Compound CXII in 10 ml. of acetonitrile is added dropwise, and the reaction mixture is stirred at 20°-25° C. for 6 hours, the reaction mixture being maintained under nitrogen throughout. The reaction mixture is quenched with ice-water, and the mixture is extracted three times with diethyl ether. The diethyl ether extracts are combined, washed with water, washed with saturated sodium chloride solution, dried over anhydrous sodium sulfate, filtered and evaporated at reduced pressure to obtain the crude product as a dark yellow oil (10.6 g.).

Step 3 (Reaction AC)

Methyl (E)-3-[3'-(3'',5''-dimethylphenyl)-1H-inden-2'-yl]propenoate (Compound CXIV)

18 g. (58.8 mmoles) of (carbomethoxymethylene)triphenylphosphorane is added to a solution of 10.6 g. ($\leqq$42.7 mmoles) of crude Compound CXIII in 90 ml. of toluene, and the reaction mixture is refluxed for 4 hours (until no Compound CXIII is detectable by thin layer chromatography) and cooled to 20°-25° C., the reaction mixture being maintained under nitrogen throughout. 600 ml. of diethyl ether is added, and the mixture is filtered through a short pad (90 g.) of 230-400 mesh silica gel, decolored with 3-4 g. of Norit, filtered and evaporated at reduced pressure to an oil. The oil is triturated with petroleum ether and the resulting solid is vacuum dried to obtain the yellow product (12 g. (92% Steps 2 and 3 combined)), m.p. 98°-100° C.

Step 4 (Reaction AD)

Methyl (E)-3-[3'-(3'',5''-dimethylphenyl)spiro[cyclopentane-1,1'(1H)-inden]-2'-yl]propenoate (Compound CXV)

442 mg. (9.21 mmoles) of sodium hydride (as a 50% by weight dispersion in mineral oil) is added portionwise to a solution of 1.4 g. (4.6 mmoles) of Compound CXIV in 15 ml. of dry dimethylformamide stirred at 0° C., the reaction mixture is stirred at 0° C. for 10 minutes, 0.6 ml. (4.8 mmoles) of 1,4-dibromobutane is added dropwise, and the reaction mixture is allowed to slowly warm to 20°–25° C. and stirred at this temperature for 4–5 hours (until no Compound CXIV is detectable by thin layer chromatography), the reaction mixture being maintained under nitrogen throughout. The reaction mixture is poured into cold (0°–5° C.) water, and the mixture is extracted three times with diethyl ether. The diethyl ether extracts are combined, washed with water, washed with saturated sodium chloride solution, dried over anhydrous sodium sulfate, filtered and evaporated at reduced pressure. The residual oil is crystalized from methanol to obtain the pale yellow product (930 mg. (58%)), m.p. 118°–120° C. Additional product and the corresponding free acid may be obtained from the mother liquor. The free acid may be esterified to obtain still more product. Preferably, however, the entire residual oil is refluxed for 6 hours in a mixture of methanol and concentrated hydrochloric acid to esterify any free acid present prior to the crystallization from methanol Step 5 (Reaction AE)

(E)-3-[3'-(3'',5''-dimethylphenyl)spiro[cyclopentane-1,1'(1H)-inden]-2'-yl]prop-2-en-1-ol (Compound CXVI)

35 ml. of 1.5M. diisobutylaluminum hydride/toluene (52.5 mmoles) is added to a solution of 7.0 g. (19.53 mmoles) of Compound CXV in 120 ml. of methylene chloride stirred at −75° C. under nitrogen, and the reaction mixture is stirred under the same conditions for 2.5 hours and poured into about 200 ml. of ice-water. The mixture is acidified with 3N. hydrochloric acid to pH 3–4, 5 ml. of acetic acid is added, and the mixture is extracted three times with ethyl acetate. The ethyl acetate extracts are combined, washed with water, saturated sodium bicarbonate solution, water and saturated sodium chloride solution, dried over anhydrous sodium sulfate, filtered and evaporated at reduced pressure to obtain the crude product as a yellow oil (7 g.).

Step 6 (Reaction AF)

(E)-3-[3'-(3'',5''-dimethylphenyl)spiro[cyclopentane-1,1'(1H)-inden]-2'-yl]prop-2-enal (Compound CXVII)

A mixture of 7 g. (≦21.2 mmoles) of crude Compound CXVI (from Step 5), 14 g. (161 mmoles) of activated manganese dioxide and 140 ml. of toluene is stirred at 20°–25° C. under nitrogen for about 12 hours (until no Compound CXVI is detectable by thin layer chromatography), 500 ml. of diethyl ether is added, the mixture is filtered through a pad (20 g.) of 230–400 mesh silica gel and evaporated at reduced pressure, and the residual oil is triturated with petroleum ether to obtain the product as a yellow solid (6.05 g. (93% Steps 5 and 6 combined)), m.p. 149°–150° C.

Step 7 (Reaction A)

Ethyl (E)-7-[3'-(3'',5''-dimethylphenyl)spiro[cyclopentane-1,1'(1H)-inden-2'-yl-5-hydroxy-3-oxohept-6-enoate (Compound CXVIII)

51.3 ml. of 1.6M. n-butyllithium/hexane (84.3 mmoles) is slowly added to a solution of 11.8 ml. (84.3 mmoles) of diisopropylamine in dry tetrahydrofuran stirred at 0° C., the reaction mixture is stirred at 0° C. for 10 minutes and cooled to −30° C., 5.35 ml. (41.9 mmoles) of ethyl acetoacetate is slowly added, and the resulting yellow solution is stirred at −30°--−20° C. for 30 minutes, the reaction mixture being maintained under nitrogen throughout. The reaction mixture is added via syringe to a solution of 7.2 g. (21.9 mmoles) of Compound CXVII in 60 ml. of dry tetrahydrofuran stirred at −30° C., and the reaction mixture is stirred at −30°--−20° C. for about 30 minutes (until no Compound CXVII is detectable by thin layer chromatography), the reaction mixture being maintained under nitrogen throughout. The reaction mixture is poured into a mixture of cold (0°–5° C.) 1N. hydrochloric acid and ethyl acetate, the organic phase is separated, the aqueous phase is extracted twice with ethyl acetate, and the ethyl acetate phase and extracts are combined, washed with water, washed with saturated sodium chloride solution, dried over anhydrous sodium sulfate, filtered and evaporated at reduced pressure to obtain the crude oily product (12.0 g.).

The product is a racemate that may be resolved by conventional means to obtain the 5R and 5S enantiomers.

Step 8 (Reactions B, O and P)

(E)-3,5-dihydroxy-7-[3'-(3'',5''-dimethylphenyl)spiro[-cyclopentane-1,1'(1H)-inden]-2'-yl]hept-6-enoic acid (Compound CXX), its sodium salt (Compound CXXA) and its ethyl ester (Compound CXIX)

(a) 31 ml. of 1M. triethylborane/tetrahydrofuran (31 mmoles) is added to a solution of 12.0 g. (≦26.2 mmoles) of Compound CXVIII in 500 ml. of dry tetrahydrofuran stirred at 20°–25° C., 50 ml. of air (at 25° C. and 760 mm. Hg.) is added via a syringe, the reaction mixture is stirred at 20°–25° C. for 2 hours and cooled to −78° C., 1.14 g. (30.2 mmoles) of sodium borohydride is added in one portion, and the reaction mixture is stirred for 16 hours at −78° C. and allowed to warm to 20°–25° C., the reaction mixture being maintained under nitrogen throughout. The reaction mixture is evaporated to dryness at reduced pressure, the residue is vacuum dried, diethyl ether is added, the insoluble material is removed by filtration, and the filtrate is evaporated at reduced pressure. 50 ml. of water is added to the oily residue, and the mixture is extracted twice with diethyl ether. The diethyl ether extracts are combined and cooled to 0° C., 10 ml. of methanol, 5 ml. of 30% aqueous hydrogen peroxide and 10 ml. of an aqueous phosphate buffer having a pH of 7 (0.054M. sodium, 0.024M. potassium and 0.047M. phosphate) are added, and the reaction mixture is stirred at 0° C. under nitrogen for 45 minutes. Most of the diethyl ether and methanol is evaporated at reduced pressure, the residual aqueous solution is extracted with diethyl ether three times, and the diethyl ether extracts are combined and evaporated at reduced pressure to obtain crude Compound CXIX as a yellow oil (3 g.) (Example 3).

N.M.R. (CDCl$_3$): 1.25 (t, 3H), 1.6–2.3 (m, 10H), 2.4 (s, 6H), 2.5 (m, 2H), 3.5 (s, 1H), 3.7 (d, 1H), 4.15 (q, 2H), 4.25 (m, 1H), 4.4 (m, 1H), 5.7 (dd, 1H), 6.5 (d (J=20 Hz.), 1H), 6.95–7.4 (m, 7H)

(b) The aqueous layer from the initial diethyl ether extraction (prior to the addition of methanol, hydrogen peroxide and buffer) is acidified with dilute hydrochloric acid, and the mixture is extracted twice with ethyl acetate. The ethyl acetate extracts are combined, dried over anhydrous sodium sulfate, filtered and evaporated at reduced pressure to obtain crude Compound CXX as a foam (7 g.) (Example 4).

(c) 6.5 ml. of 1N. sodium hydroxide solution (6.5 mmoles) is added to a solution of 3 g. (≦6.5 mmoles) of crude Compound CXIX (from Part (a)) in 25 ml. of ethanol stirred at 0° C., and the reaction mixture is stirred at 0° C. under nitrogen for 30 minutes, washed with diethyl ether, acidified with dilute hydrochloric acid and extracted with diethyl ether twice. The diethyl ether extracts are combined, dried over anhydrous sodium sulfate, filtered and evaporated at reduced pressure to obtain Compound CXX as an oil (1.7 g.).

The reaction mixture, prior to the acidification, contains the sodium salt of Compound CXX (Compound CXXA (Example 5)). It may be isolated and purified conventionally. M.p. ≧160° C. (dec.).

N.M.R. (CDCl$_3$+CD$_3$OD): 1.5-2.35 (m, 12H), 2.3 (s, 6H), 4.1 (m, 1H), 4.3 (m, 1H), 5.75 (dd, 1H), 6.45 (d (J=20 Hz.), 1H), 6.95-7.4 (m, 7H)

Compounds CXIX, CXX and CXXA are approximately 3-9:1 mixtures of the erythro and threo racemates which may be separated by conventional means, e.g., lactonization of the free acid, separation of the cis and trans lactones, hydrolysis of the lactones, etc. The principal product, the erythro racemate in each case, may be resolved into two optically pure enantiomers, the 3R,5S and 3S,5R enantiomers, of which the former is preferred The minor product, the threo racemate in each case, may be resolved to obtain the 3R,5R and 3S,5S enantiomers, of which the former is preferred. The use of a non-stereoselective reduction would afford a mixture of all four stereoisomers wherein the ratio of the erythro stereoisomers to the threo stereoisomers ranges from 3:2 to 2:3.

Note: To maximize the yield of Compound CXIX, it is preferable to carry out this step in accordance with the procedure of Step 8 of Example 1.

EXAMPLES 6 AND 7

(E)-Trans-6-(2'-[3''-(3''',5'''-dimethylphenyl)spiro[cyclopentane-1,1'(1H)-inden]-2''-yl]ethenyl)-4-hydroxy-3,4,5,6-tetrahydro-2H-pyran-2-one (Compound CXXI) and the corresponding cis lactone (Compound CXXII)

fonate is added to a solution of 8.7 g. (≦20.1 mmoles) of Compound CXX (from Parts (a) and (c) of Step 8 of Examples 3-5) in 250 ml. of methylene chloride (freshly filtered through basic alumina), and the reaction mixture is stirred at 20°-25° C. under nitrogen for about 3 hours (until no Compound CXX is detectable by thin layer chromatography) and evaporated to dryness at reduced pressure. Water is added, and the mixture is extracted three times with diethyl ether. The diethyl ether extracts are combined, washed with saturated sodium chloride solution, dried over anhydrous sodium sulfate, filtered and evaporated to dryness at reduced pressure to obtain an about 3-4:1 mixture of Compounds CXXI and CXXII as a yellow foam.

(b) The product of Part (a) is separated on a Waters Prep-500 high pressure liquid chromatography apparatus utilizing a silica gel column and 15:4.5:10.5 n-hexane/acetonitrile/methyl t-butyl ether to elute the trans lactone (Compound CXXI) (3.0 g.), a solid foam (Example 6).

N.M.R. (CDCl$_3$): 1.7-2.3 (m, 10H), 2.35 (s, 6H), 2.7 (m, 2H), 4.4 (m, 1H), 5.25 (m, 1H), 5.75 (dd (J$_1$=10 Hz., J$_2$=20 Hz.), 1H), 6.55 (d (J=20 Hz.), 1H), 6.9-7.5 (m, 7H)

Also eluted from the column is the cis lactone (Compound CXXII), also a solid foam (Example 7).

N.M.R. (CDCl$_3$): 1.7-2.5 (m, 10H), 2.35 (s, 6H), 2.8 (m, 2H), 4.3 (m, 1H), 4.7 (m, 1H), 5.75 (dd (J$_1$=10 Hz., J$_2$=20 Hz.), 1H), 6.5 (d (J=20 Hz.), 1H), 6.95-7.4 (m, 7H)

Compounds CXXI and CXXII are both racemates that may be resolved by conventional means to obtain, in the case of the former, the 4R,6S and 4S,6R enantiomers, of which the former is preferred, and, in the case of the latter, the 4R,6R and 4S,6S enantiomers, of which the former is preferred.

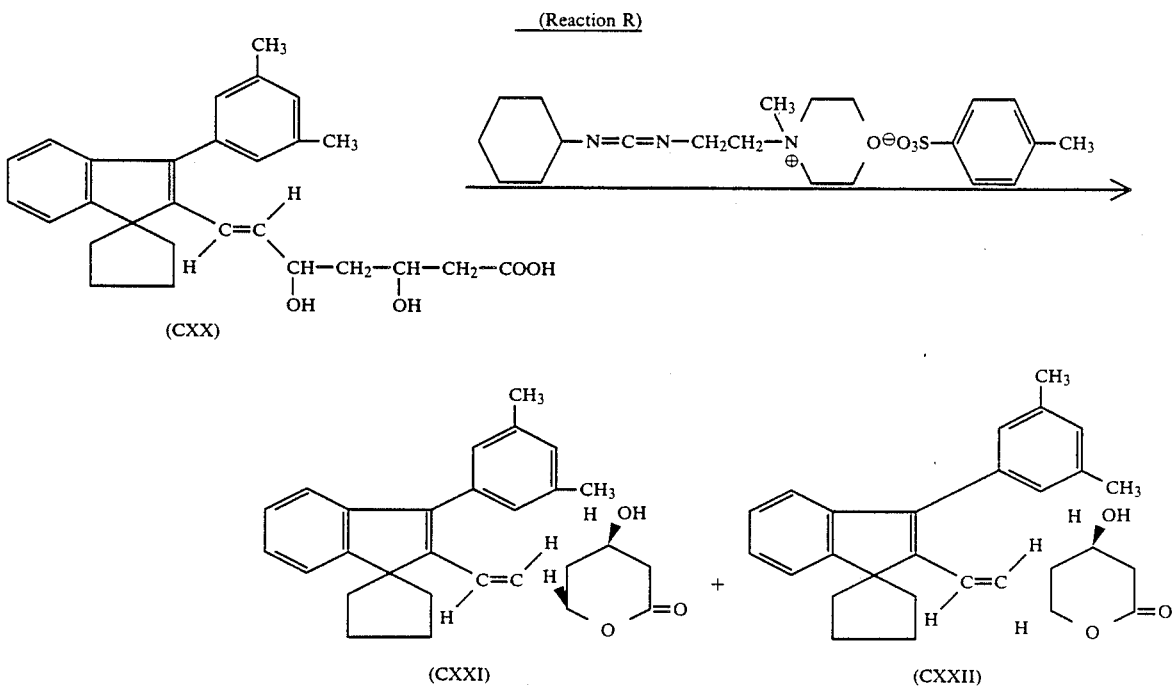

(a) 8.7 g. (20.5 mmoles) of N-cyclohexyl-N'-[2'-(N''-methylmorpholinium)ethyl]carbodiimide p-toluenesul-

EXAMPLE 8

Sodium erythro-(E)-3,5-dihydroxy-7-[3'-(3'',5''-dimethylphenyl)spiro[cyclopentane-1,1'(1H)-inden]-2'-yl]hept-6-enoate

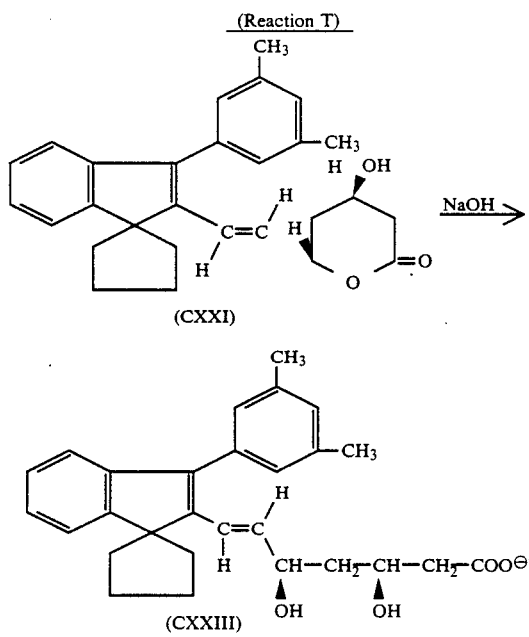

0.16 ml. of 1N. sodium hydroxide solution (0.16 mmole) is added to a solution of 70 mg. (0.169 mmole) of Compound CXXI in 3 ml. of absolute ethanol stirred at 0° C., and the reaction mixture is stirred at 0° C. under nitrogen for 30 minutes and evaporated to dryness at reduced pressure. The residue is washed with anhydrous diethyl ether and vacuum dried to obtain the product as a pale yellow solid (65 mg.), m.p. >170° C. (dec.)

N.M.R. (CDCl$_3$+CD$_3$OD): 1.5–2.35 (m, 12H), 2.3 (s, 6H), 4.1 (bs, 1H), 4.3 (bs, 1H), 5.75 (dd (J$_1$=10 Hz., J$_2$=20 Hz.), 1H), 6.45 (d (J=20 Hz.), 1H), 6.95–7.4 (m, 7H)

Compound CXXIII is a racemate that may be resolved by conventional means to obtain the 3R,5S and 3S,5R enantiomers, of which the former is preferred.

EXAMPLE 9

Sodium threo-(E)-3,5-dihydroxy-7-[3'-(3'',5''-dimethylphenyl)-spiro[cyclopentane-1,1'(1H)-inden]-2'-yl]hept-6-enoate

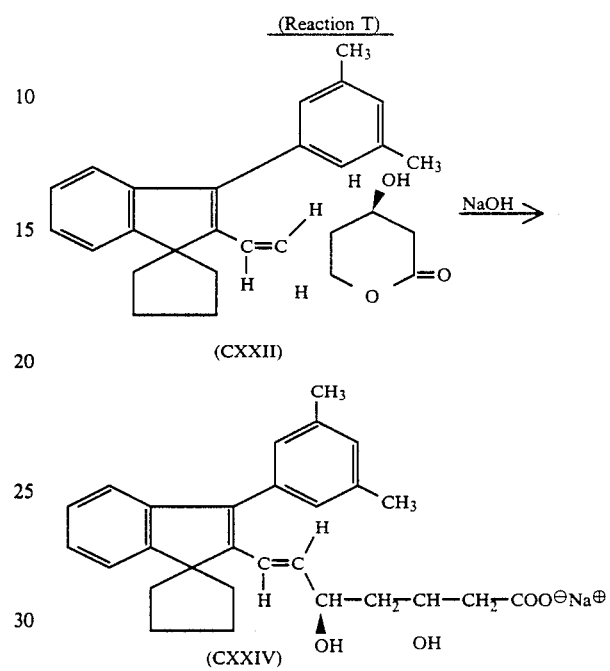

The product is obtained from Compound CXXII essentially according to the process of Example 8. M.p. >160° C. (dec.)

N.M.R. (CDCl$_3$+CD$_3$OD): Essentially the same as that of Compound CXXIII

Compound CXXIV is a racemate that may be resolved by conventional means (e.g., Reactions P and R, conversion of the racemic lactone to diastereoisomeric silyloxy compounds, separation of the diastereoisomeric silyloxy compounds, cleavage of the silyl group and Reaction T) to obtain the 3R,5R and 3S,5S enantiomers, of which the former is preferred.

EXAMPLE 10

Ethyl (±)-(E)-7-[3'-(4''-fluorophenyl)spiro[cyclopentane-1,1'-(1H)-inden]-2'-yl]-3-hydroxy-5-oxohept-6-enoate

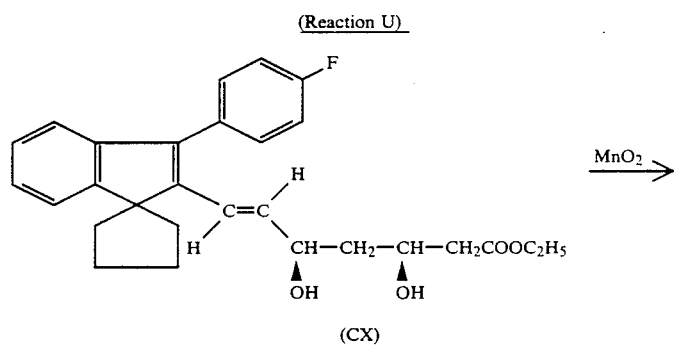

(Reaction U)

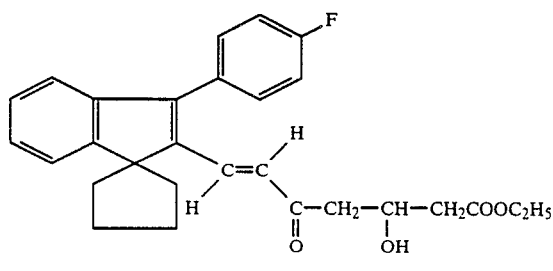

(CXXV)

A mixture of 310 mg. (0.69 mmole) of Compound CX, 600 mg. (4.2 mmoles) of activated manganese dioxide and 5 ml. Of toluene is stirred under nitrogen at 20°-25° C. for 24 hours, at 60° C. for 8 hours, at 20°-25° C. for 16 hours and at 80° C. for 8 hours and allowed to cool to 20°-25° C. Diethyl ether is added, the mixture is filtered, and the filtrate is evaporated at reduced pressure to obtain an oil. The oil is purified by preparative thin layer chromatography on a silica gel plate utilizing 80% diethyl ether/petroleum ether as the solvent. The band containing the product is scraped and eluted with ethyl acetate and the solution is filtered and evaporated at reduced pressure to obtain the product as a yellow solid (110 mg.), m.p. 107°-109° C.

The product is a racemate that may be resolved by conventional means to obtain the 3R and 3S enantiomers.

EXAMPLE 11

Ethyl (±)-(E)-5,5-dimethoxy-7-[3'-(4''-fluorophenyl)spiro-[cyclopentane-1,1'(1H)-inden]-2'-yl]-3-hydroxyhept-6-enoate A mixture of 90 mg. (0.20 mmole) of Compound CXXV, 0.1 ml. (0.91 mmole) of trimethyl orthoformate, 2 mg. of pyridinium p-toluenesulfonate and 3 ml of methylene chloride is stirred under nitrogen for 45 hours at 20°-25° C. and evaporated at reduced pressure, and the residual oil is purified by preparative thin layer chromatography on a silica gel plate utilizing 60% diethyl ether/petroleum ether as the solvent. The band containing the product is scraped and eluted with ethyl acetate, and the solution is filtered and evaporated at reduced pressure to obtain the product as a yellow oil (31 mg.).

N.M.R. (C$_6$D$_6$): 0.9 (t (J=10 Hz.), 3H), 1.2-3.1 (m, 12H), 3.2 (2s, 6H), 3.9 (q (J=10 Hz.), 2H), 4.8 (m, 1H), 6.5 (d (J=20 Hz.), 1H), 6.8-7.4 (m, 8H), 7.7 (d (J=20 Hz.), 1H)

The product is a racemate that may be resolved by conventional means to obtain the 3R and 3S enantiomers.

(Reaction ZA)

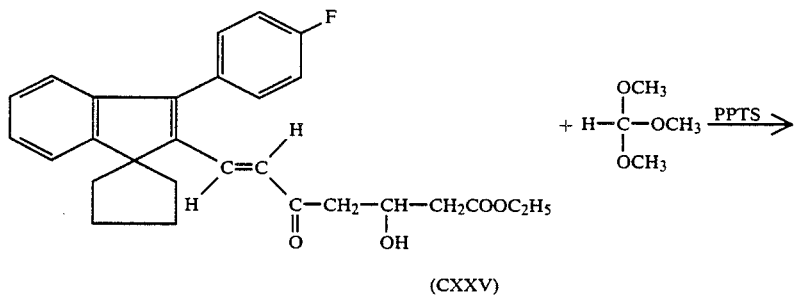

(CXXV)

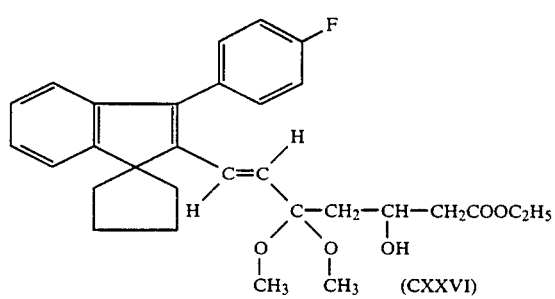

(CXXVI)

TABLE I

Examples 12-19
The following compounds of Group IAa wherein $R_0$ is Ring A may be synthesized by the processes set forth above:

| | R | $R_1$ | $R_2$ | $R_3$ | $R_4$ | $R_5$ | $R_6$ | X | $R_{10}$ | $R_{11}$ | Isomers | M.P. |
|---|---|---|---|---|---|---|---|---|---|---|---|---|
| Ex. 12 | H | i-$C_3H_7$ | H | H | H | 4-F | H | (E)-CH=CH— | H | $C_2H_5$ | Dl; E:T = ~85:15 | Oil |
| Ex. 13 | H | i-$C_3H_7$ | H | H | H | 4-F | H | (E)-CH=CH— | H | Na | Dl; E | <190° C. (dec.) |
| Ex. 14 | $CH_3$ | $CH_3$ | H | H | H | 4-F | H | (E)-CH=CH— | H | $C_2H_5$ | E:T = ~9:1 | Oil |
| Ex. 15 | $CH_3$ | $CH_3$ | H | H | H | 4-F | H | (E)-CH=CH— | H | Ha | E | <160° C. (dec.) |
| Ex. 16 | $C_2H_5$ | $C_2H_5$ | H | H | H | 4-F | H | (E)-CH=CH— | H | $C_2H_5$ | E:T = ~4:1 | Oil |
| Ex. 17 | $C_2H_5$ | $C_2H_5$ | H | H | H | 4-F | H | (E)-CH=CH— | H | Na | E:T = ~4:1 | <170° C. (dec.) |
| Ex. 18 | $CH_3$ | $CH_3$ | H | H | 3-$CH_3$ | H | 5-$CH_3$ | (E)-CH=CH— | H | $C_2H_5$ | E:T = ~9:1 | Oil |
| Ex. 19 | $CH_3$ | $CH_3$ | H | H | 3-$CH_3$ | H | 5-$CH_3$ | (E)-CH=CH— | H | Ha | E:T = ~9:1 | <190° C. (dec.) |

TABLE II

Examples 20-23
The following compounds of Group IAa
wherein $R_0$ is Ring A may be synthesized by the processes set forth above:

| | R | $R_1$ | $R_2$ | $R_3$ | $R_4$ | $R_5$ | $R_6$ | X | $R_{10}$ | Isomers | M.P. |
|---|---|---|---|---|---|---|---|---|---|---|---|
| Ex. 20 | H | i-$C_3H_7$ | H | H | H | 4-F | H | (E)-CH=CH— | H | Dl; trans | Oil |
| Ex. 21 | H | i-$C_3H_7$ | H | H | H | 4-F | H | (E)-CH=CH— | H | Dl; cis:trans = ~4:1 | Oil |
| Ex. 22 | $CH_3$ | $CH_3$ | H | H | H | 4-F | H | (E)-CH=CH— | H | trans | 64°-66° C. |
| Ex. 23 | $CH_3$ | $CH_3$ | H | H | 3-$CH_3$ | H | 5-$CH_3$ | (E)-CH=CH— | H | trans:cis = ~4:1 | Foam |

TABLE III

Examples 24-43

The following compounds of Group IIIa wherein $R_0$ is Ring A may be synthesized by the processes set forth above:

| | R + R₁ | R₂ | R₃ | R₄ | R₅ | R₆ | X | R₁₀ | R₁₁ | Isomers | M.P. |
|---|---|---|---|---|---|---|---|---|---|---|---|
| Ex. 24 | —CH₂CH₂— | H | H | H | 4-F | H | (E)—CH=CH— | H | C₂H₅ | E:T = ~89:11 | Oil |
| Ex. 25 | —CH₂CH₂— | H | H | H | 4-F | H | (E)—CH=CH— | H | Na | E:T = ~9:1 | >160° C. (dec.) |
| Ex. 26 | —(CH₂)₅— | H | H | H | 4-F | H | (E)—CH=CH— | H | C₂H₅ | E:T = ~3:1 | Oil |
| Ex. 27 | —(CH₂)₄— | H | H | H | H | H | (E)—CH=CH— | H | C₂H₅ | E:T = ~3:1 | Oil |
| Ex. 28 | —(CH₂)₄— | H | H | H | 4-F | H | —CH₂CH₂— | H | C₂H₅ | E:T = ~9:1 | Oil |
| Ex. 29 | —(CH₂)₄— | 4-CH₃ | H | H | 4-F | H | (E)—CH=CH— | H | C₂H₅ | E | Oil |
| Ex. 30 | —(CH₂)₄— | 4-CH₃ | H | H | 4-F | H | (E)—CH=CH— | H | Na | E | 213°–216° C. (dec.) |
| Ex. 31 | —(CH₂)₄— | 6-CH₃ | H | H | 4-F | H | (E)—CH=CH— | H | C₂H₅ | E | Oil |
| Ex. 32 | —(CH₂)₄— | 6-CH₃ | H | H | 4-F | H | (E)—CH=CH— | H | Na | E | 185°–189° C. (dec.) |
| Ex. 33 | —(CH₂)₄— | 6-OCH₃ | H | H | 4-F | H | (E)—CH=CH— | H | C₂H₅ | E | Oil |
| Ex. 34 | —(CH₂)₄— | 6-OCH₃ | H | H | 4-F | H | (E)—CH=CH— | H | Na | E | 199°–202° C. (dec.) |
| Ex. 35 | —(CH₂)₄— | 7-CH₃ | H | H | 4-F | H | (E)—CH=CH— | H | C₂H₅ | E | Oil |
| Ex. 36 | —(CH₂)₄— | 7-CH₃ | H | H | 4-F | H | (E)—CH=CH— | H | Na | E | 190° C. (dec.) |
| Ex. 37 | —(CH₂)₄— | 4-OCH₃ | 6-OCH₃ | H | 4-F | H | (E)—CH=CH— | H | C₂H₅ | E | 117°–118° C. |
| Ex. 38 | —(CH₂)₄— | 4-OCH₃ | 6-OCH₃ | H | 4-F | H | (E)—CH=CH— | H | Na | E | 196°–200° C. (dec.) |
| Ex. 39 | (Z)—CH₂—CH=CH—CH₂— | H | H | H | 4-F | H | (E)—CH=CH— | H | C₂H₅ | E | Oil |
| Ex. 40 | (Z)—CH₂—CH=CH—CH₂— | H | H | H | 4-F | H | (E)—CH=CH— | H | Na | E | 202°–206° C. (dec.) |
| Ex. 41 | —(CH₂)₄— | H | H | H | 4-F | H | (E)—CH=CH— | H | —CH₂—C₆H₄-4-Br | E | Solid |
| Ex. 42 | —(CH₂)₄— | H | H | H | 4-F | H | (E)—CH=CH— | H |  —CH₂—CH——CH₂ / O    O / C / CH₃  CH₃ | E | Oil |
| Ex. 43 | —(CH₂)₄— | H | H | H | 4-F | H | (E)—CH=CH— | H | Pyrid-3-yl-methyl | E | Solid Foam |

TABLE IV

Examples 44–47
The following compounds of Group IBa may be synthesized by the processes set forth above:

| | $R_o$ | $R + R_1$ | $R_2$ | $R_3$ | X | $R_{10}$ | $R_{11}$ | Isomers | M.P. |
|---|---|---|---|---|---|---|---|---|---|
| Ex. 44 | i-$C_3H_7$ | —$(CH_2)_4$— | H | H | (E)-CH=CH— | H | $C_2H_5$ | E:T = ~9:1 | Oil |
| Ex. 45 | i-$C_3H_7$ | —$(CH_2)_4$— | H | H | (E)-CH=CH— | H | Na | E:T = ~9:1 | 198°–200° C. (dec.) |
| Ex. 46 | Cyclohexyl | —$(CH_2)_4$— | H | H | (E)-CH=CH— | H | $C_2H_5$ | E | Solid Foam |
| Ex. 47 | Cyclohexyl | —$(CH_2)_4$— | H | H | (E)-CH=CH— | H | Na | E | 190°–194° C. (dec.) |

TABLE V

Example 48
The following compound of Group IBb
wherein $R_o$ is Ring A may be synthesized by the processes set forth above:

| | $R + R_1$ | $R_2$ | $R_3$ | $R_4$ | $R_5$ | $R_6$ | X | $R_{10}$ | Isomers | M.P. |
|---|---|---|---|---|---|---|---|---|---|---|
| Ex. 48 | —$(CH_2)_4$— | H | H | H | 4-F | H | (E)-CH=CH— | H | trans:cis = ~3:1 | Oil |

In Tables I–V

D1 = approximately 1:1 mixture of diastereoisomers with respect to the 1-position of the indene ring E = erythro racemate (E:T ≧ 19:1 unless otherwise indicated)

T = threo racemate cis = cis lactone trans = trans lactone (trans:cis ≧ 19:1 unless otherwise indicated Thus, for example, "D1; E:T = ~85:15" means that the compound is a mixture of eight stereoisomers wherein the ratio of the four erythro stereoisomers to the four threo stereoisomers is about 85:15 and the ratio of the four stereoisomers wherein $R_1$ has one configuration to the four stereoisomers wherein $R_1$ has the opposite configuration is about 1:1.

TABLE VI

| | N.M.R. Data |
|---|---|
| Ex. 12 ($CDCl_3$): | 0.3 (d (J=10 Hz.), 3H), 1.2 (t, 3H), 1.35 (d (J=10 Hz.), 3H), 1.7 (m, 2H), 2.5 (m, 2H), 3.3 (s, 1H), 3.7 (m, 1H), 4.2 (q, 2H), 4.3 (m, 1H), 4.5 (m, 1H), 5.8 (dd ($J_1$=10 Hz., $J_2$=20 Hz.), 1H), 6.5 (d (J=20 Hz.), 1H), 7.0–7.5 (m, 8H) |
| Ex. 13 ($CDCl_3$+$CD_3OD$): | 0.35 (d (J=10 Hz.), 3H), 1.4 (d (J=10 Hz.), 3H), 1.65 (m, 2H), 2.2–2.6 (m, 3H), 3.75 (bs, 1H), 4.15 (m, 1H), 4.4 (m, 1H), 5.9 (dd ($J_1$=10 Hz., $J_2$=20 Hz.), 1H), 6.55 (d (J=20 Hz.), 1H), 7.0–7.5 (m, 8H) |
| Ex. 14 ($CDCl_3$): | 1.3 (t, 3H), 1.5 (d, 6H), 1.6–1.9 (m, 2H), 2.5 (d, 2H), 4.2 (q, 2H), 4.3 (m, 1H), 4.5 (m, 1H), 6.0 (dd ($J_1$=10 Hz., $J_2$=20 Hz.), 1H), 6.55 (d (J=20 Hz.), 1H), 7.1–7.4 (m, 8H) |
| Ex. 15 ($CDCl_3$+$CD_3OD$): | 1.4 (d, 6H), 1.5 (m, 2H), 2.2 (m, 2H), 4.15 (m, 1H), 4.3 (m, 1H), 5.9 (dd $J_1$=10 Hz., $J_2$=20 Hz.), 1H), 6.4 (d (J=20 Hz.), 1H), 7.0–7.4 (m, 8H) |
| Ex. 16 ($CDCl_3$): | 0.35 (m, 6H), 1.3 (t (J=10 Hz.), 3H), 1.7 (m, 4H), 2.0 (m, 4H), 2.5 (d (J=10 Hz.), 2H), 4.2 (q (J=10 Hz.), 2H), 4.3 (m, 1H), 4.45 (m, 1H), 5.9 (dd ($J_1$=10 Hz., $J_2$=20 Hz.), 1H), 6.5 (d (J=20 Hz.), 1H), 7.1–7.4 (m, 8H) |
| Ex. 17 ($CDCl_3$+$CD_3OD$): | 0.35 (m, 6H), 1.7 (m, 2H), 2.0 (m, 4H), 2.3 (m, 2H), 4.1 (m, 1H), 4.35 (m, 1H), 5.9 (dd ($J_1$=10 Hz., $J_2$=20 Hz.), 1H), 6.5 (d (J=20 Hz.), 1H), 7.0–7.5 (m, 8H) |
| Ex. 18 ($CDCl_3$): | 1.25 (t, 3H), 1.5 (d (J=8 Hz.), 6H), 1.55–1.9 (m, 2H), 2.35 (s, 6H), 2.5 (d, 2H), 4.15 (q, 2H), 4.3 (m, 1H), 4.45 (m, 1H), 5.9 (dd ($J_1$=10 Hz., $J_2$=20 Hz.), 1H), 6.55 (d (J=20 Hz.), 1H), 7.0–7.4 (m, 7H) |
| Ex. 19 ($CDCl_3$+$CD_3OD$): | 1.4 (d, 6H), 1.5–1.9 (m, 2H), 2.2–2.5 (m, 8H), 4.1 (m, 1H), 4.45 (m, 1H), 5.9 (dd ($J_1$=10 Hz., $J_2$=20 Hz.), 1H), 6.5 (d (J=20 Hz.), 1H), 7.0–7.4 (m, 7H) |
| Ex. 20 ($CDCl_3$): | 0.35 (d (J=10 Hz.), 3H), 1.4 (d (J=10 Hz.), 3H), 1.8–2.2 (m, 3H), 2.4–2.9 (m, 3H), 3.8 (bs, 1H), 4.45 (bs, 1H), 5.3 (m, 1H), 5.9 (dq, 1H), 6.6 (d (J=20 Hz.), 1H), 7.0–7.6 (m, 8H) |
| Ex. 21 ($CDCl_3$): | 0.35 (d (J=10 Hz.), 3H), 1.4 (d (J=10 Hz.), 3H), 1.8–2.2 (m, 2H), 2.25–3.05 (m, 4H), 3.8 (bs, 1H), 4.3 (m, 1H), 4.8 (m, 1H), |

TABLE VI-continued

N.M.R. Data

|  |  |
|---|---|
|  | 5.9 (m, 1H), 6.6 (d (J=20 Hz.), 1H), 7.0–7.6 (m, 8H) |
| Ex. 22 (CDCl$_3$): | 1.5 (d (J=8 Hz.), 6H), 1.8–2.1 (m, 2H), 2.5–2.8 (m, 2H), 4.4 (m, 1H), 5.2 (m, 1H), 5.9 (dd (J$_1$=10 Hz., J$_2$=20 Hz.), 1H), 6.55 (d (J=20 Hz.), 1H), 7.1–7.5 (m, 8H) |
| Ex. 23 (CDCl$_3$): | 1.5 (d, 6H), 1.8–2.1 (m, 2H), 2.4 (s, 6H), 2.5–3.0 (m, 2H), 4.4 (m, 1H), 5.2 (m, 1H), 5.9 (dd, 1H), 6.6 (d, 1H), 6.95–7.45 (m, 7H) |
| Ex. 24 (CDCl$_3$): | 1.3 (t, 3H), 1.5–2.0 (m, 6H), 2.5 (d, 2H), 3.2 (s, 1H), 3.8 (s, 1H), 4.2 (q, 2H), 4.2–4.45 (m, 2H), 5.5 (dd (J$_1$=10 Hz., J$_2$=20 Hz.), 1H), 6.5 (d (J=20 Hz.), 1H), 7.0–7.45 (m, 8H) |
| Ex. 25 (CDCl$_3$+CD$_3$OD): | 1.5–2.4 (m, 8H), 4.1 (m, 1H), 4.3 (m, 1H), 5.5 (dd (J$_1$=10 Hz., J$_2$=20 Hz.), 1H), 6.4 (d (J=20 Hz.), 1H), 7.0–7.5 (m, 8H) |
| Ex. 26 (C$_6$D$_6$): | 0.9 (t (J=10 Hz.), 3H), 1.1–2.4 (m, 14H), 3.8 (q (J=10 Hz.), 2H), 3.9–4.4 (m, 2H), 6.0 (dd (J$_1$=10 Hz., J$_2$=20 Hz.), 1H), 6.7 (m, 1H), 6.8–7.8 (m, 8H) |
| Ex. 27 (C$_6$D$_6$): | 0.9 (m, 3H), 1.2–2.5 (m, 12H), 3.8 (m, 2H), 4.0 (m, 1H), 4.1–4.3 (m, 1H), 5.9 (dd (J$_1$=10 Hz., J$_2$=20 Hz.), 1H), 6.8 (dd (J$_1$=10 Hz., J$_2$=20 Hz.), 1H), 6.9–7.5 (m, 9H) |
| Ex. 28 (CDCl$_3$): | 1.3 (t, 3H), 1.4–2.5 (m, 16H), 3.7 (m, 2H), 4.2 (q (J=10 Hz.), 2H), 6.8–7.3 (m, 8H) |
| Ex. 29 (CDCl$_3$): | 1.27 (t, 3H), 1.5–2.3 (m, 10H), 1.82 (s, 3H), 2.48 (d, 2H), 3.11 (bs, 1H), 3.7 (bs, 1H), 4.16 (q, 2H), 4.23–4.4 (m, 2H), 5.68 (dd (J$_1$=8 Hz., J$_2$=18 Hz.), 1H), 6.13 (d (J=18 Hz.), 1H), 6.91–7.37 (m, 7H) |
| Ex. 31 (CDCl$_3$): | 1.25 (t, 3H), 1.5–2.3 (m, 10H), 2.4 (s, 3H), 2.5 (d, 2H), 3.1 (s, 1H), 3.7 (s, 1H), 4.2 (q, 2H), 4.2–4.5 (m, 2H), 5.75 (q, 1H), 6.4 (d, 1H), 7.0–7.4 (m, 7H) |
| Ex. 33 (CDCl$_3$): | 1.3 (t, 3H), 1.65–2.4 (m, 10H), 2.5 (m, 2H), 3.1 (s, 1H), 3.7 (s, 1H), 3.9 (s, 3H), 4.2 (q, 2H), 4.3 (m, 1H), 4.5 (m, 1H), 5.8 (q, 1H), 6.5 (d, 1H), 6.8 (d, 1H), 7.15 (m, 2H), 7.2 (t, 2H), 7.4 (m, 2H) |
| Ex. 35 (CDCl$_3$): | 1.3 (t, 3H), 1.4–1.7 (m, 2H), 1.8–2.5 (m, 10H), 2.51 (s, 3H), 3.1 (bs, 1H), 3.65 (bs, 1H), 4.15 (m, 3H), 4.35 (bs, 1H), 5.6 (q, 1H), 6.3 (d, 1H), 6.8–7.4 (m, 7H) |
| Ex. 38 (CDCl$_3$+CD$_3$OD): | 1.4–2.4 (m, 12H), 3.4 (s, 3H), 3.8 (s, 3H), 4.1 (bs, 1H), 4.3 (bs, 1H), 5.6 (q, 1H), 6.2 (d, 1H), 6.3 (d, 1H), 6.6 (d, 1H), 6 9–7.3 (m, 4H) |
| Ex. 39 (CDCl$_3$): | 1.3 (t, 3H), 1.6 (m, 2H), 2.45 (m, 2H), 2.65 (m, 2H), 2.9 (m, 2H), 4.2 (q, 2H), 4.3 (m, 1H), 4.5 (m, 1H), 5.6 (q, 1H), 6.0 (s, 2H), 6.5 (d, 1H), 7.1–7.4 (m, 8H) |
| Ex. 40 (CDCl$_3$+CD$_3$OD): | 1.6 (m, 2H), 2.2–3.0 (m, 6H), 4.1 (m, 1H), 4.3 (m, 1H), 5.6 (q, 1H), 6.0 (s, 2H), 6.5 (d, 1H), 7.1–7.4 (m, 8H) |
| Ex. 41 (CDCl$_3$): | 1.64–2.37 (m, 10H), 2.5–2.6 (m, 2H), 3.02 (s, 1H), 3.63 (s, 1H), 4.2–4.5 (m, 2H), 5.09 (s, 2H), 5.79 (dd (J$_1$=8 Hz., J$_2$=18 Hz.), 1H), 6.45 (d (J=18 Hz.), 1H), 7.08–7.52 (m, 12H) |
| Ex. 42 (CDCl$_3$): | 1.4 (d, 6H), 1.72–2.4 (m, 10H), 2.54 (d, 2H), 3.2 (m, 1H), 3.65–3.81 (m, 2H), 4.0–4.5 (m, 5H), 5.78 (dd (J$_1$=8 Hz., J$_2$=18 Hz.), 1H), 6.45 (d (J=18 Hz.), 1H), 7.07–7.5 (m, 8H) |
| Ex. 44 (C$_6$D$_6$): | 0.9 (t (J=10 Hz.), 3H), 1.4 (dd (J$_1$=10 Hz., J$_2$=20 Hz.), 6H), 1.5–2.4 (m, 12H), 3.4 (m, 1H), 3.8 (q (J=10 Hz.), 2H), 4.15 (m, 1H), 4.4 (m, 1H), 5.8 (dd (J$_1$=10 Hz., J$_2$=20 Hz.), 1H), 6.9 (dd (J$_1$=1 Hz., J$_2$=20 Hz.), 1H), 7.0–7.6 (m, 4H). Also the following minor peaks due to the threo isomer: 4.55 (m), 5.9 (dd), 6.8 (d) |
| Ex. 46 (CDCl$_3$): | 1.25 (t, 3H), 1.3–2.2 (m, 20H), 2.5 (d, 2H), 2.9 (t, 1H), 3.25 (s, 1H), 3.8 (s, 1H), 4.2 (q, 2H), 4.35 (s, 1H), 4.55 (s, 1H), 5.8 (q, 1H), 6.65 (d, 1H), 7.2–7.6 (m, 4H) |
| Ex. 48 (CDCl$_3$): | 1.8–3.0 (m, 12H), 4.4 (m, 1H), 5.2 (m, 1H), 5.7 (dd (J$_1$=10 Hz., J$_2$=20 Hz.), 1H), 6.5 (d (J=20 Hz.), 1H), 7.1–7.5 (m, 8H). Also the following minor peaks due to the cis lactone: |

TABLE VI-continued

N.M.R. Data 4.3 (m), 4.7 (m), 5.8 (dd), 6.45 (d)

Each of Examples 12 and 42 may be separated by conventional means into four racemates each of which may be resolved by conventional means to obtain a total of eight stereoisomers; insofar as the hydroxy groups of the group of Formula a are concerned, the erythro isomers are preferred over the threo isomers, with the 3R,5S isomer being the most preferred and the 3R,5R isomer being the preferred threo isomer. Example 13 may be separated by conventional means into two racemates each of which may be resolved by conventional means to obtain a total of four stereoisomers; insofar as the group of Formula a is concerned, the 3R,5S isomer is preferred. Each of Examples 14, 16–19, 24–27, 29–41 and 43–47 may be separated by conventional means to obtain the pure erythro racemate and the pure threo racemate (if any is present) each of which may be resolved by conventional means to obtain the 3R,5S and 3S,5R isomers from the erythro racemate and the 3R,5R and 3S,5R isomers from the threo racemate; the erythro isomers are preferred over the threo isomers, with the 3R,5S isomer being the most preferred and the 3R,5R isomer being the preferred threo isomer. Example 15 may be resolved to obtain the 3R,5S and 3S,5R isomers, with the former being preferred. Example 28 may be separated by conventional means to obtain the pure erythro racemate and the pure threo racemate each of which may be resolved by conventional means to obtain the 3R,5R and 3S,5S isomers from the erythro racemate and the 3R,5S and 3S,5R isomers from the threo racemate; the erythro isomers are preferred over the threo isomers, with the 3R,5R isomer being the most preferred and the 3R,5S isomer being the preferred threo isomer.

Example 20 may be separated by conventional means into two racemates each of which may be resolved by conventional means to obtain a total of four stereoisomers; insofar as the group of Formula b is concerned, the 4R,6S isomer is preferred. Example 21 may be separated by conventional means into four racemates each of which may be resolved by conventional means to obtain a total of eight stereoisomers; insofar as the group of Formula b is concerned, the trans lactones are preferred over the cis lactones, with the 4R,6S isomer being most preferred and the 4R,6R isomer being the preferred cis lactone isomer. Each of Examples 22 and 48 may be resolved by conventional means to obtain the 4R,6S and 4S,6R isomers, with the 4R,6S isomer being preferred. Example 23 may be separated by conventional means to obtain the pure trans racemate and the pure cis racemate each of which may be resolved by conventional means to obtain the 4R,6S and 4S,6R isomers from the trans racemate and the 4R,6R and 4S,6S isomers from the cis racemate; the trans isomers are preferred over the cis isomers, with the 4R,6S isomer being most preferred and the 4R,6R isomer being the preferred cis isomer.

Throughout the examples, the term "reduced pressure" denotes aspirator pressure. Where no solvent is specified in connection with a solution, the solvent is water, and all solvent mixtures are by volume. When a reaction is carried out under nitrogen, dry nitrogen is used to maintain anhydrous conditions.

All nuclear magnetic resonance spectra were taken at ambient temperature on a 200 MHz. spectrometer. All chemical shifts are given in p.p.m. ($\delta$) relative to tetramethylsilane, and where a single $\delta$ value is given for anything other than a sharp singlet, it is its center point. In the N.M.R. data:
bs = broad singlet
d = doublet
dd = doublet of a doublet
dq = doublet of a quartet
m = multiplet
q = quartet
s = singlet
t = triplet The compounds of Examples 2, 5, 8, 9, 13, 15, 17, 19, 25, 30, 32, 34, 36, 38, 40, 45 and 47 (wherein Z is a group of Formula a wherein $R_{11}$ is sodium) may be converted into the corresponding compounds wherein $R_{11}$ is hydrogen or a different cation M, particularly M', by the processes set forth in the specification.

Each of the compounds of Examples 1–48 (including each of the components and each of the possible stereoisomers thereof) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

What is claimed is:

1. A compound of the formula

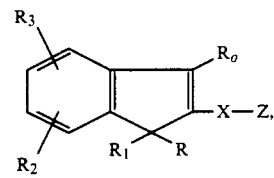

wherein $R_o$ is $C_{1-6}$alkyl not containing an asymmetric carbon atom, $C_{3-7}$cycloalkyl or

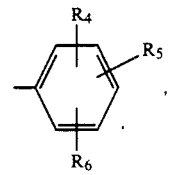

wherein $R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_5$ is hydrogen, $C_{1-3}$alkyl, $C_{1-3}$alkoxy, trifluoromethyl, fluoro, chloro, phenoxy or benzyloxy, and $R_6$ is hydrogen, $C_{1-2}$alkyl, $C_{1-2}$alkoxy, fluoro or chloro, with the provisos that not more than one of $R_4$ and $R_5$ is trifluoromethyl, not more than one of $R_4$ and $R_5$ is phenoxy, and not more than one of $R_4$ and $R_5$ is benzyloxy, R is hydrogen or primary or secondary $C_{1-6}$alkyl not containing an asymmetric carbon atom, and $R_1$ is primary or secondary $C_{1-6}$alkyl not containing an asymmetric carbon atom or R and $R_1$ taken together are $-(CH_2)_m-$ or $(Z)-CH_2-CH=CH-CH_2-$, wherein m is 2, 3, 4, 5 or 6, $R_2$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_3$ is hydrogen, $C_{1-3}$alkyl, $C_{1-3}$alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ is benzyloxy, X is $-(CH_2)_n-$, $-CH=CH-$, $-CH_2-CH=CH-$ or $-CH=CH-CH_2-$, wherein n is 1, 2 or 3, and

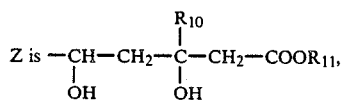

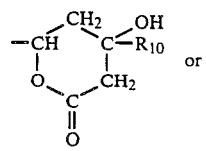  or

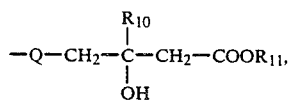

wherein Q is

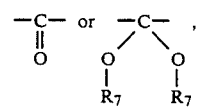

wherein each $R_7$ is primary or secondary $C_{1-6}$alkyl not containing an asymmetric carbon atom, the two $R_7$'s being the same, or the two $R_7$'s taken together are $-(CH_2)_q-$, wherein q is 2 or 3, $R_{10}$ is hydrogen or $C_{1-3}$alkyl, and $R_{11}$ is hydrogen $R_{12}$ or M, wherein $R_{12}$ is a physiologically acceptable ester group, and M is a cation, with the provisos that (1) Z may be

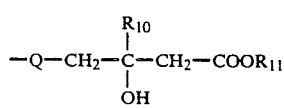

only when (i) X is $-CH=CH-$ or $-CH_2-CH=CH-$, (ii) $R_{10}$ is $C_{1-3}$alkyl or (iii) both (i) and (ii) and (2) when Z is

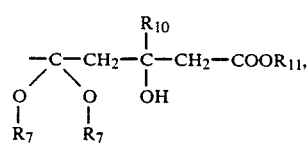

$R_{11}$ must be $R_{12}$ or M.

2. A compound according to claim 1 wherein M is a pharmaceutically acceptable cation.

3. A compound according to claim 2 wherein R is hydrogen or primary or secondary $C_{1-6}$alkyl not containing an asymmetric carbon atom, $R_1$ is primary or secondary $C_{1-6}$alkyl not containing an asymmetric carbon atom, and

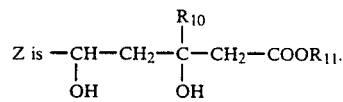

4. A compound according to claim 3 wherein $R_o$ is $C_{1-4}$alkyl not containing an asymmetric carbon atom or

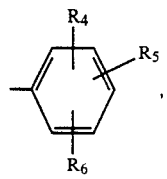

R is hydrogen or primary or secondary $C_{1-4}$alkyl not containing an asymmetric carbon atom, $R_1$ is primary or secondary $C_{1-4}$alkyl not containing an asymmetric carbon atom, $R_2$ is hydrogen, $C_{1-3}$alkyl, methoxy, fluoro, chloro or benzyloxy, $R_3$ is hydrogen or $C_{1-3}$alkyl, $R_{10}$ is hydrogen or methyl, $R_{11}$ is hydrogen, $R'_{12}$ or M, wherein $R'_{12}$ is $C_{1-3}$alkyl, n-butyl, i-butyl, t-butyl or benzyl, and X is $-CH_2CH_2-$ or $(E)-CH=CH-$.

5. A compound according to claim 2 wherein R is hydrogen or primary or secondary $C_{1-6}$alkyl not containing an asymmetric carbon atom, $R_1$ is primary or secondary $C_{1-6}$alkyl not containing an asymmetric carbon atom, and Z is 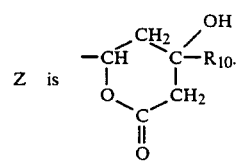

6. A compound according to claim 5 wherein $R_o$ is $C_{1-4}$alkyl not containing an asymmetric carbon atom or

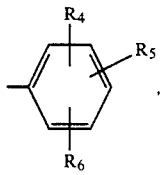

R is hydrogen or primary or secondary $C_{1-4}$alkyl not containing an asymmetric carbon atom, $R_1$ is primary or secondary $C_{1-4}$alkyl not containing an asymmetric carbon atom, $R_2$ is hydrogen, $C_{1-3}$alkyl, methoxy, fluoro, chloro or benzyloxy,
$R_3$ is hydrogen or $C_{1-3}$alkyl,
$R_{10}$ is hydrogen or methyl, and
X is —CH$_2$CH$_2$— or (E)—CH=CH—.

7. A compound according to claim 2 wherein R and $R_1$ taken together are —(CH$_2$)$_m$— or (Z)—CH$_2$—CH=CH—CH$_2$—, and Z is 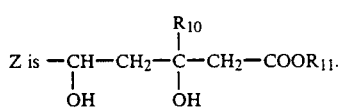

8. A compound according to claim 7 wherein $R_o$ is $C_{1-4}$alkyl not containing an asymmetric carbon atom or

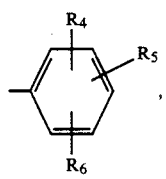

R and $R_1$ taken together are —(CH$_2$)$_m$—,
$R_2$ is hydrogen, $C_{1-3}$alkyl, methoxy, fluoro, chloro or benzyloxy,
$R_3$ is hydrogen or $C_{1-3}$alkyl,
$R_{10}$ is hydrogen or methyl,
$R_{11}$ is hydrogen, $R'_{12}$ or M, wherein $R'_{12}$ is $C_{1-3}$alkyl, n-butyl, i-butyl, t-butyl or benzyl, and
X is —CH$_2$CH$_2$— or (E)—CH=CH—.

9. A compound according to claim 8 wherein $R_o$ is

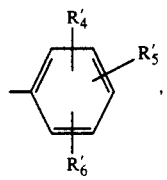

wherein $R'_4$ is hydrogen, $C_{1-3}$alkyl, trifluoromethyl, fluoro or chloro,
$R'_5$ is hydrogen, $C_{1-2}$alkyl, fluoro or chloro, and
$R'_6$ is hydrogen or $C_{1-2}$alkyl,
$R_{10}$ is hydrogen,
$R_{11}$ is hydrogen, $C_{1-3}$alkyl or M, and
X is (E)—CH=CH—.

10. A compound according to claim 9 wherein $R_2$ is hydrogen or $C_{1-3}$alkyl,
$R_3$ is hydrogen,
$R'_4$ is hydrogen or $C_{1-2}$alkyl,
$R'_5$ is hydrogen or fluoro,
$R'_6$ is hydrogen or methyl, and
$R_{11}$ is hydrogen, $C_{1-2}$alkyl or M.

11. A compound according to claim 10 wherein $R_2$ is hydrogen,
$R'_4$ is hydrogen or 3-methyl,
$R'_5$ is hydrogen or 4-fluoro,
$R'_6$ is hydrogen or 5-methyl, and
m is 2, 3 or 4.

12. A compound according to claim 11 wherein $R_{11}$ is a pharmaceutically acceptable cation.

13. A compound according to claim 12 having the formula

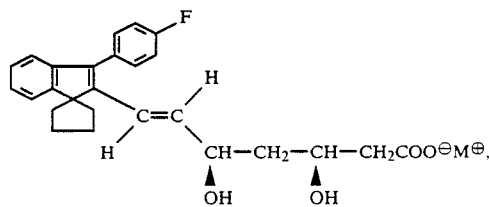

wherein M$^\oplus$ is a pharmaceutically acceptable cation.

14. The compound according to claim 13 wherein M$^\oplus$ is sodium.

15. The 3R,5S enantiomer of the compound according to claim 14.

16. The 3R,5S enantiomer of a compound according to claim 13.

17. A compound according to claim 2 wherein R and $R_1$ taken together are —(CH$_2$)$_m$— or (Z)—CH$_2$—CH=CH—CH$_2$—, and Z is 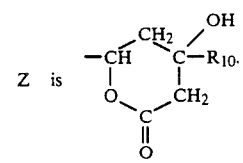

18. A compound according to claim 17 wherein $R_o$ is $C_{1-4}$alkyl not containing an asymmetric carbon atom or

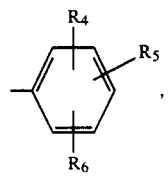

R and $R_1$ taken together are —(CH$_2$)$_m$—,
$R_2$ is hydrogen, $C_{1-3}$alkyl, methoxy, fluoro, chloro or benzyloxy,
$R_3$ is hydrogen or $C_{1-3}$alkyl,
$R_{10}$ is hydrogen or methyl, and
X is —CH$_2$CH$_2$— or (E)—CH=CH—.

19. A compound according to claim 2 wherein R is hydrogen or primary or secondary $C_{1-6}$alkyl not containing an asymmetric carbon atom,
$R_1$ is primary or secondary $C_{1-6}$alkyl not containing an asymmetric carbon atom, and Z is 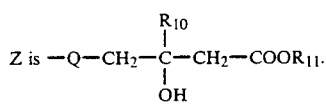

20. A compound according to claim 19 wherein $R_o$ is $C_{1-4}$alkyl not containing an asymmetric carbon atom or

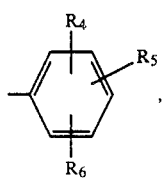

R is hydrogen or primary or secondary $C_{1-4}$alkyl not containing an asymmetric carbon atom, $R_1$ is primary or secondary $C_{1-4}$alkyl not containing an asymmetric carbon atom, $R_2$ is hydrogen, $C_{1-3}$alkyl, methoxy, fluoro, chloro or benzyloxy, $R_3$ is hydrogen or $C_{1-3}$alkyl, each $R_7$ is $C_{1-3}$alkyl or the two $R_7$'s taken together are $-(CH_2)_q-$, $R_{10}$ is hydrogen or methyl, $R_{11}$ is hydrogen, $R'_{12}$ or M, wherein $R'_{12}$ is $C_{1-3}$alkyl, n-butyl, i-butyl, t-butyl or benzyl, and X is $-CH_2CH_2-$ or (E)$-CH=CH-$, with the proviso that X may be $-CH_2CH_2-$ only when $R_{10}$ is methyl.

21. A compound according to claim 2 wherein R and $R_1$ taken together are $-(CH_2)_m-$ or (Z)$-CH_2-CH=CH-CH_2-$, and

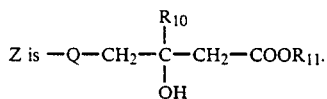

22. A compound according to claim 21 wherein $R_o$ is $C_{1-4}$alkyl not containing an asymmetric carbon atom or

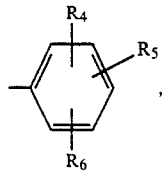

R and $R_1$ taken together are $-(CH_2)_m-$, $R_2$ is hydrogen, $C_{1-3}$alkyl, methoxy, fluoro, chloro or benzyloxy, $R_3$ is hydrogen or $C_{1-3}$alkyl, each $R_7$ is $C_{1-3}$alkyl or the two $R_7$'s taken together are $-(CH_2)_q-$, $R_{10}$ is hydrogen or methyl, $R_{11}$ is hydrogen, $R'_{12}$ or M, wherein $R'_{12}$ is $C_{1-3}$alkyl, n-butyl, i-butyl, t-butyl or benzyl, and X is $-CH_2CH_2-$ or (E)$-CH=CH-$, with the proviso that X may be $-CH_2CH_2-$ only when $R_{10}$ is methyl.

23. A pharmaceutical composition comprising an effective amount of a compound according to claim 2 and a pharmaceutically acceptable carrier, said effective amount being an amount effective for inhibiting cholesterol biosynthesis in a mammal.

24. A method of inhibiting cholesterol biosynthesis comprising administering to a mammal in need of such treatment an effective amount of a compound according to claim 2, said effective amount being an amount effective for inhibiting cholestereol biosynthesis.

25. A method of treating atherosclerosis comprising administering to a mammal in need of such treatment an effective amount of a compound according to claim 2, said effective amount being an amount effective for the treatment of atherosclerosis.

26. A method of treating atherosclerosis according to claim 25 comprising administering to a mammal in need of such treatment an effective amount of a compound of the formula

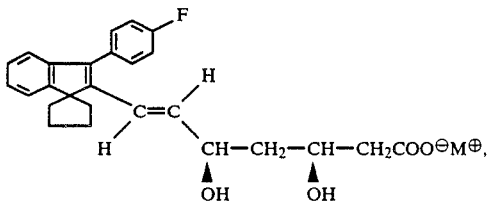

wherein $M^\oplus$ is a pharmaceutically acceptable cation, said effective amount being an amount effective for the treatment of atherosclerosis.

27. A method according to claim 26 wherein $M^\oplus$ is sodium, and the compound is in the 3R,5S enantiometric form.

* * * * *